United States Patent [19]
Hutchinson et al.

[11] Patent Number: 5,204,703
[45] Date of Patent: Apr. 20, 1993

[54] EYE MOVEMENT AND PUPIL DIAMETER APPARATUS AND METHOD

[75] Inventors: Thomas E. Hutchinson, Hardendale; Kevin S. Spetz, Lynchburg; Nirav R. Desai, Richmond, all of Va.

[73] Assignee: The Center for Innovative Technology, Herndon, Va.

[21] Appl. No.: 713,969

[22] Filed: Jun. 11, 1991

[51] Int. Cl.[5] .......................... A61B 3/14; A61B 3/00
[52] U.S. Cl. .................................... 351/210; 351/246
[58] Field of Search ............... 351/212, 243, 206–210, 351/246–247; 354/62; 128/731–745, 782

[56] References Cited

U.S. PATENT DOCUMENTS

| | | | |
|---|---|---|---|
| 4,676,611 | 6/1987 | Nelson et al. | 351/243 |
| 4,755,045 | 7/1988 | Borah et al. | 351/210 |
| 4,789,235 | 12/1988 | Borah et al. | 351/210 |
| 4,836,670 | 6/1989 | Hutchinson | 351/210 |
| 4,950,069 | 8/1990 | Hutchinson | 351/210 |

Primary Examiner—Rodney B. Bovernick
Assistant Examiner—Thong Nguyen
Attorney, Agent, or Firm—Staas & Halsey

[57] ABSTRACT

A subject's eye movement and pupil diameter are measured while the subject is exposed to visual stimuli. The apparatus and method utilizes an eye-look detector to determine a subject's visual examination of a presented image and by computer recording an analysis superimposes icons representing the lookpoints over the image. The apparatus and method are not only of value in running routine tests but also may be used for new experiments.

20 Claims, 5 Drawing Sheets

EYE MOVEMENT AND PUPIL DIAMETER APPARATUS AND METHOD

This invention relates to the determination of the movement of an eye, where it is looking and/or the pupil diameter of a person as he or she is stimulated with the presentation of various pictures and/or text.

BACKGROUND OF THE INVENTION

The reactions and behavior of the eye have been under study for many years. In fact, as early as 1765 it was known that dilations and constrictions of the pupil were not all attributable to lighting changes. It was not until the early 1970s that the psychological community began taking a stronger interest in both pupillary movements and eye saccades. The technology of the time was limited but the researchers managed to acquire a significant knowledge base relating to the eye.

Aside from the obvious effect that light intensity has on pupil diameter, many emotional reactions can cause dilation or constriction. The primary emotional states associated with pupil dilation are excitement, comfort, pleasure, and displeasure. Pupil dilation also occurs in response to impending threat or pain. In general, more unappealing stimuli are responsible for pupil constriction. An example of this type of stimulus would be a cross-eyed baby. Some stimuli, such as concentration camp scenes, initially cause pupil dilation, but with repeated exposure cause pupil constriction.

In general, the pupil can range in diameter from 1.5 to over 9 millimeters, and can react to stimuli in as little as 0.2 seconds.

Reported methods of measuring pupil diameter include: using a short-focus telescope with adjustable cross hairs, or taking pictures of the eye as a stimuli is presented then later measuring the pupil diameter with a ruler. Although each of these methods will produce valid results, the extensive time investment required and potential for human error are significant problems.

With the increased interest in pupillometry, there has also been a corresponding increase in the interest directed towards saccadic eye movements. The different movements made by the eyes can be broken down into two main categories: voluntary fixation movements and involuntary fixation movements. The fixation movements, or jumps, are called saccades, while the movements are called opticokinetic movements. The saccadic jumps made by the eye are so quick that only 10 percent of the time is the eye engaged in movement, the rest is spent fixating.

The voluntary movements, called macro-saccades, are responsible for selecting the visual target of interest. Once a target has been acquired, the involuntary fixation mechanism assumes control. These involuntary movements, called micro-saccades, are responsible for maintaining target fixation.

Many different methods of tracking saccades have been reported in the literature. These methods range in technology from using the electrooculogram (EOG) to using magnetic fields to induce a current in a coil imbedded into a contact lens. Of the saccade tracking techniques reported in the literature, almost all required some sort of invasive interface with the subject. These invasions are often uncomfortable and inhibiting to the subject.

SUMMARY OF THE INVENTION

The present invention is a specific application of the type of apparatus disclosed in U.S. Pat. Nos. 4,950,069 and 4,836,670 which disclosures are hereby incorporated herein by reference and made a part hereof.

The present invention utilizes a relatively inexpensive computer based apparatus and method for determining the lookpoint of a subject's eyes as well as the pupil diameter while the subject is viewing an image such as picture or text or a combination of a picture and text. These lookpoints and pupil diameters are nonintrusively recorded and may be correlated with a meaning thereof. The apparatus and their method may be used for testing the images such as a choice for new packaging or testing the psychological state of mind or the manner by which a person reads text. The basic platform of the invention can be a measuring apparatus and method for performing a variety of psychological experiments or test of stimuli and, based on empirical data or other information, have various meanings assigned to the results. The most notable advantage is the non-invasive method used to monitor the subject. A second major advantage provided with the technology is real-time processing. The system can gather information concerning both pupil diameter and lookpoint and then react to this information as it is gathered. This capability opens the door for many types of testing experiments previously unavailable. The system provides not only a non-invasive method for eye tracking, but also an automated environment for stimuli presentation. The apparatus can track a subject's eye-gaze with a resolution of 1 to 1.5 of eye rotation and a speed of 15 frames/second. Both the resolution and speed is expected to improve as the underlying technology is improved.

Many things haven't been explored further because of the measurement apparatus used to measure pupil diameter are either too slow, don't measure accurately or frequently enough, are too uncomfortable, are invasive, or don't measure in real time, or they aren't portable. All of these things inhibit the use of pupil diameter in further research of psychophysiological phenomenon.

The present system provides all of these extra advantages and permits looking into areas further which haven't been explored.

The use of the invention is primarily in psychological, technological, industrial, military, ethical, and political areas. As an example, pupil diameter is related to mental workload. Mental workload estimation quantifies the information processing demands upon a human operator. Pupil diameter is linked to mental workload. By assessing a person's mental workload, tasks and equipment can be designed to better suit the workload of a user and tasks can be reallocated between humans and machines so that a human is not overloaded with work. Also, decisions can be made on who you want to select to operate certain machines. Other applications include lie detection, drug use marketing applications, pictures involving what packaging arouses people's interest, etc. When people are aroused their pupil diameter usually dilates. Still other applications include economic impacts. As an example, if someone is overloaded then they are more likely to get sick or and the employer is going to have to pay for the sickness, etc.

In marketing applications, the apparatus permits the determination of the lookpoints on specific images. One example uses two pictures, both pictures containing the same product with different packages and the apparatus determines which picture the person prefers to look at, or which picture their pupil diameter is larger when the packages are viewed.

Another example, usable for determining intelligence of children in the toddler age, is to have a picture of mother and a stranger and see who the baby looks at first and what part of the mother or stranger the baby looks at and which one they look at more often. Also, a determination can be made to what extent there is a correlation with pupil diameter.

Areas of interest on the screen may be defined by a box technique. The box is defined as that area you are interested in seeing how often somebody is looking into. So, if you want to analyze that area, then you need to define it. A box file is created. The box file contains up to 15 different boxes and each of those 15 box definitions are described by the upper left and the bottom right corner of each box. A box is defined by entering the coordinates of the top left corner and of the bottom right corner. The box can be placed around any area of the computer screen. Also, because box coordinates are based on the screen, and not on the picture, box coordinates can be used for different pictures. This is helpful if it is desired to see if somebody looks at the left side of the screen more often than the right side of the screen. By defining boxes on the left side and the right side and they would be independent of the pictures that were being viewed on the screen. The system permits having a model and a package in each image, and determine whether a person looked at the model more or at the package more and also would permit a comparison between the two images. Originally it would only be determined how often somebody looked at one image or the other but now it can determined if the person is paying attention to the model or if they are paying attention to the package. This permits a determination of what to improve. If the total picture is viewed, this necessarily would not show what specific things were going on. I mean, what specific areas were the lookpoints. The lookpoints can be superimposed but in order to analyze the number of lookpoints, a manual count of the lookpoints in a certain area would be required. The use of boxes is a way of simplifying the analysis of what a person is looking at.

DESCRIPTION OF THE PREFERRED EMBODIMENT

In this description, including the accompanying drawings, there is shown and described a preferred embodiment of the invention. Others skilled in the art will understand the invention and the principals thereof and will be able to modify the preferred embodiment and embody the invention in a variety of forms, each as may be suited for the conditions of a particular case.

DETAILED DESCRIPTION OF THE INVENTION

Figure 1:
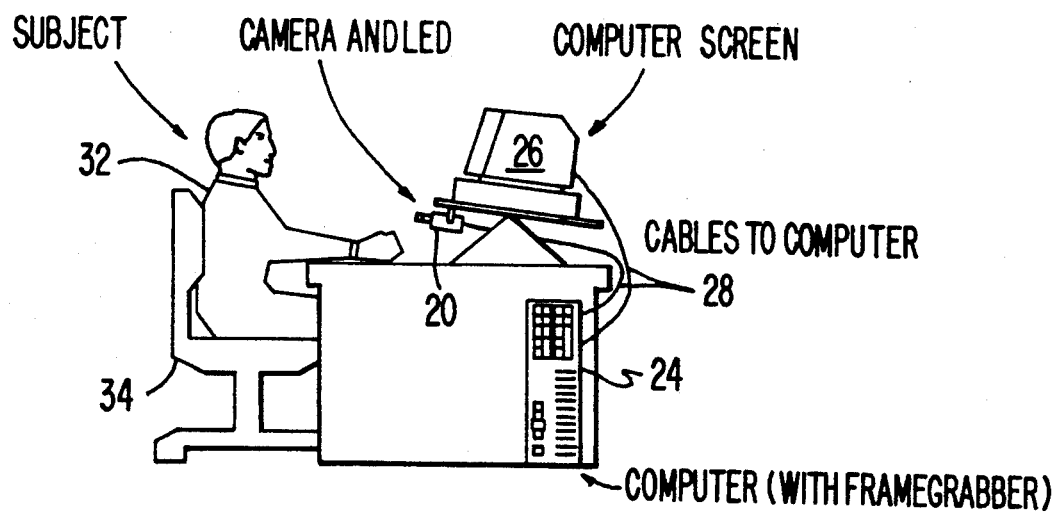
FIG. 1 shows schematically a typical set up of the apparatus.
Figure 2:
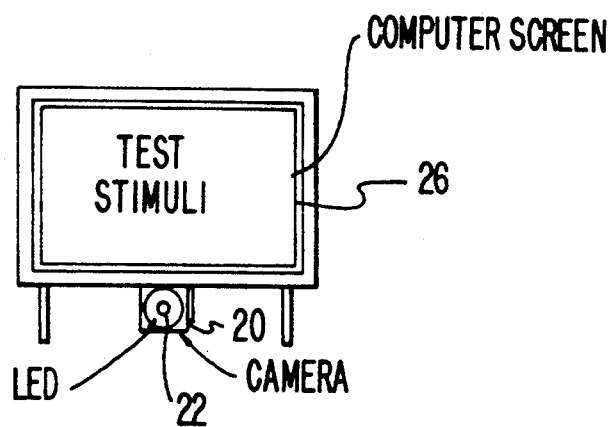
FIG. 2 shows schematically the test and camera arrangement as viewed by the subject.
Figure 3:
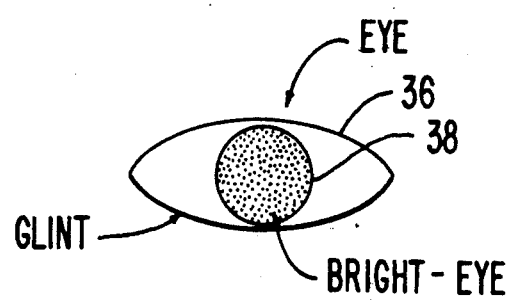
FIG. 3 shows a typical relationship between the pupil as outlined by the bright-eye effect and the glint.

With reference to FIGS. 1, 2 and 3 there is shown the basic apparatus and technology of this invention in schematic form. This is more fully explained in U.S. Pat. Nos. 4,950,069 and 4,836,670 mentioned supra.

The gaze routines as more fully set forth in the appendix and below provide the lookpoint and pupil diameter of a user to applications software in real time. The format of information exchange between applications programs and the gaze routines is standardized so the same gaze engine is common to all applications. Individual application packages decide how or if the lookpoint and pupil diameter information is to be used.

The hardware utilized by the gaze routines to produce the lookpoint information includes generally a computer with frame-grabber board 24, a infrared sensitive standard surveillance camera and lens 20 and an image presentation device such as a computer monitor 26, and a near infrared light emitting diode (LED) with a light condensing lens 22. The surveillance camera 20 is situated underneath the computer monitor with cables 28 feeding the signal to the frame grabber-board in the computer. Mounted coaxially with the lens is the LED and light condensing lens. The arrangement is assembled into a desk or console 30 which is at a convenient height for a subject 32 to sit on a chair 34 in front of the monitor 26. When the camera is pointed at one of the user's eyes 36, the LED 22 floods the user's face with near infrared light, producing the effect commonly called the bright eye. The bright eye outlines the pupil 38 is the same sort of effect that causes a cat's eyes to glow at night or a person's eyes to glow red in a flash picture. Two features are immediately apparent in the infrared image of the eye: the glowing bright eye effect and the virtual reflection of the LED off of the surface of the eye, which is called the glint 38. It is the presence of the bright-eye and the glint which prompts the technology to determine lookpoints as the distance and direction between the center of the pupil and the glint is used in making the determination.

When the gaze routines are told to deliver a lookpoint (i.e. answering a request from applications software for the current screen location at which the subject is looking), the first operation is to grab a frame. Grabbing a frame simply involves taking the image currently in the frame buffer and holding it for analysis. Taking advantage of the image contrast, the gaze routines can scan the frame and locate the pupil and the glint. The vector relationship between the pupil center and the glint center is used by the gaze routines to calculate a lookpoint. If this lookpoint is determined to be outside of the bounds of the computer display the applications program is notified and the data processed accordingly (depending upon the application, off-screen lookpoints may be processed or ignored). Since the edges of the pupil are used to determine the location of the pupil center, the pupil diameter is generated in the process.

In order to use the vector connecting the pupil and glint centers to calculate a lookpoint, the gaze routines must first be calibrated. Calibration involves placing icons (targets a which the user is instructed to look) on the computer display and, while the user is looking at them, processing image frames and isolating the pupil/glint vector. As the icon is moved to different locations on the screen, the vector is continually calculated. When all of the calibration icons have been presented, the calibration data is fit to a curve thus producing the equations to be used in calculating the gaze point.

The final operation the gaze routines perform is to save the previous locations of the pupil and glint center. When the routines receive the next request for lookpoint information, the previous pupil and glint center locations are used to speed up the search.

The gaze routines complete the search for the pupil and glint centers in approximately 10 ms (milliseconds). Due to limitations in the frame-grabber hardware, a new frame, and therefore a lookpoint, can only be produced every 33 ms but this will improve with future hardware. The gaze routines achieve this speed by taking advantage of information contained in the previously processed frame to find the new pupil and glint centers. If for some reason the eye is lost, global search routines are activated which scan the entire frame for the pupil and glint.

Once the global routines have been successful in locating the eye local routines assume the task of processing subsequent frames. The local search routines first perform a spiral search out from the previous glint location to find the new glint center. This method takes advantage of the fact that the glint moves very little between frames. If the search routines are successful in finding the glint, the local pupil search routines are called. Otherwise, the global routines are reactivated.

The local pupil search routines use the previous pupil center and expected pupil diameter to quickly find the edge of the new pupil image. By taking advantage of pupil diameter information, the software can jump to the expected location of the pupil edge and eliminate the need to scan all the way across the eye. The number of pixels scanned can be reduced up to 70% using this procedure. Since accessing pixels in the frame buffer is relatively slow, reducing the number of pixels scanned results in a proportional increase in speed.

The technology can detect eye rotations of as little as 1.5°. This corresponds to approximately 84 boxes on a screen. The actual accuracy of the system varies with head position and may vary with gaze direction, depending upon which curve fit is used and the positions of the calibration points.

The calibration curve fit adopted with the gaze routines was a first order model with a y dependence. The equation defining this fit is as follows:

$$k = B_0 + B_1 j_1 + B_2 j_2$$

where, in calculating the x component of the lookpoint, $j_1$ is the x component of the pupil/glint vector and $j_2$ is the y component of the pupil glint vector. $j_1$ and $j_2$ are reversed when calculating the y component of the lookpoint. In order for the y dependence to be stable, the shape of the region bounded by the calibration point positions must be the same as the shape of the area where the user will be looking (i.e. the calibration point positions extend to the borders of the screen). If a more simple calibration procedure is required (i.e. less calibration points for the subject to follow), a curve fit with no y dependence may be used. The current curve fit of choice for this situation is a simple second order model, $$k = B_0 + B_1 j_1 + B_2 j_2$$

The target accuracy for the system is 0.5° of eye rotation or better. With this accuracy, the system would be on the threshold of detecting micro-saccades. These micro-saccades are important for some testing and future improvements will permit an accuracy and speed that they will be detected using basically the same apparatus and methods used in the present invention.

One of the primary variables of interest in measuring response is pupil diameter. It is for this reason that the gaze routines were adapted to produce not only lookpoint information, but pupil diameter as well. The system does not use any sort of range finding capability (no information concerning the distance from the head to the camera), so an absolute value for pupil diameter is not calculated; however, a relative value is produced. Since relative changes in pupil diameter are the main interest and not actual pupil size, this has proven to be sufficient but a range finding capability can be added if desired.

One of the most critical steps in making the eye-gaze engine work is the calibration. If the calibration is not performed correctly, or the software fails to find the pupil and glint accurately during the calibration, the coefficients generated can be useless. The gaze routines test the calibration for accuracy; if any calibration icon position calculated with the calibration equations differs from the actual position by more than 5%, the calibration is rejected. The result of verifying the calibration provides reliability in the data produced by the eye-gaze engine.

The basic cornerstone of the testing system of the present invention is that people will react to certain stimuli and the system detects these reactions. Since the testing system itself is usually the presenter of the stimuli, it is a relatively easy task for the computer to correlate the reaction data to the stimuli. If, however, the stimuli originates from another source, such as a recording, projected slide, or picture, the system will still allow data points of significance to be labelled. These labelled data points can be used to match the reaction data to the correct stimulus. An example of this practice would be using a recorded auditory stimulus and labelling the data point taken when recording was started.

The types of stimuli the system is capable of presenting can be divided into two categories text and pictures. Each of these stimuli types are usually presented to the subject on the computer screen. The picture classification can be further broken down into those picture which fill an entire screen and those pictures which are displayed in different boxes or a divided screen.

The single picture display has been provided so that a subject's reaction to a single scene can be monitored. The larger image is more intense and provides greater detail, possibly leading to stronger subject reaction. The images which are displayed as groups such as groups of four are correspondingly smaller. With this reduction in size comes a proportionate loss of detail. The advantage of this display format is that a subject can not only register a reaction to the individual images, but a preference of certain images over others can be indicated.

The design of the system does not limit it to performing tests only with stimuli presented by the system. Tests can be given where other forms of stimuli presentation are used. Performing tests which use senses in addition to sight for stimulation (i.e. smell and auditory stimuli).

Once a test has been designed and the stimuli entered into the system, a sequence of subject tests can be run. The subject is lead into the testing environment (usually a small, quiet room) and placed in front of the computer monitor. If the test has already been completely set up, all that will be displayed on the screen is the instruction, "Press a Key". At this point the administrator of the test, sometimes referred to herein as the operator, will explain to the subject how the test will be run, and the requirements of calibration. Once briefed, the administrator will start the test (by pressing a key) and the first stimulus will be presented to the subject. The system will automatically move from stimulus to stimulus as the test is administered. After the test is complete the software returns to a simple menu of options. At this point, the administrator can elect to present another test, or proceed to the next subject. All gathered data and data analysis are hidden from the subject.

Once a subject has been tested, it is a relatively straight forward process to analyze the results and extract useful information. The system provides reliable information concerning the subject's lookpoint and relative pupil diameter. The gaze engine may also be used to extract information concerning saccadic velocities and other parameters.

For individual or unrelated stimuli screens, the resulting data files are analyzed one at a time. The data is processed to find average pupil diameter, and, when appropriate, broken down into lookpoints lying on the displayed images. In this way a subject's preference for a certain image or portion of the screen can easily be discovered.

The results from stimulus screens can be processed as groups and multi-factor tests can be designed which are sensitive to possible stimulus effects. Using the group processing capability, the tests can be designed such that the same figure appears in different screen locations (assuming that the multiple picture screen model is being used) at different times. When the results are being processed the system can analyze each individual screen, examining quadrant effects, and then process the screens as a group, focussing on stimulus effects.

The software system developed for testing was designed as a general package capable of presenting a wide variety of stimuli to a test subject. The stimuli are grouped into two different categories: text and pictures. Obviously, both text and pictures can be used simultaneously. Extended test sequences can be generated which are composed of any combination of stimuli in these categories. Tests can also be run with nothing displayed to the subject. With the screen left blank, the operator is free to test a subject's response to other categories of stimuli.

Since many of the potential users (i.e. experimenters) of the software system have fields of expertise that do not include computer operation, a user friendly environment is very important. To realize this environment, the software is designed using menus and windows to clearly and efficiently provide the experimenter or operator with information. In the event of an error, the software informs the user and allows the mistake to be corrected if possible.

The menus are configured in a simple tree structure. Menu selections can be chosen by moving a selection bar with the keyboard arrow keys, or by typing the hot character associated with each menu option. After a menu option has been selected the user is either presented with another menu, or the selected operation is performed. If at any time the user selects an operation that will result in the destruction of data, the system requests confirmation from the user. The tree structure used in the menus partitions the software's tasks into three different sections: entering data, performing tests, and analyzing data.

The forms of stimuli that the system is capable of presenting to the subject are text and pictures or a combination thereof. These stimuli are displayed on a standard EGA graphics screen for a personal computer. Since the system allows the experimenter or operator to create the text and pictures used for testing, the different possible stimuli are unlimited.

When entering text stimuli into the system the experimenter is presented with a blank area of the screen in which to type. The screen is treated much like a blank piece of paper in a typewriter, imposing no format rules on the entered text. The characters are entered through the keyboard and can be displayed in any of the computer's available colors.

The graphic stimuli may be entered into the system through the surveillance camera used by the eye-gaze algorithms to follow the user's eye. The desired image is simply held in front of the camera and the frame frozen. Once captured, a variety of image processing functions are available for image enhancement. The image can be transferred to the computer's graphics screen and stored to later be displayed during a test.

The images transferred to the computer screen, have been classified into size categories: full screen images, part screen and box images. Full screen images cover almost the entire computer screen and are displayed one at a time. The part screen images and boxes cover only part of the screen and can be displayed as groups.

As one example, the images captured by the present frame-grabber have a spatial resolution of $512 \times 480$ and a contrast resolution of 256 grey levels. The image quality of this type of image is consistent with that of a standard black and white television. An EGA (Enhanced Graphics Adapter—a standard graphics card) graphics card in the computer, however, has a spatial resolution of $640 \times 350$ and can display 16 colors at one time. This will give 16 different shades of blue that can be assigned as the EGA's color palette. Image intensities from the frame-grabber are translated to one of these grey level values and displayed on the EGA screen.

Even though the frame-grabber images have the potential to span the 256 gray levels, they normally use only part of the range. As a result, the image transferred to the EGA screen only uses a comparable portion of the 16 grey levels available on the EGA. This low image contrast, while not a problem with 256 grey levels, can cause significant image degradation with only 16 grey levels.

Other reasons for pre-processing the images sent to the EGA screen include: image simplification, and image reduction. Some of the images to be processed may be simple line drawings. Camera noise and lighting gradients can make the images appear more complex than is necessary. For the stimuli to be as effective as possible, these simple images should be as artifact free as possible.

In order to maintain good image contrast when transferring pictures to the EGA screen, an image equalization is done. This process involves altering the image's histogram to have a flat power density function (PDF), and therefore one which extends through the entire range of grey levels. After equalization, an image transferred to the EGA graphics screen will utilize all 16 of the available grey levels.

When displaying simple line drawings on the EGA screen, it is normally preferable to use only two grey levels. For these cases, software functions allow the experimenter or operator to convert an image to only black and white (no grey levels in between). When displayed on the EGA screen these images resemble the original drawing much more closely.

Finally, in order to make the images small enough to display on the EGA screen in groups such as four, the frame-grabber images must be reduced. To accomplish this a simple reduction algorithm is used which reduces a frame to one ninth of the original size. The software uses an averaging method for reduction so camera noise is reduced in the process.

Once test stimuli have been entered into the system, they can be presented to a subject during a test. While the stimulus is being displayed on the screen the system will monitor and store the lookpoint and pupil diameter of the subject. Several system features allow for slightly different testing environments. The experimenter or operator can vary the number of screens presented to the subject during the test, vary the length of time each screen is displayed, and turn off or on lookpoint feedback to the subject. Usually, lookpoint feedback to the subject is not used during the test.

In order to increase the speed of testing and make reproducing tests easier, the software provides the capability of generating test batch files. A test batch file contains a list of test stimuli to be presented to the subject, and a list of files in which the results are stored. A batch file may be programmed to present as many or as few stimuli screens as desired.

Under certain conditions it may be desirable to provide the subject with lookpoint feedback. Before the system executes a test, the experimenter or operator is asked whether or not the subject's lookpoint should be displayed. When feedback is desired the computer will place a small round icon at the screen position where the gaze routines have calculated the subject to be looking. The subject's behavior will be influenced by this lookpoint feedback.

Another operational parameter of the testing procedure is the test length. Before the test sequence is presented the experimenter is asked how long each screen should be displayed. Screen display time is usually measured in number of lookpoints calculated instead of seconds; in other words it takes data until so many data points are taken instead of for a given amount of time. This ensures that system delays in finding the pupil are not taken away from test time. Time may also be measured in conventional units (i.e. seconds).

Appropriate data analysis functions of the results obtained with the testing software are important and a variety of methods for presenting the test results have been provided. These functions have been designed to both present the raw data to the experimenter or operator and to summarize the information contained in the data file.

When the experimental sets of stimuli presented to the subject do not have any direct relation to each other (i.e. the same image does not appear on more than one screen), the results can be processed separately. The different possible processing functions include: listing the raw lookpoint and pupil diameter data, graphing the raw data verses time, superimposing the data back onto the stimuli, and summarizing the results. Listing the results involves writing to the computer screen the x and y lookpoint information, the pupil diameter and any data point labels added by the experimenter.

Superimposition is useful when the experimenter wants to correlate the subject's lookpoint and pupil diameter to a particular part of an image. With this function, the stimuli are first re-displayed on the computer screen. Each lookpoint from the data is then displayed as an icon at the determined location on the stimulus image, and the pupil diameter is shown in a corner of the screen. The data can be presented in real time, or stepped through under keyboard control. Also, the program can be modified to number the icons to show the sequence the lookpoints were generated and the dwell time at a location.

Another method of data display, graphing, is useful for following trends in the data. The data are separated into x lookpoints, y lookpoints and pupil diameters. Each parameter is then graphed with respect to time. Pupil diameter changes and strong saccades are easily seen with this display method.

Still another method of reviewing the results is with a data summary. This option is most useful when stimuli are presented as groups of pictures. The summary basically involves categorizing each lookpoint by the quadrant or section or box in which it appears. The mean and standard deviation of the pupil diameter are then calculated for the data points falling on each separate picture, and finally for the whole data set. This method makes readily apparent the subject's specific reactions to different stimuli.

Using the multiple images on a screen test model such as four different images, experiments and tests can be designed in which the same stimulus is presented on a number of different screens. On each of these screens, the stimulus may be located in a different quadrant, eliminating any effects from quadrant preference. In these cases it may be desirable to extract from each data file (a data file is made for each screen displayed during the test) those lookpoints which fell upon this certain image. To do this, the administrator may select a group of related files and instruct the software to summarize all of the lookpoints falling on all of the images represented in that list of files. The summary generated is the same as for the separately processed results. For each image (one of the four images presented on a screen), the total number of lookpoints and the mean and standard deviation of the pupil diameter is calculated.

Certain quadrants attracted more lookpoints from subjects than others, possibly stemming from reading habits. The upper two quadrants are significantly more preferred than the lower two. There is also a strong correlation between the number of lookpoints a stimulus received and the stimulus complexity. The least complex object receives the fewest lookpoints, while figures having the highest complexity receives the most.

The relationship of pupil diameter to stimulus complexity and stimulus quadrant has been evaluated. In none of the examined relationships were any significant effects found. Pupil diameter did not have any strong connection to complexity, presentation sequence, or quadrant.

An easy method of entering pictures into the system involves holding the desired stimuli in front the surveillance camera and freezing the image. Once frozen, the image is enhanced and transferred to the EGA graphics screen. The major problem with this method is the relatively poor quality of images that the system is capable of capturing. Image quality suffers because of variations in lighting and glares off of the original stimuli held in front of the camera. A more robust method of picture entry utilizes a scanner or some other method of picture entry which is designed for image capture of higher quality images. The major advantage, however, of the current method is that no extra equipment is necessary.

Some experiments o tests involve target tracking. In these scenarios the subject is shown a screen with a moving target. After the subject is told to follow the target as closely as possible, the system would track the subject's lookpoint. The performance rating generated from the test results would be based upon the subject's ability to track the target. This may be used for drug testing, fatigue, some illnesses, etc.

One of the primary capabilities of the system is real-time data analysis and the decisions made based on that analysis. The normal batch file organization used for administering the tests is purely linear; regardless of what reaction the subject has the stimuli are always presented in a defined order. Processing the results as they are gathered allows the system to evaluate how the subject is reacting to certain classifications of stimuli and according to his reaction display more or less from this class. Described simply, the test that a subject receives would depend on that subject and his reactions during the test.

The testing system may use a second screen for computer output. The system shown in FIG. 1 displays all messages to the experimenter or operator and all stimuli to the subject on the same screen. With only one screen, trying to hide information about how the experiment is run is often difficult and cumbersome. If, however, the experimenter (operator) uses a private screen which the software use for test control then the required setup procedures easily be hidden from the subject. The addition of the second screen also allows the software to provide the experimenter with real time data analysis, while the subject's screen is presenting the test stimuli.

To test a subject, the first step is to register the subject. The next step would be to calibrate the subject. Load in the batch file or test file to be used for the test. The batch file contains a series of images, which is the pictures and the text which are to be displayed for the test. A key to begin the test is pressed and that's when the calibration begins. Once the subject goes through the calibration and the calibration is a good calibration, then the apparatus goes on and starts displaying the stimuli. Each screen could contain one large image or could contain two or more smaller images. Each screen is basically designed to collect a certain amount of lookpoints. Once it collects a predetermine number such as 250 or so data points, the system goes on to the next screen and displays different images. This repeats itself until all the desired images are viewed and the test completed. About 250 set points are collected in just a few seconds.

Figure 6:
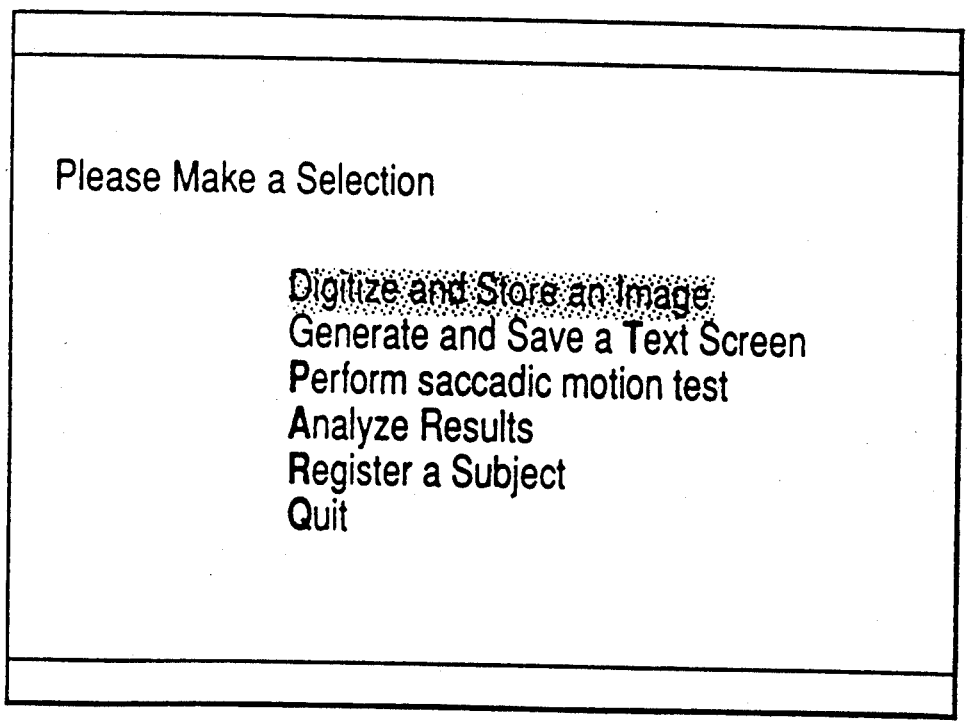
FIG. 6 shows the computer screen with the main menu pulled down.

FIG. 6 is the main menu from which a selection is made. The first choice is "Digitize and Store an Image" which is highlighted. That is where the camera itself can be utilized to take a picture in front of the camera, digitize it and store that image. Also, the image can be digitized and stored separately and placed in the memory to be pulled up or during the test.

"Generate and Save a Text Screen" is when the text material can be entered rather than being photographed. That can be entered from the keyboard.

"Perform Saccadic Motion Test" is when the test itself is being created. The "Analyze Results" is where all of the results files can be viewed. Lookpoints can be superimposed over images based on the results files.

"Register Subject" is the first step where a new subject is entered at the beginning of a test. Finally, "Quit" is utilized to leave the main menu.

Figure 7:
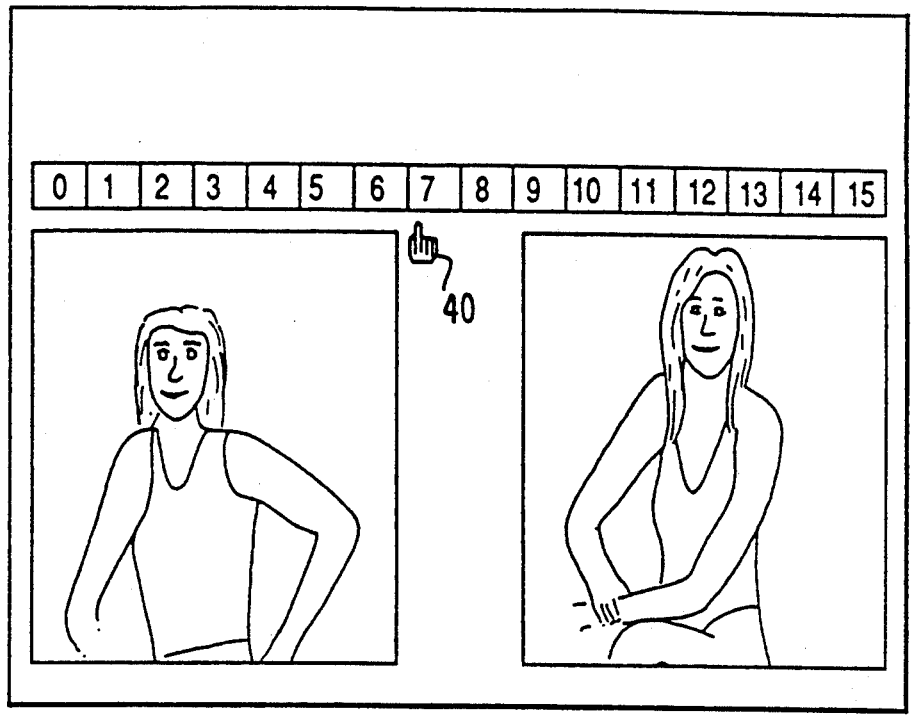
FIG. 7 shows a test stimuli having two models presented.
Figure 8:
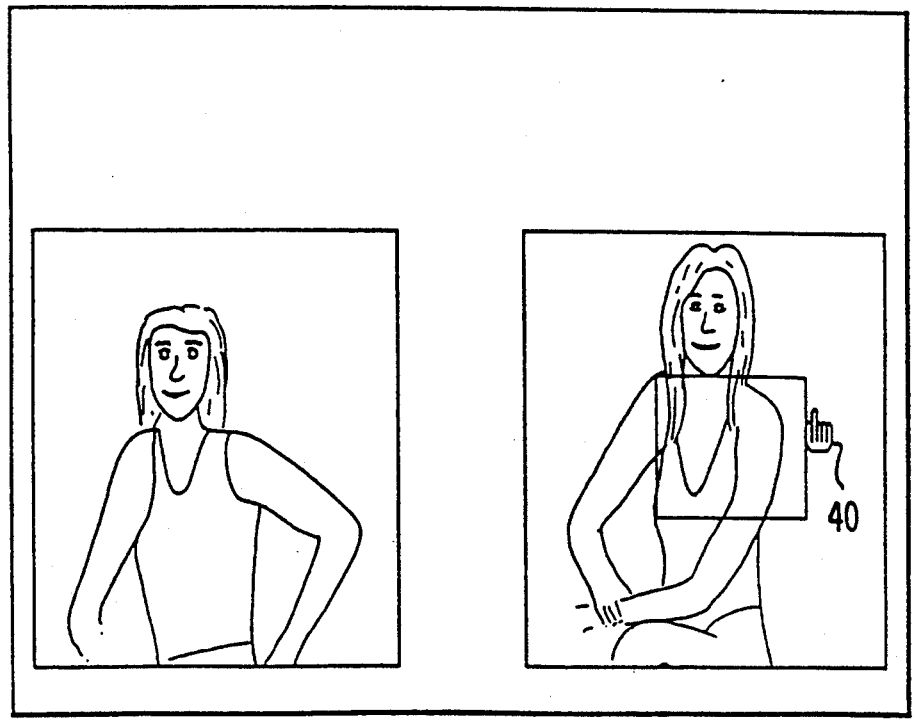
FIG. 8 shows the test stimuli of FIG. 7 with a part outlined in a box.

FIG. 7 defines a box file. Two models are shown as being represented in a picture and a box file is being formed for later review. Basically, the option called "Define a Box Option" is selected and it first asks the user to define the upper left corner of the box by using the mouse. The mouse is moved to the desired area of the screen and the left mouse button is actuated to define the top left corner. Then the mouse is to define the bottom right corner. The 15 boxes represent the storage capacity of this particular program and the mouse 40 is pointing at box 7 in FIG. 7. After that box number 7 has been selected, then in FIG. 8 a certain area for that box to represent is selected around the left shoulder of the model on the right. The mouse position is shown by an icon 40 in the shape of a hand. The picture may be scanned for a predetermined period of time which is usually dependent upon the number of data points desired keeping in mind that usually it takes 30 milliseconds per data point. A typical scan may be 5 seconds.

Figure 9:
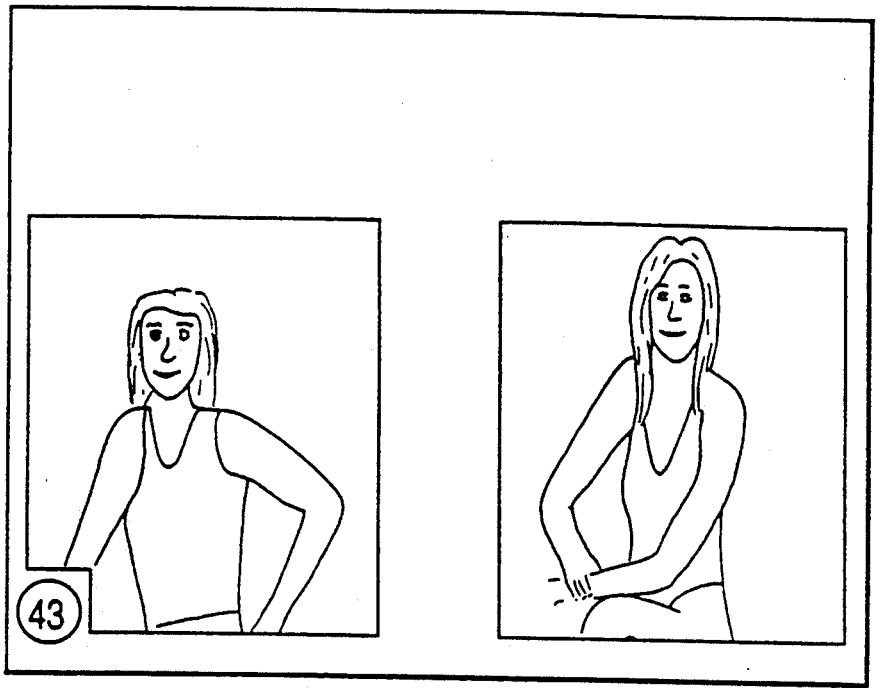
FIG. 9 shows the test stimuli of FIG. 7 with a lookpoint superimposed on the left model and the pupil diameter shown in the left lower box.

FIG. 9 shows the superimposition of a lookpoint and the pupil diameter on the picture just scanned. It shows that the subject looked at the right eye of the model on the left with the pupil diameter being 43 computer screen graphic pictels wide.

Figure 10:
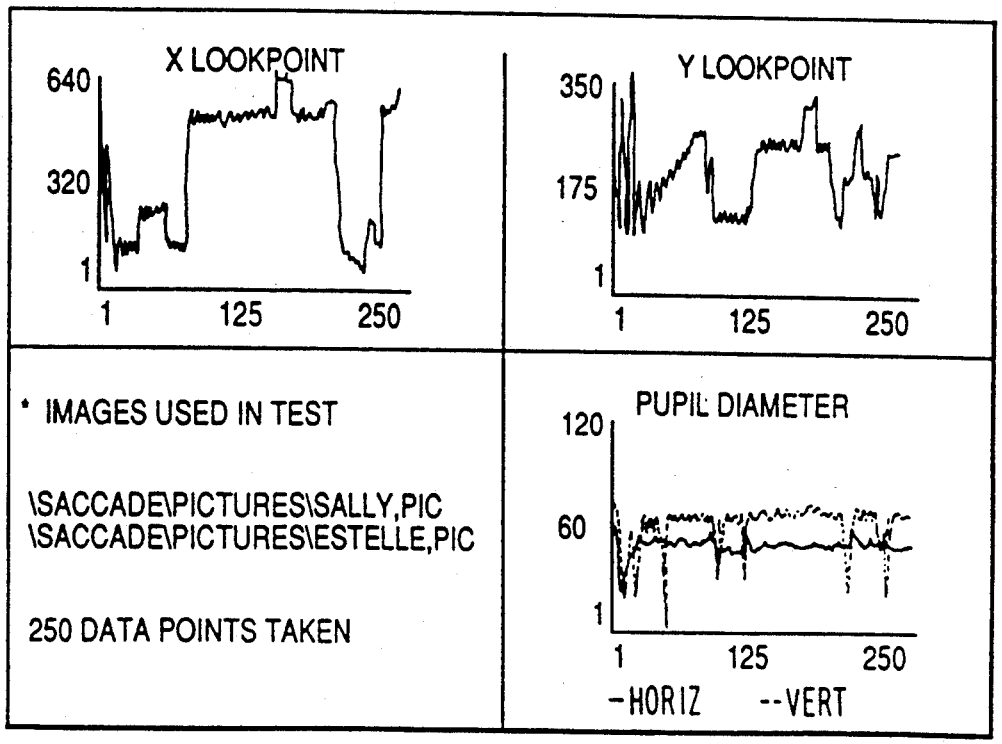
FIG. 10 shows the display of an analysis of X and Y lookpoints and pupil diameter.

FIG. 10 is an overall analysis of the results of the subject looking at a picture. The upper left quadrant and the upper right quadrant show the X lookpoint and Y lookpoint, respectively, where 250 lookpoints in total are viewed.

The X lookpoint vertical numbers are the lines of this particular EGA graphics screen which has 640 vertical lines so the top would be the far right line (640th line) and one would be the first line on the left.

The Y lookpoint vertical numbers represents the horizontal lines of 350 with the number 1 being the top line and number 350 being the bottom horizontal line. For screens having greater resolution, this would change accordingly with the screen and graphics utilized.

The lower right hand corner of FIG. 10 shows the change in pupil diameter with the light line representing the vertical (or whatever line is used in the graphics) and the dark line representing the horizontal. The vertical line in the lower right hand quadrant represents the number of pictels and the horizontal line represents the various lookpoints which are 250. The lower left corner shows the specific identification of the subject whose pictures are analyzed. It shows Sally and Estelle who are the two models shown and that 250 data points have been taken.

Figure 11:
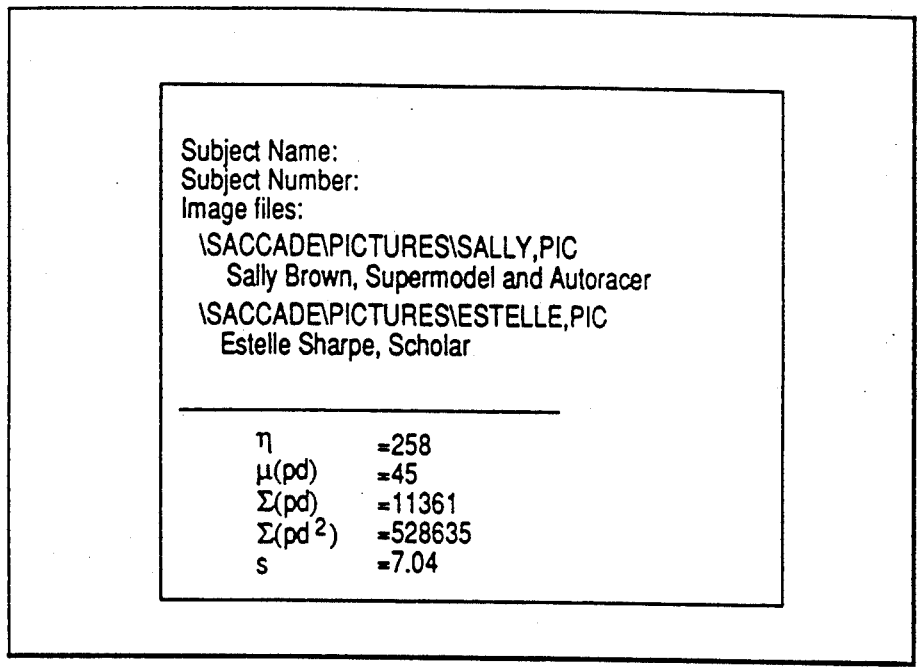
FIG. 11 shows a summary of an entire test.

FIG. 11 shows a summary of the entire test, the image files being the two models. The number of lookpoints are 250, u(pd) is pupil diameter and is 45 pictels. Sigma (pd) equals in effect the sum of the pupil diameters which is 11,361 and Sigma (pd$^2$) is the sum of the pupil diameter squared which is 528,635 and this is used to calculate "s", which is the standard deviation and equals 7.04. Standard deviation is an indication of how steady the pupil diameter is and would show to some extent the degree of excitability of th subject.

Figure 12:
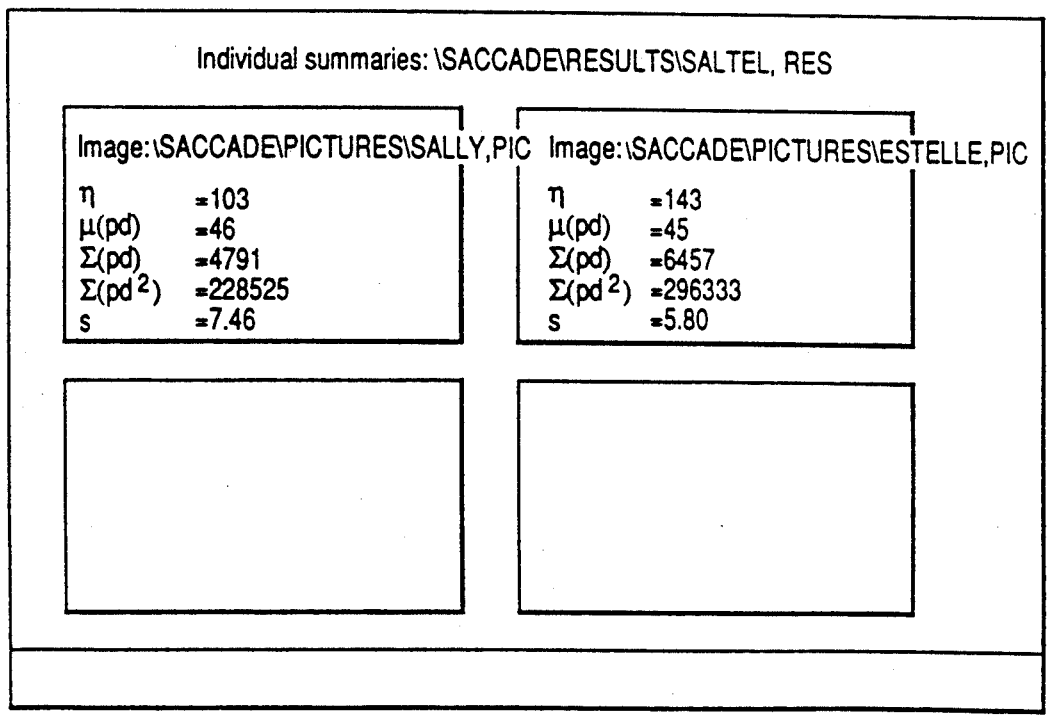
FIG. 12 shows individual summaries.

FIG. 12 shows the individual summaries between two boxes. The one on the left being a box for Sally and the one on the right being the box for Estelle. They shows that in this case there were 143 lookpoints for Estelle vs. 103 lookpoints for Sally indicating the box surrounding the total picture that the subject found Estelle more attractive to look at than Sally. However, there was a higher degree of excitement in the case of Sally because the standard deviation was higher.

Figure 4:
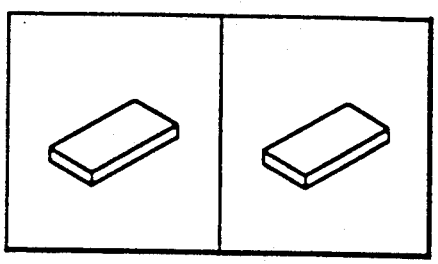
FIG. 4 shows a test stimuli where two different packages are presented.
Figure 5:
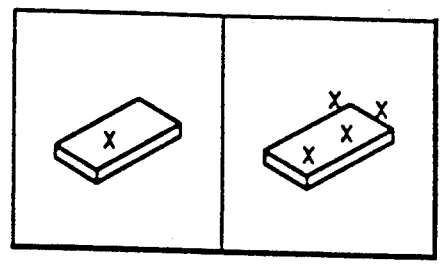
FIG. 5 shows the test stimuli of FIG. 4 with lookpoints superimposed thereon.

FIGS. 4 and 5 shows a comparison test. The left side of the screen shows a new package of one design and the right side shows the new package of a second design. When tested, the subject found the package of the second design more interesting and would normally be the design selected.

The invention has been described herein and the appendix included with the specification completes the disclosure. The invention provides a flexible, inexpensive, user-friendly apparatus and method that can be used as a basic platform or engine for testing and experimenting with a wide variety of psychophysiological reactions to visual stimuli which may be augmented with other sensory information such as sound. Many embodiments may be created using the invention and it is to be understood that such embodiments and modifications can be created without departing from the spirit and scope of the claims below.

APPENDIX

This appendix contains a listing of the software usable in the present invention and includes an introductory user's guide.

This appendix is hereby incorporated in and made a part of the specification of said invention. Any and all copyrights relating to this appendix except those necessary for fulfilling any patent law or rule requirements are retained by owners.

Part 1: Introduction

ERICA stands for Eyegaze Response Interface Computer Aid. The ERICA system is an eye gaze computing system which estimates where a user or subject is looking and measures pupil diameter. It can also be used to identify eye blinks. The setup of the system is shown in Figure 1 below.

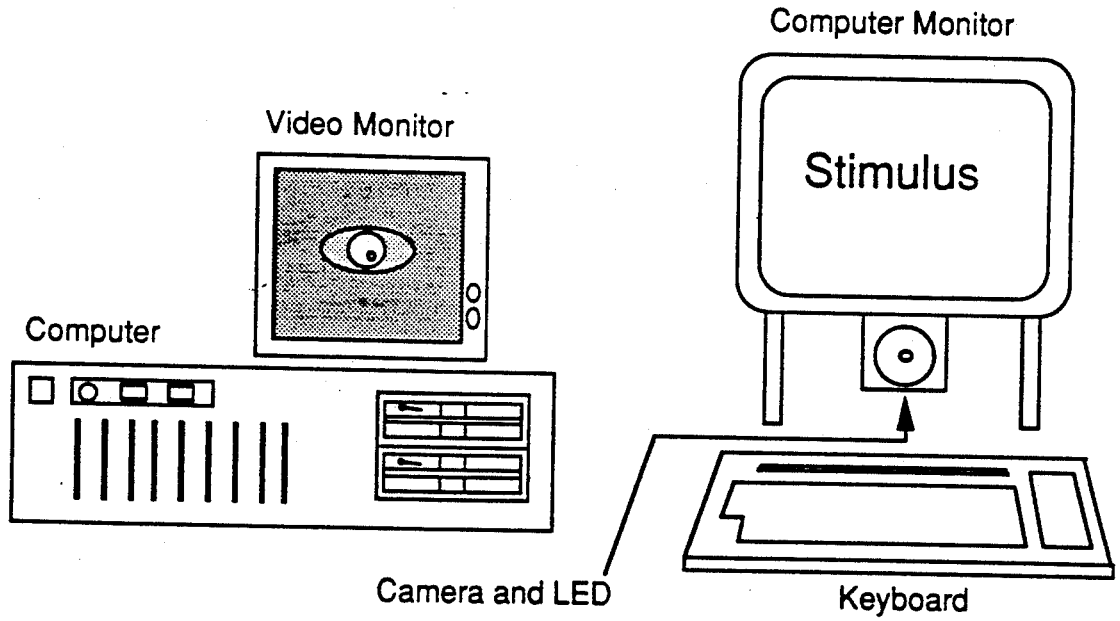

A variety of applications have already been considered for this technology. Among these are visual scanning patterns, visual acuity, and mental workload. The purpose of this manual is to explain the use of the software written to analyze visual scanning patterns (also called *saccadic* eye movements) and pupillary responses to visual stimuli. Part 2 describes the requirements of the ERICA system and how the system measures eye behavior. Part 3 describes the purpose of the software, providing an overview of its functions and capabilities. Part 4 describes how to create psychological test stimuli. Part 5 describes how to define important areas of stimuli and how to combine stimuli into executable tests. Part 6 explains how to register subjects for and how to run these tests. Finally, Part 7 provides explanation of how to analyze and interpret the results of the tests.

System requirements

*Hardware:*

In order to use the ERICA psychological testing software, you need the following hardware:

1) An IBM or IBM-compatible personal computer with an MS/DOS operating environment and at least 1 megabyte of hard disk space..
2) An EGA (or better) graphics monitor.
3) A keyboard and mouse.
4) A video surveillance camera, e.g. Sanyo VD360
5) A framegrabber board, e.g. Imaging Technology's PCVision Plus framegrabber
6) A light emitting diode (LED)
7) A black and white video monitor

*Installation of Software*

Before copying the files into the computer, the following directories must be created on your hard drive:

SACCADE
SACCADE\BATCH
SACCADE\BOX
SACCADE\PICTURES
SACCADE\RESULTS
SACCADE\TEXT

Using the make directory, change directory, and copy commands, all of the software contained on your floppy disk (usually in the A or B drive) can be installed. In order to create these directories, at the MS\DOS prompt (a greater than sign >), type the following sequence of commands, pressing the "Return" or "Enter" key in between commands. The prompt will appear every time you press either of those keys.

> cd\
> md saccade
> cd saccade
> md batch

```
> md box
> md pictures
> md results
> md text
```

Now to copy all of the files into the appropriate directories, enter the following sequence of commands:

```
> a:
```
(If your floppy drive is B, type b:)
```
> copy *.btc c:\saccade\batch
```
(The c: on this line indicates that the hard drive you will be working with is the C drive. If it is D, you would use d:, etc.

Similarly, in the following commands, use the appropriate letter for the drive you are working with)

```
> copy *.box c:\saccade\box
> copy *.pic c:\saccade\pictures
> copy *.res c:\saccade\results
> copy *.txt c:\saccade\text
> copy *.exe c:\saccade
> c:
> cd\saccade
```

The main executable files are called SACCADE.EXE and SANALYZE.EXE.

How the system operates:

Figure 2 illustrates a hardware configuration of the system. An infrared light emitting diode (LED) is mounted on the center of the camera lens. As this light shines on the user's face three basic types of reflections occur. The camera captures these reflected images every 30 milliseconds. The light reflecting off the face looks relatively dark compared to the light reflections off the eyes. One reflection, known as the *glint* comes from light reflecting off the corneal surface of the eye. It looks like a very small and bright dot. The larger, but somewhat less intense reflection is known as the *bright eye*, a reflection of light which has entered the pupil, bounced off the retinal surface, and passed back out through the pupil.

When these images are passed by the camera to the framegrabber they are *digitized*, that is the intensities of the different reflections are converted to numbers. Each digitized image is routed from the framegrabber to the *gaze routines*. It is the gaze routines which use the differences in light intensities to locate the user's eye in the image. They use the relative positions of the glint and the bright eye to measure each *lookpoint*, an x-y coordinate indicating where someone is looking in the area around the camera. The diameter of the circular bright eye is interpreted as the pupil diameter, and a quick decrease and increase in this diameter is identified as an eyeblink. The x-y coordinates represent graphics coordinates on the computer screen. Pupil diameter is measured in terms of the number of pixels in the image counted along a diameter of the bright eye. During these different eye movements, the video monitor shows the relative positions and sizes of the bright eye and glint as shown below.

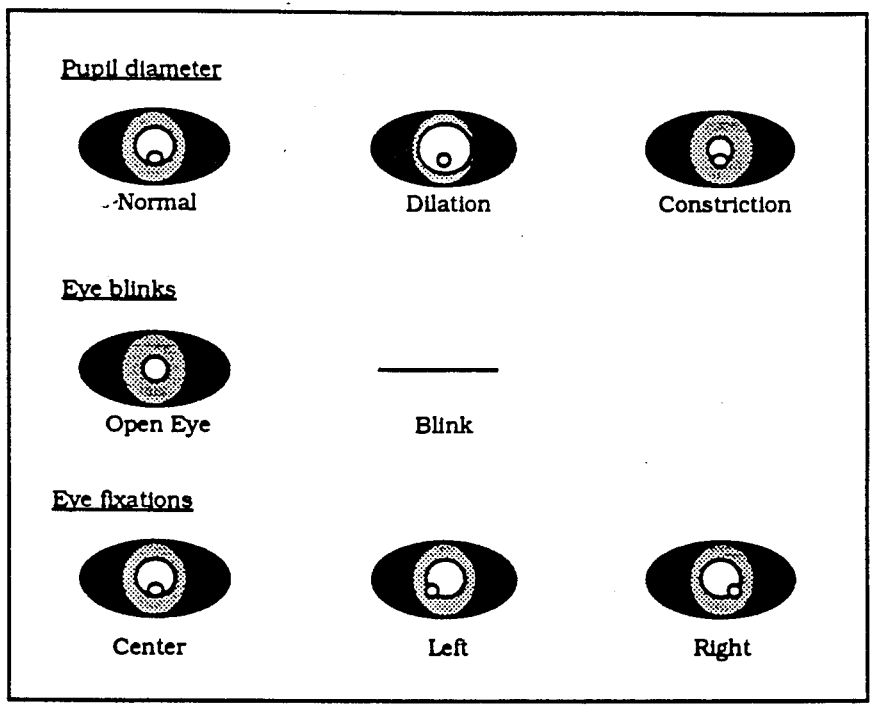

Part 3: Introduction to the Software

The purpose of this psychological software is to provide a means of investigating scanning patterns and preferences of images and text. The software allows you to
1) Create stimuli in textual and graphics form
2) Combine stimuli in any number of ways into a batch test
3) Define important areas of interest on stimulus screens
4) Run a batch test
5) Review raw and summarized data in written and graphic form
6) Write summarized results to a DOS file, LOTUS file, or printer From the creation of the stimuli and test to the compilation and reduction of the results, an example will be used to demonstrate the software.

*Starting the program*

In order to run the main executable software, you would enter the SACCADE directory and type in the name of the executable file (filename ends in .EXE) at the MS\DOS prompt. For example, to run the saccade results file writing program (SANALYZE.EXE), you would type > cd\saccade    (not necessary if you are already in the saccade directory)
> sanalyze For right now, however, it is necessary to create and run a complete test from scratch. The SACCADE.EXE executable file provides these options. So type

```
> cd\saccade
> saccade
```

At this point the screen should be blue with a white menu in the center. The line on the top left indicates the name of the menu. The line on the top right beginning "Coreleft = " indicates how much dynamic memory is left in the computer to use during the program. Memory will be used by the program when loading in graphics, reading in results files, etc. At such times this memory would decrease.

The bottom line of the screen tells you if there are any messages (there should not be any right now).

You should be looking at the Main Menu of the program.

The following choices (with their functions in parentheses) are listed in the Main Menu :

| | |
|---|---|
| Digitize and Store an Image | *(Creating pictorial stimuli using ERICA's camera)* |
| Generate and Save a Text Screen | *(Creating textual stimuli)* |
| Register a Subject | *(Entering information about the subject to be tested)* |
| Perform saccadic motion test | *(Creating and running tests on subjects)* |
| Analyze Results | *(Looking at results of tests)* |
| Quit | *(Exiting the saccade program back to DOS)* |

*Selecting Options*

Notice that using the left, right, up, and down cursor arrows on the keyboard move the red bar which highlights the current menu choice. A menu choice can be selected either by pressing the <enter> key when the bar is highlighting your menu choice or by typing the *hotkey* corresponding to your choice. For example, if you wanted to create textual stimuli to be used later for testing, you would want to select the option "Generate and Save a Text Screen" either by 1) Typing the hotkey T (shown in bold face in the manual, and in yellow on the screen)

or

2) Pressing return after using the arrows to position the highlight bar over that menu option.

Part 4: Creating Psychological Test Stimuli

*Creating Pictorial Stimuli*

From the Main Menu, select the first option: "Digitize and Store an Image." The Picture Menu should appear with the following options:

| | |
|---|---|
| Grab a Frame | (Take a photo snapshot of object in front of camera) |
| Continuous | (Allow camera to bring in new images) |
| Make image Binary | (Converts images to black and white) |
| Draw the Image on a graphics screen | (View the stimulus as it would appear in the test) |
| Equalize the image | (Increases black/white contrast of the image) |
| Reverse the intensities, Negative | (Produce the inverse of the image) |

Perform image Reduction (Make image smaller)
Average image intensities, smoothing (Reduce contrasts in the image)
BoX on image (Cut image in half)
Load image from disk (View a previously created image)
Save image on disk (Name the image and store it)
Quit (Return to the main menu)

The current version of the psychological testing software allows one type of pictorial stimulus to be displayed: the type which has been created using this menu. (Scanner-created images will be incorporated in later versions). When you first enter this menu, the only available options are "Grab a Frame", "Continuous", "Load image from disk", and "Quit". This is because at the moment there are no pictures are available in the program's memory to work with, and working with an image is what the remaining options are used for.

Loading in images to view (the "Load an image from disk" option)

To view pictures which have already been created, select the "Load image..." option. If any usable images are in the c:\saccade\pictures directory, their names will be listed in the box on the right. Using the cursor arrows, you can select the picture you wish to view (there are no hotkeys for the pictures). As an example, use the arrow keys to highlight the picture entitled farside1. As soon as you press <enter>, the menu screen will disappear and on the left side of the screen, you should see a picture from "The Far Side" comic strip. Pressing any key will return you to the Picture Menu. Similarly, you can select this option as often as you like in order to view the images you have available. (Note: At this moment there is no option for working with pictures already saved on the disk. A later version should allow for this option as well).

Taking Pictures (the "Continuous" and "Grab a Frame" options)

In order to create your own image, the framegrabber must be able to receive images from the camera. To check if the framegrabber is already in *continuous* mode (meaning it is continuously receiving pictures), place your hand about twenty centimeters in front of the camera and move it around. If the image on the black-and-white monitor remains still, the framegrabber is not in continuous mode. Select the "Continuous" option to get into this mode. This option releases any grabbed frames in the framegrabber and enters continuous imaging mode.

Choose something small that you want to take a picture of: your hand, your face, a newspaper clipping, a magazine photo, etc. Move it back and forth in front of the camera until the image in the black-and-white monitor is as large and focused as you want. For big objects, this may require unscrewing the extender lens from the front of the camera. When you have the object where you want it, select the first option "Grab a Frame", which tells the framegrabber to hold the current image coming in from the camera. If at this moment, the image on the black-and-white screen is not as you wanted, go into continuous mode again and grab a frame as described before until the image on the screen is as you would like it. This is the image to be worked with.

Viewing Pictures (the "Draw an image on the graphics screen" option)

To see how this image would look in a test, choose "Draw the image...". The program will ask if you wish to see the Reduced or Full-Sized image. Select Full-Size for now. The image should appear on the graphics screen in different shades of blue. It is likely that the image has not come out in graphics mode as well as desired. That is why the image processing choices are available at this time. Press a key to return to the Picture Menu.

*Improving pictures through post-processing*
The "Equalize the image" and "Average image intensities, smoothing" options Generally, the image will come out much better after you equalize it. Watch the image on the black-and-white video monitor as you select the "Equalize the image" option. In effect, this function performs contrast enhancement and allows for greater separation in the drawing on the graphics screen. When the yellow bar on the computer monitor moves to 100 % the image has been full equalized. Try the "Draw the image..." option again; first view it "Reduced" and then choose the "Draw the image..." option again to see it "Full-sized".

The Full-Size image is larger and rougher looking then the Reduced version. If you are interested in saving a Full-sized image, you might want to use the "Average image intensities, smoothing" option which will make the graph look less rough. You can smooth the image as many times as you wish. It is advisable to view the image after every smoothing (or after any image processing) just to make sure you have done all you want to the image. Every time you smooth or equalize your image, you cannot get back the previous version of the image.

The "Make image Binary" and "Reverse the intensities (Negative)" options

Two of the processing options which may be of interest are "Make image Binary" and "Reverse the intensities...". The first is also an option which is irreversible. It will take each *pixel* (or point) in the image and make it either black or white, depending on which is more similar. This option is good for newspaper clippings, coloring book pictures, and other pictures for which shading is not of interest. In essence, it is good for cleaning up line drawings held in front of the camera. Reversing the intensities is a reversible option, so you can try it on your current picture (twice to get back the original image). In general, it makes lighter pixels darker, and darker pixels lighter. In other words, it negates the images.

Saving your work (the "Save image on disk" option)

Once you have created an image you would like to keep, select "Save image...". You will be asked to enter the name of the file. Enter a name which is at most eight characters in length, hopefully something which will describe the picture. After pressing <enter> describe the picture in further detail if you wish (no more then 60 characters, however). Finally the program will ask if you wish to save the enlarged or reduced version. Think about how you want to use this picture in testing, and how it will look in either size. If you want the picture to take up an entire screen during testing, select "Enlarged." If you want the picture to show up only about half the screen, choose "Reduced."

Congratulations, you have created your first test stimulus. Using "Continuous", "Grab a Frame", "Equalize", the desired image processing options, and "Save image on disk", you can create an entire library of pictorial stimuli to be used for psychological testing.

When you are finished creating pictorial stimuli, choose the "Quit" option to return to the Main Menu.

*Creating Textual Stimuli*

From the Main Menu, select the option entitled "Generate and Save a Text Screen". You will be presented with a screen for text entry. The text on the screen can be entered in any format with any mix of colors desired. To use this selection, just move the cursor to the position at which you would like to enter text and type. The arrow keys move the cursor around. It performs much like a typewriter in that there is no wrap around, etc.

Part 5: Creating Tests

Before creating batch files which will run tests, it is first necessary to define which areas of the images you are interested in analyzing (at least current areas of interest). The idea here is to set up the screen the same way you would have it in a test. Looking at the screen, you would then define boxes which surround different regions of the screen. After the test is run, the analysis portion of the software indicates how many times the subject looked at the specified regions, what the average diameter of the pupil was as the user gazed into that region, and the variance of the pupil diameter. Eventually, the analysis will also include information about duration of gaze within each box, time between lookpoints in the box, etc. The analysis options will be described further in Part 7. For now, we will create a new box file and a batch test file.

The simplest way to learn this is by example. Let's suppose you have at least three pictures: the reduced version of farside1.pic, a reduced size picture which you have created, and the enlarged size picture ccmickey.pic. Suppose you also have a text file called fred.txt. The enlarged picture and the text will each take up full screens, so you cannot compare them with other stimuli simultaneously. You wish to run a test on the subject to determine:

1) How much he prefers your picture to the farside1 picture
2) The subject's reaction to the textual stimuli in fred.txt and
3) The subject's reaction to the large picture of Mickey Mouse.

You would want to create a test which will display these three screens in that sequence. Furthermore, you may also want to know:

1) How often does the subject look at the caption under the Far Side cartoon?

2) How often does the subject look at Mickey's eyes?

For this sort of analysis you also need to create a box file. The box file specifies areas of interest on a screen.

Defining Areas of Interest on the Screen

From the Main Menu select the "Execute picture/test batch file" option which will bring you to the Test Menu. There are a number of options in this menu. Select the option entitled "Define Important areas of images".

The directory listing of pictures will appear on the right side of the screen. Now, remembering the test you are planning on creating (it is helpful to have it written down in front of you), the first stimulus screen should contain two reduced size pictures: a picture of the Far Side cartoon on the left, and on the right, the picture of your choice (one you have created yourself, one which is already provided, or the farside1 picture again). Because you want the Far Side picture on the left, you choose that first by pressing <enter> when the bar is over that name.

*At this point (because of the version you own) you might be asked if the picture is active or inactive... it does not matter what you choose. Choose active for now.*

Next the program will ask for another picture. If you do not want another picture in that stimulus screen, press <ESC> at this time; otherwise, position the bar over the reduced size picture of your choice and select that picture.

The graphics screen will now appear with the Far Side picture on the bottom left and the other picture on the bottom right. On the top third of the screen is the menu for box definitions. This is the menu which will allow you to define the screen areas you are interested in analyzing. The menu choices are:

| | | |
|---|---|---|
| Remove a box | Save a box file | Edit a box file, |
| Define a box | View a box | Quit |

As indicated by the white message below this menu, the menu choices can be activated by 1) typing the number written in each menu box 2) typing the letter with which a menu choice begins or 3) by using the left button on the mouse.

IF you do not see a mouse cursor on the screen you cannot *create* or *edit* box definitions from within this program. "Quit" out of the entire program and make sure your mouse is active and connected.

View a Box

Click on this option. A strip of 15 boxes appears. Under the strip is a request for you to enter the number of the box you wish to view. You can enter the box number by clicking the mouse over it or by typing the character in the box. If you have decided that you no longer want to define a box, you can press '0' or 'Q' or <ESC> to avoid viewing a box.

For our example, select box 1. You should hear a beep and see a message indicating that box 1 is not defined. Click the mouse or press a key to continue. The point of making this mistake first was to learn that boxes must somehow be defined before they can be viewed. You can define them either by calling up a box file which already contains box definitions (the Edit box file command) or by defining a box for a given number. Try viewing other boxes... you should get the same error message.

If a box is actually defined, a yellow box will appear on the screen. The yellow boundary outlines an area of interest which the user has defined.

*Define a Box*

You may be wondering how a box is defined, and what is involved in the definition. Simply enough, to define a box, you need only mark the upper left and bottom right corners of the area you are interested in. Although the description for defining a box appears lengthy, it actually consists of three simple steps:

Step 1) Indicate which box you wish to define

Step 2) Click on the upper left corner of the region of interest

Step 3) Click on the bottom right corner of the region of interest

Click on the "Define a Box" option. A strip of 15 boxes appears. Under the strip is a request for you to enter the number of the box you wish to define. You can enter the box number by clicking the mouse over it or by typing the character in the box. If you have decided that you no longer want to define a box, you can press '0' or 'Q' or <ESC> to avoid defining a box.

For our example, choose to define box number 1. The white message will then ask you to define the upper left corner of the box. Position the mouse cursor such that the pointed end of the arrow is at the upper left corner of your region of interest. Click the mouse button when you are at this point (remember to use the left button). A small cross appears at the center of the upper left corner. Also, a message appears asking you to define the bottom right corner. Define this corner the same way (positioning the mouse cursor and then clicking the button).

If you have not defined the bottom right corner further down and right of the upper left, you will get a message asking you to define the box. It is actually useful to misplace the bottom right corner if the cross showing the upper right corner is not where you want it to be. That way you can redefine your box.

If you have defined a box properly, the box appears on the screen, outlining the image. In the message area, you will see the coordinates ulx, uly, brx, and bry. These are the x and y graphics screen coordinates of the upper left and bottom right corners of the box you have defined. Click the mouse again to remove the box from the screen. The program now knows the coordinates for box 1. If you use the "View a Box" option now, you would not get an error message for box 1. However, you would still get the error for undefined boxes.

Continuing with the "Define a Box" option you can create a set of up to 15 boxes defining important areas of the computer screen.

*Save a Box File*

After making definitions you will need to store them in the c:\saccade\box directory on the computer. Select the menu's "Save a box file" option. A message will ask you to enter the name of the file under which these definitions are to be saved. You can use any letters or numbers for the filename. You can also use the backspace key to erase typing errors. Press the return key when you have typed in the filename. The program will save the definitions under the name. The file containing these definitions can now be used for tests.

*Erasing box definitions*

A box definition can be removed in one of two ways:
1) Using the "Define a Box" option to redefine a previously defined box
   This option is better if you actually need to redefine the area of interest.
2) Using the "Remove a Box" option to remove from the program's memory,
   a previously defined box. This is better if you do not want to associate a
   region of interest with the number of the box you choose to remove.

To "Remove a Box" you need only select this option and then click on the number of the box you wish to erase. If the box is not defined anyway, a message will indicate that you have really done nothing by trying to erase a box definition which does not exist. If the box is defined, the program displays the box on the screen so you can see what you are erasing. Hopefully, you will have viewed the box before deciding to delete it. When the program displays the box to be removed, click the mouse and the definition will be erased.

*Editing a box file*

In some ways, this is one of the most powerful features of the box files. Supposing you run a test and you view the results based on some box file definitions. What if you find that a lot of the lookpoints are in a certain area, an area which you did not define in the box file? By reloading the box file and editing it, you can redefine the areas which you are interested in. If you have only defined about ten of the possible fifteen boxes, you could use the remaining five slots to define the areas which you now find interesting. Also, you could remove some box definitions, and make them larger or smaller, depending on where your interests lie.

Calling up a box file for editing is similar to the save option. Selecting the "Edit a box file" option, type in the name of the file you wish to edit. If it exists, you will be able to work with the definitions it contains.

*Creating a batch test file*

From the Main Menu, select the third option: "Perform saccadic motion test." The Test Menu should appear with the following options:

| | |
|---|---|
| Define Important areas of image | (Use pictures to create box files) |
| Create a batch test | (Make test with pictorial and textual stimuli) |
| Edit batch file | (Change names of results files for a batch test) |
| Test configure | (Change testing parameters) |
| Perform a single test | (Create and run a test for one stimulus screen) |
| Execute a picture test Batch file | (Run a batch test) |
| Quit | (Return to the Main menu) |

The first three options listed above allow you to choose the pictures and text you wish to display in a test and change the name of the files which the results are written to.

*Perform a single test*

This option allows you to test saccadic motion for a single stimulus screen. It performs a test with text, one enlarged picture, or two reduced-size pictures. If you select this option, the program will request a list of file names to be used in the test. The program will also ask for a file name to store the results in and for a box file to process the results with. You must enter a results file name, the box file name is optional. When the user is ready he/she or the experimenter can press a key to begin the test. The program will perform a calibration and display the selected image(s) or text screen. The program will grab and store lookpoints until either the desired number of lookpoints have been taken or a key is pressed.

*Create a batch test*

This is the standard option to use in creating a test which includes more than one stimulus screen. You can create a batch file to execute later as many times as you wish. The user is presented with a screen to enter a list of files to be displayed, enter the name of the results file, and enter the name of the corresponding box file (for analysis). After each screen is filled in, a new one will be presented. As many tests as desired can be included into a batch file. To end the batch file just leave the filename at the first prompt blank and press return.

*Edit batch file*

The last option mentioned that you could create a batch file to be executed as many times as you wished. But recalling that when the batch file was created, the results files had to be specified, every time the batch test is run, the results from the previous running of the test will be erased and written over. This becomes a real problem when many subjects are to be tested on the same set of stimuli using the same batch test. One way to avoid this hassle is to recreate the batch test for each subject and give different names for the results filed for that subject. Another way is to exit the program, enter the c:\saccade\results directory and rename the old results files before they are written over. Both of these methods are clearly tedious and time consuming.

This option saves you the trouble of trying to rename your batch files by doing it for you. When you select this option, you will be prompted to select a batch file. Once you make a selection, you can input a 5-character seed which will be used in modifying the results files used by the batch file. The new results files are constructed as follows: seed000.res, seed001.res, seed002.res, etc. up to the number of screens in the batch test. By using this option, you can input the subject's name, number, or other relevant data as the 5-character seed so that later you will be able to distinguish the results files for different test cases.

Part 6: Running Tests

Registering the subject

From the Main Menu, select the fifth option: "Register a subject." This option simply allows you to enter information about the subject: their name, number, and any other information of interest. The information of interest cannot take up more than 80 characters. Although it is not necessary to register a subject, it may come in useful, when analyzing results, to know whose eye behavior data you are evaluating. The analyze results section of the software will often display information about the subject if it is available in the results file. By registering information about the subject to be tested before the test, this information will be included in the results files created by running a test on the subject.

Configuring the test environment

This option is particularly important in terms of making a test compatible with the subject. If, for example, you have found from previous tests that a particular calibration does not work well for a subject or that you would like to gather more or less data points in your tests, this is the option to use to make such alterations. Also, when you quit the program, any changes you have made in terms of configuring the test environment will be stored in the file CONFIG.CAL and reused when the program is run again.

From the Test Menu, when you select the "Test configure" option you will see a screen with information that looks quite puzzling. The screen will have the following configure options in the left column followed by their value in parentheses:

*Number of Calibration points*     Choices are 4, 5, and 8, the default is 4. The more points used in the calibration before the test, the more accurately the software can estimate lookpoints. The tradeoff is that it is more difficult to calibrate with more points.

*Number of Filter points*     The upper limit is 5, the default value is 1. When gathering lookpoints, the software gets as many lookpoints as there are filter points, and then averages the lookpoints to come up with one point. The more filter points used, the smoother the data. The tradeoff is that the software gathers data slower as the number of filter points increases.

*Active box lookpoint feedback*     This can be either On or Off, the default is On. The idea behind this is that during a test, the software has the ability to place a small circle at the point where it thinks the subject is looking. This is an excellent means of seeing how accurate the program is in determining lookpoints. In cases where you do think the user may be distracted by the feedback cursor, you should have this option turned Off.

Recall that when the test is created, after a picture is chosen, the user is asked whether the image is active or not. This active box idea is actually a remnant of an older version of the program in which if a subject looks at an active image a certain number of times, the program goes on to the next stimulus screen. At this point, such processing can be done on any part of the image, and so the active/inactive boxes are really unnecessary. Still, the idea behind the active box feedback is that you can choose if the feedback cursor appears when the subject is looking at the image. Similarly, the *inactive* box lookpoint feedback, when turned On, allows you to see where the subject is looking when they are looking at an inactive portion of the screen (either an inactive image or the screen's background).

*Inactive box lookpoint feedback*     This can be either On or Off, the default is On. See the "Active box lookpoint feedback" option for more explanation.

*Active boxes status*     This can be either On or Off as well, the default is Off. If it is On, then if the software collects X lookpoints within a certain box (X is defined by the option "Number of lookpoints to select box"). This option could be useful when you are experimenting with interactive images -- the screen could change from one stimulus screen to the next if the subject looks at a specific region a certain number of times.

*Number of lookpoints to select box*     The range is from 1 to 32000; this option is useless if "Active boxes status" is Off. See active boxes status for further explanation. Also, note that if the number of lookpoints required to select a box is greater than the *Total number of lookpoints allowed* per stimulus screen, then this option will be ineffective.

*Total number of lookpoints allowed*     The range is from 1 to 32000. The default is at 250 lookpoints taken per stimulus screen. If the software is sampling well (about 30 samples per second), then each screen will be displayed for about 8 seconds. 900 lookpoints take about 30 seconds to gather. Also, note that the software takes slightly more time to gather lookpoints if the feedback cursor's are On.

*Number of screens between calibration*     The range is between 0 and 4, the defaults is 0. This indicates how many stimulus screens will be presented before the program perform a another calibration on the subject's eye. By introducing a calibration after a specified number of screens, the experiment can better estimate the subject's lookpoints if the subject has moved, and it can provide a change of pace from the monotony of staring at stimulus screens. An animated calibration that runs every few screens may be quite useful, in fact, for testing infants. When this option is set to 0, only one calibration is performed -- at the beginning of the test.

*Performing a test*

As described earlier the *"Perform a single test"* option allows you to create and run a test in one step -- except the test must be for only one screen. The option for longer tests is *"Execute a picture test batch file."* This name may be misleading in that implies only pictures can be used in the test. In fact, the option actually allows you to select a previously created batch file, and as you may recall, a batch file can contain both pictures and text as stimuli.

The testing step is very simple. When the option is selected, a batch file must be selected to be run. You can press ESCAPE if you decide not to make a selection. If you do choose a test to run, the screen will go black and a message will appear in the center: "Press any key to begin test." Get the subject situated comfortably in front of the camera so that his/her eye appears focused on the video monitor. You may also want to adjust the F-stop on the camera in order to enhance the contrasts between their bright eye, glint, and face. Press the key to begin, or let them press it.

The program will first perform a calibration with the number of points you chose in the *Test Configure* menu. If the calibration is animated, a turtle will travel from one calibration point to the next (perhaps with noise), and a smiley face will flash at each point. If the calibration is normal, a bullseye will appear at each calibration point. The subject should stare at each calibration point as it is identified by the smiley face or the bullseye. It is also helpful if the subject does not move around or blink during calibration. If the calibration is bad, the program will indicate this and try again until it works. If the program continues to get only bad calibrations, you must stop the program by pressing CTRL-C twice. If the calibration is good, the program will continue with the test stimuli.

As the test is running, if a test stalls on one screen for too long, it may be that the software is having trouble finding the subject's eye. Pressing a key will terminate the stimulus screen and allow the software go on to the next stimulus screen.

Part 7: Analyzing Results

In order to analyze the results of a test, you can either use the "Analyze results" option in the saccade.exe program or use the sanalyze.exe program. The first choice allows you to look at the results in graphical and textual form in several different ways. The second option, only providing textual summaries of the results, writes the results to a DOS file which can be analyzed later using other post-processing programs.

It is easier to understand the use and limits of the sanalyze.exe program once you understand the rest of the saccade.exe program.

Analysis using saccade.exe

From the Main Menu, select the fourth option: "Analyze results." The Analysis Menu should appear with the following options:

| | |
|---|---|
| Set File Specification | (Use * and ? to load results files) |
| Get New results file for analysis | (Load in a new results file) |
| List results on screen | (Lists each data point in current results file) |
| Superimpose lookpoints over images | (Change names of results files for a batch test) |
| Graphical summary of results | (Graphs x and y lookpoints, and horizontal and vertical pupil diameters for each data point in current results file) |
| Information Summary of results | (Summarizes data in current results file) |
| Analyze results using Box definitions | (Use box files to summarize results information over user-defined areas of interest) |
| Quit | (Return to the Main menu) |

Loading a results file

In order to view the results of the tests, it is first necessary to load the results into memory. If you choose the option, "Get New results file for analysis," the program checks for results files corresponding to the pathname saccade\results\*.res. If you want to load results files which have extensions other than ".res" or which are located in other directories, you must specify the corresponding pathname using the option entitled "Set File Specification."

For example, suppose you saved results files in the saccade\results directory with the same file name but different extensions (e.g. result.1 result.2 result.3). You would set the file specification as "result.*". Suppose these files were located in another directory called myresults\part1, then you would ues the file specification "\myresults\part1\result.*".

Once you have set the appropriate file specification and chosen the option "Get New results file for analysis," the program presents, in alphabetical order, a list of the results files corresponding to the pathname you have chosen. You can select only one file from the list provided. Use the arrow keys to move the highlight bar over the desired results file, and then press return to load that file.

Simple options
List results on screen

This option is very basic. It lists the raw data on the screen ten data points at a time until it reaches the end of the file. You must press a key in between each set of ten data points in order to see the subsequent set of points. Each listed data point contains 4 pieces of information: the x-coordinate and y-coordinate of the subject's eyegaze, the horizontal pupil diameter, and the time at which the data was taken.

The x- and y-coordinates are based on the resolution of the screen (specified by a function called set_gaze_res). This means that if the resolution screen was specified as an 80 by 25 (80 horizontally by 25 vertically), then if the person were staring directly at the center of the computer screen, the x- and y-coordinates would be 40 and 13 (12.5 rounded up), respectively. The pupil diameter is in terms of pixels on the framegrabber. These measures have not totally accounted for changes in diameter resulting from head motion. Therefore, when you compare diameters from data point to data point, you should consider only the relative change in the measure and not the absolute change. Finally, the time stamp is given in milliseconds. The time stamp starts from zero at the beginning of each stimulus screen.

*Superimpose lookpoints over image*

This option places on the screen the image which was presented to the subject when the data was recorded. For each data point, a tiny circle is placed over the image at a point corresponding to the x- and y-coordinates of the subject's lookpoint. In the bottom left corner of the screen is a large circle whose diameter is the same as the horizontal pupil diameter for that data point. The diameter of the circle is also written inside the circle. The succeeding lookpoints will be shown either automatically ("Continuous lookpoint display") or through subsequent keystrokes ("Wait for key between lookpoints"), depending on which option you choose immediately after you select "Superimpose lookpoints over images." Anytime while the lookpoints are being displayed, you can type 'Q' to stop the display and return to the Analysis Menu.

NOTE: If a picture does not appear on the screen where it should be, the program was unable to find it in the directory in which it should be located. If you wish to see the picture, you must place it in that directory. It is likely that this directory is the \saccade\pictures directory.

*Graphical summary of results*

This option is a small step above the previous two. It provides for a complete display of the test results. When the option "Graphical summary of results" is selected, a graphics screen appears. The bottom left corner identifies the subject who was tested and describes the image that was on the screen during testing. If there were two pictures on the screen, for example, then the first picture listed is the name of the picture on the left and the second is the name of the picture on the right.

The other three boxes on the screen contain graphs. If there were 250 data points gathered during the test, then the horizontal axis of each graph should begin with 1 and end with 250. (The horizontal axis will later be change to a time axis, since the time interval between sequential data points is not constant). As indicated by the titles of the graphs, the graphs show the complete set of x-coordinates and y-coordinates for each lookpoint, and they show both the horizontal and vertical pupil diameters for each data point.

Analyzing lookpoints

The labels of the vertical axis of the x-coordinate graph are based on the horizontal resolution of the graphics or text screen used during the test. For example, since an EGA high-resolution graphics screen has 640 horizontal pixels for the graphics screen, the vertical axis for the x-coordinates ranges from 1 to 640. Similarly, the labels of the vertical axis of the y-coordinate graph are based on the vertical resolution of the stimulus screen. On each graph you can see how the subject's horizontal and vertical gaze changed as the total number of data points (e.g. 250) were taken. For instance, if the graph on the x-coordinate always ranges in the upper half of the screen, the behavior indicates that the individual preferred to look at the right side of the image screen.

Analyzing diameters and blinks

The graph in the bottom right corner of the screen shows the change in horizontal and vertical pupil diameters as the subject looks at the stimulus. Notice that in the beginning there is a sharp drop in both diameters because the subject's eye initially constricts in reaction to the brightness of the stimulus. Also, eye blinks can be identified by a near vertical drop in the vertical pupil diameter.

*Information summary of results*

When you select this option, the first screen which appears displays information about the subject and about the stimulus screen. This information includes the subject's name and number as well as other relevant information which was entered before the subject took the test. It also includes the name of the text file which was used or the names of the pictures which were displayed during the test. Below this information is a brief statistical summary of the entire test. It contains the following information:

1) Total number of lookpoints, $n$
2) Mean horizontal pupil diameter, $\mu$
3) Sum of all horizontal pupil diameters
4) Sum of all squared horizontal pupil diameters
5) Standard deviation of horizontal pupil diameters, $s$ The most important of these measures are the first two and the last statistical measure. The first is significant in that it tells you how many lookpoints were gathered in all. The second measure provides a basis for comparison with other stimulus screens. The average pupillary response to the stimulus screen can be compared with the level of pupillary arousal elicited by other stimulus screens. This measure is not significant in itself, but is instead, a basis for comparison. Similarly, the standard deviation provides an idea of how much the pupillary response varied for that stimulus screen. This may provide a basis for determining which stimuli cause more pupillary activity to occur.

Sometimes you may be interested in comparing different images within one screen. For example, you may wish to see if somebody prefers to look at one picture more than another or if one image cause more pupillary activity than does the other image on that same screen. For this reason, this option also provides a summary of each images in the screen. Pressing any key, you will see the screen change to reveal the same statistical summary information as on the previous screen. If the value of $n$ on the previous screen was 250, meaning that a total of 250 data points were taken, you will see that these 250 points have been divided up among the different images which were on the screen. For instance, there may be 125 lookpoints for the first picture, 100 for the second picture, and 25 lookpoints outside both of the pictures. This would indicate that the subject looked at the picture on the left more often than the picture on the right and looked overall at the pictures more often than not. Similar comparisons could be made with the average pupil diameter measures and with the standard deviations. If you press a key again, you will be returned to the Analysis menu screen.

*Analyze results using box definitions*

Using the same line of reasoning as with the information summary, the analysis may be concerned with even more specific parts of a stimulus screen than the images as a whole. For example, you may wish to see how long the subject looks at the caption on a Far Side cartoon or how often he looks at the eyes in the picture of a face. This is where the box files come in useful. Selecting the option "Analyze results using box definitions" you will be presented with a small box definition menu.

On the bottom right corner of the screen, you will see the name of the box file which you chose to analyze the stimulus screen with. If there is no file name in that corner, you must have pressed the Escape key when asked to choose a box file for the screen (This is when you were creating the batch test to run on subjects). If there is no box file associated with your results file, you can always use the option "Load new box file" to load a file to use in the analysis.

There are two advantages to the "Load new box file" option. First, as mentioned above, suppose you did not choose a box file to associate your results with. Suppose that now you do want a more detailed analysis of your results. You wish to look into specific parts of the images used in the stimulus, you can load in an existing results file so that you can now perform such analyses. Secondly, suppose you have already associated a box file with the stimulus screen and that the box file contains the maximum of fifteen box definitions. If during your analysis, you find that there is still another part of the stimulus screen which you would like to analyze, there is no more room in the box file for another definition. You can place this new definition (and up to 14 more) in a new box file. You could then use the "Load new box file" option to load in the new box file and continue your analysis of the results.

In summary, the "Load new box file" option lets you analyze any rectangular section of the stimulus screen used for your results. If the appropriate sections are not already defined in any of the existing files, you can go back to the option "Define important areas of image" in the Test Menu. There you can add the definition to an existing file or enter it in a new file, return to the "Analyze results using box definitions" option in the Analysis menu, and load up the appropriate results file.

Other than loading in new box files, this menu allows you to view summaries of the results in either text or graphics format. These summaries are the same as those in the "Information summary of results" option in that they describe the number of lookpoints, average pupil diameter, etc. They are different in that each summary describes one of the 15 boxes defined in the box file. Thus, if you choose the text summary option, you will see data summary information for each box defined in the box file. At the bottom of the screen, you should also see a summary for data points "Outside all boxes." These are data points for which the x-y lookpoint was not within the boundaries of any of the boxes defined in the current box file.

Although the advantage of the text summary is that the summaries of all boxes can be seen simultaneously, the problem is that the summary does not show you the box you have defined. This, in fact, is the advantage of the graphics summary. By choosing this option, the stimulus screen will appear as it did during the actual test; however, the upper third of the screen is reserved for the box summary information. A white strip broken into 15 numbered segments appears about one third of the way down from the top of the screen. By clicking the mouse on one of the segments or typing the number of the segment (and pressing return), you can view the summary of the box associated with that number. If the box number you choose is undefined, you will hear a beep and see a message which indicates as such. If the box is defined, the summary information will appear on the top part of the screen and the box will be displayed on the stimulus screen as it was defined.

Analysis using sanalyze.exe

Now that we have seen the various analyses allowed by saccade.exe, it is easier to recognize the need for sanalyze.exe. The program sanalyze.exe is useful for two reasons:
1) Obtaining a printout of the results
2) Performing your own analyses of the results The essence of the sanalyze program is that it converts results from their compressed form in the results file either to a printer readout, to a DOS file, or to a LOTUS spreadsheet file. A file in DOS format can be viewed using a DOS text editor, using the "type <filename>" command at the DOS prompt, or using the "list <filename>" command (if provided) at the DOS prompt. More importantly, the DOS file itself can be printed directly to a printer, called into a word processor for editing, or read in by programs to do additional analyses which the user has in mind. Similarly, the LOTUS spreadsheet file can be imported into LOTUS 1-2-3 or compatible spreadsheet programs in order to gain access to the powerful data manipulation and analysis capabilities of the spreadsheet.

To run the sanalyze.exe program, type "sanalyze" at the DOS prompt. You should then be presented with the following menu:

*Set File Specification*     Set the pathname for selecting results files

| | |
|---|---|
| *Select File(s)* | Load up a single results file or set of results files |
| *Export File(s) for LOTUS* | Write loaded results to a file for use in Lotus 1-2-3 |
| *Generate Report* | Information summary of results -- sent to printer or DOS file |
| *Generate Report by Stimuli* | Summarize results by picture |
| *Set Report Destination* | Destination can be the printer or a DOS file |
| *Configure System* | Set margins for printer |
| *Quit* | Leave the program |

To the right of this menu will be information summarizing the results of the file. This will help you see what activity is going on in the program: which file is currently being loaded or processed, how much memory the program has remaining, etc. When the program generates a report, the report will list all of the lookpoint data, summarize the data for each picture, and summarize the data for the box file associated with the results.

Some of the important facts to remember about this program are

1) You are not limited to loading in one results file at a time

When selecting files, you can press "t" beside all the files you are interested in loading up. This will tag the files you want. Once you press return, only the files which have been tagged (as can be seen by the marker beside the file name) will be loaded up. To untag a file, press "t" again when the selection bar is highlighting the filename. The use of tagged files is important in that over a set of results files, some pictures may be used more than once. The report, if generated using "Generate report," will generate a separate summary for each picture in each of the loaded results files. But the "Generate report by stimuli" option will combine such summaries when the pictures from any of the results file are the same. The results file will appear in the directory from which you ran the sanalyze.exe program.

2) When entering the name of the output file, you may enter the name of an existing file If the file specified as the output file already exists, menu will appear indicating as such. You can go back and reenter the filename, write over the existing file, or append the new summary report to the existing file.

saccade2.prj

```
c:\maryland\fastgaze
c:\ddh\fast\fastfind
c:\cgaze\matfunct
c:\ddh\fast\newfg
c:\ericalib\tools
c:\ericalib\grtools
c:\ericalib\menu
c:\ericalib\moustool
c:\ericalib\timex
c:\maryland\imagebox
c:\maryland\sacboxes
c:\maryland\sacimprc
c:\maryland\sacio
c:\maryland\sacresul
c:\turboc\EGAVGA.obj
c:\maryland\boxdef\032
``` sacimprc.c

```c
include <stdio.h>
#include <stdlib.h>
#include <alloc.h>
#include <dos.h>
#include <math.h>
#include <conio.h>
#include <mem.h>
#include "c:\cgaze\fgroutns.h"
#include "c:\ericalib\tools.h"

typedef unsigned char rowbuf[512];

typedef double rhistarray[256];

/* AUTHOR: Kevin S. Spetz
 * DATE: 9/88
 *
 * Routine to smooth the image in the current video image of the frame
 * grabber. The image is smoothed with a simple averaging filter
 */
void smooth_image(void)
{ int lx,ly;
  unsigned char ave;
  windowtype *buf;
  unsigned char *buf1, *buf2;

buf1 = (unsigned char *) malloc(512 * sizeof(unsigned char));
  buf2 = (unsigned char *) malloc(512 * sizeof(unsigned char));
  if ((buf1 == NULL) || (buf2 == NULL)) {
     fprintf(stderr,"Error! Memory Allocation -- smoothimage");
     exit(1);
  }
  buf = open_window(15,10,65,18,WHITE,CYAN,1,"Status:");
  xycprintf(16,2,WHITE,"Smoothing Image...");
  for (ly = 0; ly < 480; ly++) {
     percentbar(5,5,40,ly,480);
     getrowavw(ly,0,512,buf1);
     getrowavw(ly+1,0,512,buf2);
     for (lx = 0; lx < 511; lx++) {
        ave = (*(buf1 + lx) + *(buf1 + lx + 1) + *(buf2 + lx) + *(buf2 + lx + 1))/4;
        *(buf1 + lx) = *(buf1 + lx + 1) = *(buf2 + lx) = *(buf2 + lx + 1) = ave;
     }
     putrowavw(ly,0,512,buf1);
     putrowavw(ly+1,0,512,buf2);
  }
  percentbar(5,5,40,1,1);
  delay(300);
  close_window(buf);
  free(buf1);  free(buf2);
}

/* AUTHORS: Kevin Spetz, Greg Schubert
 * DATE:
 *
 * Routine to reduce image to 1/4 its original size
 */
void reduce_image(void)
{ int rx,ry,lx,ly,x;
  float ave;
  unsigned char *buf1, *buf2, *abuf;
  windowtype *buf;

buf = open_window(15,10,65,18,WHITE,CYAN,1,"Status:");
  xycprintf(17,2,YELLOW,"Reducing Image...");
  buf1 = (unsigned char *) malloc(512 * sizeof(unsigned char));
  buf2 = (unsigned char *) malloc(512 * sizeof(unsigned char));
  abuf = (unsigned char *) malloc(256 * sizeof(unsigned char));
  memset(abuf,0,256);
``` sacimprc.c

```c
        rx = ry = 0;
        percentbar(5,5,40,0,1);
        for (ly = 0; ly < (480 - 2); ly += 2) {
            getrowavw(ly,0,512,buf1);
            getrowavw(ly+1,0,512,buf2);
        percentbar(5,5,40,ry,240);
        for (lx = 0; lx < (512 - 2); lx += 2) {
            ave = 0;
                for (x = 0; x < 2; x++) {
                    ave += *(buf1 + lx + x);
                    ave += *(buf2 + lx + x);
                    }
                ave = ave / 4.0;
                *(abuf + rx) = (unsigned char) ave;
                rx++;
                }
            putrowavw(ry,0,255,abuf);
            ry++;
            rx = 0;
            }
        percentbar(5,5,40,1,1);
        delay(300);
        free(buf1); free(buf2); free(abuf);
        close_window(buf);
    }

/* AUTHOR: Kevin S. Spetz
 * DATE: 7/88
 *
 * Routine to generate the cumulative distribution function of an image.
 * The image histogram is passed in histarry.  The CDF is returned in
 * rhistarray.  t holds the number of pixels in the image
 */
static void CDF(histarray i, rhistarray c, double t)
    { int index;
        double cum = 0.0;
        for (index = 0; index < 256; index++)
            cum = c[index] = ((double) i[index])/t + cum;
    }

/* AUTHOR: Kevin S. Spetz
 * DATE: 7/88
 *
 * Routine to generate a flat power density function from a cumulative
 * distribution function.
 */
static void flatPDF(rhistarray c, rhistarray m)
    { int index;
        for (index = 0; index < 256; index++)
            m[index] = floor(c[index] * 255.0);
    }

/* AUTHOR: Kevin S. Spetz
 * DATE: 7/88
 *
 * Routine to equalize the image in the current frame-grabber video window.
 * Equalization basically results in contrast enhancement.
 */
void equalize_image(void)
    { histarray image_in;
        rhistarray image_cdf,image_map;
        rowbuf buffer;
        int x,y;
        windowtype *buf;

buf = open_window(15,10,65,18,WHITE,CYAN,1,"Status:");
        xycprintf(13,2,WHITE,"Calculating Histogram...");
        makehistogram(image_in,1,1);
        xycprintf(13,2,YELLOW,"Equalizing Histogram... ");
        percentbar(5,5,40,0,1);
        CDF(image_in,image_cdf,512.0*480.0);
        flatPDF(image_cdf,image_map);
        for (y = 0; y < 480; y++) {
            percentbar(5,5,40,y,480);
            getrowavw(y,0,512,buffer);
            for (x = 0; x < 512; x++)
                buffer[x] = (unsigned char) image_map[(unsigned) buffer[x]];
            putrowavw(y,0,512,buffer);
            }
        percentbar(5,5,40,1,1);
        delay(300);
        close_window(buf);
    }

/* AUTHOR: Kevin S. Spetz
 * DATE: 1/15/89
 *
 * Routine to reverse the intensities in an image.  Basically takes an image
 * and turns it into a negative
 */
``` sacimprc.c

```c
void reverse_image(void)
{   rowbuf buffer;
    int x, y;
    windowtype *buf;

buf = open_window(15,10,65,18,WHITE,CYAN,1,"Status:");
    xycprintf(16,2,WHITE,"Reversing Image...");
    for (y = 0; y < 480; y++) {
        percentbar(5,5,40,y,480);
        getrowavv(y,0,512,buffer);
        for (x = 0; x < 512; x++)
            buffer[x] = 255 - buffer[x];
        putrowavv(y,0,512,buffer);
    }
    percentbar(5,5,40,1,1);
    delay(300);
    close_window(buf);
}

/* AUTHOR: Kevin S. Spetz
 * DATE: 1/15/89
 *
 * Routine to take an image and make it binary. All points below threshold
 * are turned to 0, and all points above are turned to 255.
 */
void binary_image(int threshold)
{   rowbuf buffer;
    int x, y;
    windowtype *buf;

buf = open_window(15,10,65,18,WHITE,CYAN,1,"Status:");
    xycprintf(14,2,WHITE,"Making image binary...");
    for (y = 0; y < 480; y++) {
        percentbar(5,5,40,y,480);
        getrowavv(y,0,512,buffer);
        for (x = 0; x < 512; x++)
            buffer[x] = (buffer[x] < threshold) ? 0 : 255;
        putrowavv(y,0,512,buffer);
    }
    percentbar(5,5,40,1,1);
    delay(300);
    close_window(buf);
}
\032
``` sacboxes.c

```c
include <stdio.h>
include <dos.h>
#include <alloc.h>
#include <stdlib.h>
#include <conio.h>
#include <graphics.h>
#include <ctype.h>
#include <io.h>
#include <time.h>
#include "c:\ericalib\tools.h"
#include "c:\ericalib\moustool.h"
#include "c:\ericalib\timex.h"
#include "c:\cgaze\gaze.h"
#include "c:\maryland\saccade.h"
#include "c:\maryland\sacboxes.h"

static int req_lp = 15;     /* Required number of lookpoints for a selection */
static int boxmark = 1;     /* Box routines will place a yellow icon if in box */
static int noboxmark = 1;   /* Box routines will place a blue icon if not in box */

/* AUTHOR: Kevin S. Spetz
 * DATE 1/31/89
 * Routine that sets the variable for the required number of lookpoints
 * needed to select a box. The lower the number the faster the sytem
 * operates
 */
void set_gaze_speed(int sp)
{   req_lp = sp;
} void set_box_mark(int on)
{   if (on) boxmark = 1;
    else boxmark = 0;
} void set_nobox_mark(int on)
{   if (on) noboxmark = 1;
    else noboxmark = 0;
}
```

```c
activeboxtype *start_activebox(int num, int ulx, int uly, int lrx, int lry)
   { activeboxtype *abl;
      if ((abl = (activeboxtype *) malloc(sizeof(activeboxtype))) == NULL) {
         fprintf(stderr,"Error! Memory Allocation -- start_activebox (GAZE)");
         exit(1);
         }
      abl->num = num;
      abl->ulx = ulx;
      abl->uly = uly;
      abl->lrx = lrx;
      abl->lry = lry;
      abl->enable = 1;
      abl->next = NULL;
      return(abl);
   } void add_activebox(activeboxtype *abl,int num, int ulx, int uly, int lrx, int lry)
   { activeboxtype *tmpb, *t;
      tmpb = abl;
      while(tmpb->next != NULL) {
         tmpb = tmpb->next;
         }
      if ((t = (activeboxtype *) malloc(sizeof(activeboxtype))) == NULL) {
         fprintf(stderr,"Error:  Memory Allocation -- add_activebox (GAZE)");
         exit(1);
         }
      t->next = NULL;
      t->num = num;
      t->ulx = ulx;
      t->uly = uly;
      t->lrx = lrx;
      t->lry = lry;
      t->enable = 1;
      tmpb->next = t;
   } int lookupbox(activeboxtype *abl, int x, int y)
   { activeboxtype *tmpb;
      tmpb = abl;
      while (tmpb != NULL) {
         if ((x > tmpb->ulx) && (x < tmpb->lrx) && (y > tmpb->uly)
            && (y < tmpb->lry) && (tmpb->enable))
            return(tmpb->num);
         tmpb = tmpb->next;
         }
      return(0);
   } void *place_lp(int x, int y, int color)
   { void *s;
      if (screen_mode() == TEXT) {
         s = malloc(2);
         bind(&x,1,80);
         bind(&y,1,25);
         gettext(x,y,x,y,s);
         xycprintf(x,y,color,"1");
         }
      else { setcolor(color);
         bind(&x,3,637);
         bind(&y,3,347);
         s = malloc(imagesize(x - 2, y - 2, x + 2, y + 2));
         getimage(x - 2, y - 2, x + 2, y + 2,s);
         circle(x,y,2);
         setcolor(0);
         circle(x,y,1);
         putpixel(x,y,0);
         }
      return(s);
   } void remove_lp(int x, int y, void *s)
   { if (screen_mode() == TEXT) {
      bind(&x,1,80);
      bind(&y,1,25);
      puttext(x,y,x,y,s);
      free(s);
      }
    else { bind(&x,3,637);
         bind(&y,3,347);
         putimage(x - 2, y - 2,s,COPY_PUT);
         free(s);
         }
   } int getbox(activeboxtype *abl, int *box, int han, unsigned maxlp, int useboxes, float start_time)
   { int index;
      void *s;
      int curbox, prevbox;
      unsigned total_lp = 1;
      int marknext = 0;
      datatype data;
      int ch;
      int x, y , hd, vd;
```

```
/*      mouse_arrow();*/
/*      mouse_on();*/
        if (abl == NULL) useboxes = 0;
        while(!getgazeposition(&x,&y,&hd,&vd)) {
            if (kbhit()) {
                switch(ch = toupper(getch())) {
                    case SPACE : return(0);
                    case RET : marknext = ' '; break;
                    case ESC : return(0);
                    default  : marknext = ch; break;
                }
            }
        }
        if (kbhit()) {
            switch(ch = toupper(getch())) {
                case SPACE : return(0);
                case RET : marknext = ' '; break;
                case ESC : return(0);
                default  : marknext = ch; break;
            }
        }
/* INSERT TIME STAMPING HERE, I THINK */
        data.x = x; data.y = y; data.hd = hd; data.vd = vd;
        data.time= timex() - start_time;
        if (marknext) {
            data.mark = marknext;
            marknext = 0;
        }
        else data.mark = 0;
        _write(han,&data,sizeof(datatype));
        if (screen_mode() != TEXT) {
            data.x *= 8; data.y *= 14;
/*ND mod bind (&x,0,649);*/
            bind (&x,0,639);
            bind(&y,0,349);
        }
        else { bind(&x,0,79);
               bind(&y,0,24);
        }
        if (useboxes) {
            if ((prevbox = lookupbox(abl,x,y))) {
                if (boxmark) {
                    s = place_lp(x,y,YELLOW);
                    delay(20);
                    remove_lp(x,y,s);
                }
            }
            else { if (noboxmark) {
                    s = place_lp(x,y,YELLOW);
                    delay(20);
                    remove_lp(x,y,s);
                }
            }
        }
        else if (noboxmark) {
            s = place_lp(x,y,YELLOW);
            delay(20);
            remove_lp(x,y,s);
        }
        for (index = 0; index < req_lp - 1; index++) {
            while(!getgazeposition(&x,&y,&hd,&vd)) {
                if (kbhit()) {
                    switch(ch = toupper(getch())) {
                        case SPACE : return(0);
                        case RET : marknext = ' '; break;
                        case ESC : return(0);
                        default  : marknext = ch; break;
                    }
                }
            }
            if (kbhit()) {
                switch(ch = toupper(getch())) {
                    case SPACE : return(0);
                    case RET : marknext = ' '; break;
                    case ESC : return(0);
                    default  : marknext = ch; break;
                }
            }
            data.x = x; data.y = y; data.hd = hd; data.vd = vd;
            data.time= timex() - start_time;
            if (marknext) {
                data.mark = marknext;
                marknext = 0;
            }
            else data.mark = 0;
            _write(han,&data,sizeof(datatype));
            if (++total_lp > maxlp - 1)
                return(0);
            if (screen_mode() != TEXT) {
                x *= 8; y *= 14;
/*ND mod bind (&x,0,649); */
                bind(&x,0,639);
                bind(&y,0,349);
            }
            else { bind(&x,0,79);
                   bind(&y,0,24);
```

```c
                    }
            if (useboxes) {
                if (!((curbox = lookupbox(abl, x,y))) {
                    if (boxmark) {
                        s = place_lp(x,y,YELLOW);
                        delay(20);
                        remove_lp(x,y,s);
                        }
                    if (curbox != prevbox)
                        index = 0;
                    prevbox = curbox;
                    }
                else { index = 0;
                    if (noboxmark) {
                        s = place_lp(x,y,YELLOW);
                        delay(20);
                        remove_lp(x,y,s);
                        }
                    }
                }
            else { if (noboxmark) {
                    s = place_lp(x,y,YELLOW);
                    delay(20);
                    remove_lp(x,y,s);
                    }
                index = 0;
                }
            }
/*      mouse_off();*/
        *box = curbox;
        return(curbox);
    } void dispose_activeboxlist (activeboxtype *abl)
    { activeboxtype *tmpb;
        while (abl != NULL) {
            tmpb = abl->next;
            free(abl);
            abl = tmpb;
            }
    }
\032
```

1stowyd.c

```c
define CAL_COSIZE 3 unsigned gen_coeffs(Matrix *mx,Matrix *my,Matrix *ix, Matrix *iy, Matrix *dxm, Matrix *dym)

{ Matrix *cm;
      Matrix *sv;
      int success;

success = 1;
      cm = newzeromatrix(3,3);
      sv = newzeromatrix(3,1);          /* Solving for X coefficients */
      elem(cm,0,0) = numRows(dxm);
      elem(cm,0,1) = elem(cm,1,0) = sumvect(dxm,1.0);
      elem(cm,0,2) = elem(cm,2,0) = sumvect(dym,1.0);
      elem(cm,1,1) = sumvect(dxm,2.0);
      elem(cm,2,1) = elem(cm,1,2) = multvects(dxm,1.0,dym,1.0);
      elem(cm,2,2) = sumvect(dym,2.0);

elem(sv,0,0) = sumvect(ix,1.0);
      elem(sv,1,0) = multvects(dxm,1.0,ix,1.0);
      elem(sv,2,0) = multvects(dym,1.0,ix,1.0);
      if (!matrixsoln(cm,mx,sv))
          success = 0;
      freeMatrix(cm);
      freeMatrix(sv);
                                        /* Solving for Y coefficients */
      cm = newzeromatrix(3,3);
      sv = newzeromatrix(3,1);
      elem(cm,0,0) = numRows(dym);
      elem(cm,0,1) = elem(cm,1,0) = sumvect(dym,1.0);
      elem(cm,0,2) = elem(cm,2,0) = sumvect(dxm,1.0);
      elem(cm,1,1) = sumvect(dym,2.0);
      elem(cm,2,1) = elem(cm,1,2) = multvects(dym,1.0,dxm,1.0);
      elem(cm,2,2) = sumvect(dxm,2.0);

elem(sv,0,0) = sumvect(iy,1.0);
      elem(sv,1,0) = multvects(dym,1.0,iy,1.0);
      elem(sv,2,0) = multvects(dxm,1.0,iy,1.0);
      if (!matrixsoln(cm,my,sv))
          success = 0;
      freeMatrix(cm);
      freeMatrix(sv);
      return(success);
    } int calc_lp (Matrix *m, double x1, double x2)
    { return((int) elem(m,0,0) + (elem(m,1,0) * x1) + (elem(m,2,0) * x2));
    }
\032
``` matfunct.c

```c
include <stdio.h>
#include <stdlib.h>
#include <math.h>
#include "c:\cgaze\matrixde.h"

/* AUTHOR: Kevin S. Spetz (Adapted from B J Haberkorn's code)
 * DATE: 11/88
 * Routine allocates space for a matrix of size (rows, cols), and returns
 * a pointer to that matrix. The elements of the matrix can be accessed
 * through the macro elem
 */
Matrix *newMatrix(int rows, int cols)
   {  Matrix *tmp;
      double **temp;
      unsigned int i,rws,cls;

rws = (unsigned int) rows;
      cls = (unsigned int) cols;
      if ((tmp = new(Matrix)) == NULL) {
         fprintf(stderr,"Memory Allocation Error in newMatrix");
         return(NULL);
      }
      numRows(tmp) = rows;  tmp->rowdimen = rws;
      numCols(tmp) = cols;  tmp->coldimen = cls;
      temp = (double **) calloc(rws, ((unsigned int) sizeof(double *)));
      if (temp == NULL) {
         fprintf(stderr,"Memory Allocation Error in newMatrix");
         return(NULL);
      }
      for (i = 0; i < rws; i++) {
         temp[i] = (double *) calloc(cls,((unsigned int) sizeof(double)));
         if (temp[i] == NULL) {
            fprintf(stderr,"Memory Allocation Error in newMatrix");
            return(NULL);
         }
      }
      tmp->mat = temp;
      return(tmp);
   }

/* AUTHOR: Kevin S. Spetz  (adapted from B J Haberkorn's code)
 * DATE: 11/88
 * Routine to destroy, and free the memory held by a matrix created by
 * newMatrix. To use pass the pointer to the condemned matrix
 */
void freeMatrix(Matrix *m)
   {  int i;
      assert(((unsigned int) numRows(m))==m->rowdimen);
      assert(((unsigned int) numCols(m))==m->coldimen);
      for (i = 0; i < m->rowdimen; i++)
         free(m->mat[i]);
      free(m->mat);
      free(m);
   }

/* AUTHOR: Kevin S. Spetz
 * DATE 7/88
 * Routine to print out the elements of a matrix pointed to by m
 */
void printmatrix(Matrix *m)
   {  int r,c;
      printf("Matrix = \n");
      for (r = 0; r < numRows(m); r++) {
         printf("[ ");
         for (c = 0; c < numCols(m); c++)
            printf("%3.3f ",elem(m,r,c));
         printf("]\n");
      }
   }

/* AUTHOR: Kevin S. Spetz
 * DATE: 7/88
 * Routine to clear all of the elements in a matrix, m.
 */
void clearmatrix(Matrix *m)
   {  int r,c;
      for (r = 0; r < numRows(m); r++)
         for (c = 0; c < numCols(m); c++)
            elem(m,r,c) = 0.0;
   } int dupMatrix(Matrix *src, Matrix **dst)
   {
      int r,c;
      if (*dst != NULL) freeMatrix(*dst);
      if ((*dst = newMatrix(numRows(src), numCols(src))) == NULL) return(0);
      else {
         for (c = 0; c < numCols(src); c++)
            for (r = 0; r < numRows(src); r++)
               elem(*dst, r, c) = elem(src, r, c);
```

```
            return(1);
            }
      }

/* AUTHOR: Kevin S. Spetz
 * DATE: 7/88
 * Routine which calls newMatrix to create a matrix, then sets all the
 * elements to zero
 */
Matrix *newzeromatrix(int rows, int cols)
   { int r,c;
     Matrix *temp;

if ((temp = newMatrix(rows,cols)) != NULL) {
        for (c = 0; c < numCols(temp); c++)
          for (r = 0; r < numRows(temp); r++)
            elem(temp,r,c) = 0.0;
        }
     return(temp);
   }

/* AUTHOR: Kevin S. Spetz
 * DATE: 7/88
 * Routine that sums all of the points in vector m. A Vector is considered
 * to be a matrix of size (row,1), and is not a separate type from the matrix
 * type. Each element is raised to the power p before being added to the sum
 * in this way you can create sum[(elem^p)], etc
 */
double sumvect(Matrix *m,double p)
   { int index;
     double temp;
     temp = 0.0;
     for (index = 0; index < numRows(m); index ++)
        temp = temp + pow(elem(m,index,0),p);
     return(temp);
   }

/* AUTHOR: Kevin S. Spetz
 * DATE: 7/88
 * Routine that multiplies two vectors together, after raising each element
 * of the vectors to p1 and p2 respectivly. What is meant by vector is
 * described by sumvect. These routines are used for solving a linear
 * system of equations defined in matrices
 */
double multvects(Matrix *m1, double p1,Matrix *m2, double p2)
   { int index;
     double temp;
     temp = 0.0;
     for (index = 0; index < numRows(m1); index++)
        temp = temp + (pow(elem(m1,index,0),p1) * pow(elem(m2,index,0),p2));
     return(temp);
   }

/* AUTHOR: Kevin S. Spetz
 * DATE: 7/88
 * Routine that switches rows t and b in the matrix m.
 */
void switchrows(Matrix *m,int t, int b)
   { int col;
     double temp;
     if (t != b)
        for (col = 0; col < numCols(m); col++) {
           temp = elem(m,t,col);
           elem(m,t,col) = elem(m,b,col);
           elem(m,b,col) = temp;
           }
   }

/* AUTHOR: Kevin S. Spetz
 * DATE: 7/88
 * Routine to find a valid pivot row for a gaussian elimination solution
 * to a system of linear equations.
 */
unsigned findvalrow(Matrix *m, int x,Matrix *l)
   { int row;
     for (row = x; row < numRows(m); row++)
        if (elem(m,row,x) != 0.0) {
           switchrows(m,row,x);
           switchrows(l,row,x);
           return(1);
           }
     return(0);
   }

/* AUTHOR: Kevin S. Spetz
 * DATE: 7/88
 * Routine which solves a system of linear equations for a parameter vector.
 * The coefficient matrix is c, the parameter matrix (solution) and the
 * solution vector is s. [c][p] = [s].
 */
unsigned matrixsoln(Matrix *c, Matrix *p, Matrix *s)
   { int col,row,pivcol;
     double temp;
```

```
    for (pivcol = 0; pivcol < numCols(c); pivcol++)
      if (findvalrow(c,pivcol,s)) {
        for (row = pivcol; row < numRows(c); row++) { if (row == pivcol)
            elem(s,row,0) = elem(s,row,0)/elem(c,row,pivcol);
          else if (elem(c,row,pivcol))
               elem(s,row,0) = elem(s,pivcol,0) - (elem(s,row,0)/elem(c,row,pivcol));

for (col = numCols(c) - 1; col > pivcol - 1; col--)
            if (row == pivcol)
              elem(c,row,col) = elem(c,row,col)/elem(c,row,pivcol);
            else if (elem(c,row,pivcol))
                 elem(c,row,col) = elem(c,pivcol,col) - (elem(c,row,col)/elem(c,row,pivcol));
        }
      }
    for (row = numRows(p) - 1; row > -1; row--) {
      temp = 0.0;
      for (col = numCols(c) - 1; col > row - 1; col--)
        temp = temp + elem(p,col,0) * elem(c,row,col);
      if (elem(c,row,row))
        elem (p,row,0) = (elem(s,row,0) - temp)/elem(c,row,row);
      else { printf("Calibration Matrix Unsolvable...\n");
             return(0);
           }
    }
    return(1);
  }
```

\032 newfg.c

```c
include <stdio.h> define USE_BOTH_AVW 1       /* 0 will make the system use one AVW */
                             /* 1 will make the system use both AVWs */ define PI 3.141592654 include <dos.h>
include <mem.h>
#include <math.h>
#include <alloc.h>
#include "c:\cgaze\fgroutns.h"

int avw_bank = 0;

int avw(void)
  { return(avw_bank);
  } int ivw(void)
  { if (USE_BOTH_AVW)
        return(1 - avw_bank);
    else return(avw_bank);
  } void initialize(void)
  { int i;

/* Set up the input LUT's */ outportb(_FG_CONTROL_PORT + 1,0x00);
    for (i = 0; i <= 255; i++) {
        outportb(_FG_CONTROL_PORT + 2,i);
        outportb(_FG_CONTROL_PORT + 3,i);
    }
    outportb(_FG_CONTROL_PORT + 1,0x01);
    for (i = 0; i <= 255; i++) {
        outportb(_FG_CONTROL_PORT + 2,i);
        outportb(_FG_CONTROL_PORT + 3,i);
    }
    outportb(_FG_CONTROL_PORT + 1,0x02);
    for (i = 0; i <= 255; i++) {
        outportb(_FG_CONTROL_PORT + 2,i);
        outportb(_FG_CONTROL_PORT + 3,i);
    }
    outportb(_FG_CONTROL_PORT + 1,0x03);
    for (i = 0; i <= 255; i++) {
        outportb(_FG_CONTROL_PORT + 2,i);
        outportb(_FG_CONTROL_PORT + 3,i);
    }
    outportb(_FG_CONTROL_PORT + 2,0x00);
    outportb(_FG_CONTROL_PORT + 3,0x00);

/* Set offset voltage */ outportb(_FG_CONTROL_PORT + 4,0xF3);

outportb(_FG_CONTROL_PORT,0x04);

for (i = 0; i <= 100; i++)
        outportb(_FG_CONTROL_PORT + 4,0x0);
```

```c
    outportb(_FG_CONTROL_PORT,0x8);
    for (i = 0; i <= 90; i++)
       outportb(_FG_CONTROL_PORT + 4,0x0);

/* Enable the framegrabber frame memory onto the PC bus */ outportb(_FG_CONTROL_PORT,0x16);

/* Choose the system clock source to be the phase lock loop */ outportb(_FG_CONTROL_PORT + 5,0x02);
/* Set the horizontal and vertical offsets in frame memory to 0 */ outportb(_FG_CONTROL_PORT + 6,0x00);
    outportb(_FG_CONTROL_PORT + 7,0x00);

/* Enable the pixel buffer */ outportb(_FG_CONTROL_PORT + 8,0x40);

/* Do not protect any bit planes during host access or a frame */
/* memory clear operation */ outportb(_FG_CONTROL_PORT + 9,0x00);

/* Do not protect any bit planes during image acquistion */ outportb(_FG_CONTROL_PORT + 10,0x00);
continuous();
  } void continuous(void)
  { short temp;
    temp = inportb(_FG_CONTROL_PORT + 5);

outportb(_FG_CONTROL_PORT + 5,(temp | 0xC0));
  } void grabframe(void)
  { short temp;
                                            /* Turn acquisition off and
                                             * Wait until done
                                             */
    temp = inportb(_FG_CONTROL_PORT + 5);
    outportb(_FG_CONTROL_PORT + 5,(temp & 0x3F));
    while ((inportb(_FG_CONTROL_PORT + 5) & 0xC0) != 0);

/* Start a frame grab
                                             */
    temp = inportb(_FG_CONTROL_PORT + 5);
    outportb(_FG_CONTROL_PORT + 5,(temp | 0x80));
    while ((inportb(_FG_CONTROL_PORT + 5) & 0xC0) != 0);
  } void end_acquire(void)

{
  short temp;

temp = inportb(_FG_CONTROL_PORT + 5);
    outportb(_FG_CONTROL_PORT + 5,(temp & 0x3F));
} void wait_nop(void)

{
    while ((inportb(_FG_CONTROL_PORT + 5) & 0xC0) != 0);
} void find_odd(void)

{
  int odd;
  short temp;

/* wait until odd field occurs */ odd = 0;
    while(odd == 0) {
        temp = inportb(_FG_CONTROL_PORT + 5);
        if((temp & 0x04) == 0) {
              delay(2);
              temp = inportb(_FG_CONTROL_PORT + 5);
              if((temp & 0x04) == 0x04) odd = 1;

}
    }
}
```

```c
void panswitch(void)
{
    short port;
    int find_odd;

find_odd = 0;

if (USE_BOTH_AVW)
    {
        if (avw_bank == 0)
        {
            avw_bank = 1;
            port = 64;
        }
        else
        {
            avw_bank = 0;
            port = 0;
        }
    }

/* Both of the methods below work for the aquisition of frames in 33 ms. */

/* This algorithm looks for two vertical blank periods. Because */
        /* this is the case, only 16 ms may be used for the eye tracking */
        /* algorithms.                                                   */

/*      while((inportb(_FG_CONTROL_PORT + 5) & 0x10) == 0x10);
        delay(2);
        while((inportb(_FG_CONTROL_PORT + 5) & 0x10) == 0x10);
        outportb(_FG_CONTROL_PORT + 6, port);
        delay(2);
*/ delay(2); /* make sure that the previous frame's odd field is not recognized */
        while(find_odd == 0)
        {
            if((inportb(_FG_CONTROL_PORT + 5) & 0x04) == 0x04)
            {
                find_odd = 1;
            }
        } delay(2);
        while((inportb(_FG_CONTROL_PORT + 5) & 0x10) == 0x10);
        outportb(_FG_CONTROL_PORT + 6, port);
}

/***************************************************************/
/*                                                             */
/* This routine will wait for the present framgrabber operation */
/* to complete, switch the active video memory, and then grab a */
/* new frame of data. If USE_BOTH_AVW is 0, the active video    */
/* will not be switched.                                       */
/*                                                             */
/***************************************************************/ void grabnswitch(void)
{   short temp;
    int find_odd;
    short out_val;
/*    short port;*/
/*    while((inportb(_FG_CONTROL_PORT + 5) & 0x04) != 0x04); */ find_odd = 0;

while(find_odd == 0) { temp = inportb(_FG_CONTROL_PORT + 5);

if((temp & 0x04) == 0) { delay(2);
            temp = inportb(_FG_CONTROL_PORT + 5);
            if((temp & 0x04) == 0x04) find_odd = 1;
        }
    } out_val = temp | 0x080;     /* set acqmd1 bit to a 1 */
    out_val = out_val & 0x0BF;  /* set acqmd0 bit to a 0 */ outportb(_FG_CONTROL_PORT + 5,out_val);

if (USE_BOTH_AVW) {
        if (avw_bank == 0) {
            avw_bank = 1;
/*          port = 64;*/
        }
        else { avw_bank = 0;
/*             port = 0;*/
        }
    }

/*  temp = inportb(_FG_CONTROL_PORT + 5); */
```

```c
/* start a grab operation */

/*    outportb(_FG_CONTROL_PORT + 5,(temp | 0x80));   */
    } int fgstatus(void)
    { return((int) (inportb(_FG_CONTROL_PORT + 5) & 0x10));
    } void timevblank(void)
    {
      while((inport(_FG_CONTROL_PORT + 5) & 0x10) != 0);
    } void switch_avw(void)
    { if (USE_BOTH_AVW) {
         if (avw_bank == 0) {
            avw_bank = 1;
            outportb(_FG_CONTROL_PORT + 6, 64);
            outportb(_FG_CONTROL_PORT + 7, 0);
            }
         else { avw_bank = 0;
                outportb(_FG_CONTROL_PORT + 6, 00);
                outportb(_FG_CONTROL_PORT + 7, 00);
                }
         }
      else { outportb(_FG_CONTROL_PORT + 6, 0x00);
             outportb(_FG_CONTROL_PORT + 7, 0x00);
             }
    } void set_avw(int avw)
    { if (avw == 1) {
         if (avw_bank == 0) {
            avw_bank = 1;
            outportb(_FG_CONTROL_PORT + 6, 64);
            outportb(_FG_CONTROL_PORT + 7, 0);
            }
         else { avw_bank = 0;
                outportb(_FG_CONTROL_PORT + 6, 00);
                outportb(_FG_CONTROL_PORT + 7, 00);
                }
         }
      else { outportb(_FG_CONTROL_PORT + 6, 0x00);
             outportb(_FG_CONTROL_PORT + 7, 0x00);
             }
    } unsigned char inpic (unsigned x,unsigned y,int w)
    { if ((x > 512) || (y > 480))
         return(0);
      outportb(_FG_CONTROL_PORT,0x16 + (((y/128) + w * 4) * 32));
      return peekb(_FG_IMAGE_BASE,y * 512 + x);
    } void outpic (int x,int y, unsigned char v,int w)
    { outportb(_FG_CONTROL_PORT,0x16 + (((y/128) + w * 4) * 32));
      pokeb(_FG_IMAGE_BASE,y * 512 + x,v);
    } void getrowivw(unsigned row, unsigned start, size_t count, unsigned char *buf)
    { outportb(_FG_CONTROL_PORT,0x16 + (((row/128) + ivw() * 4) * 32));
      movedata(_FG_IMAGE_BASE,row * 512 + start,_DS,(unsigned) buf,count);
    } void putrowivw(unsigned row, unsigned start, size_t count, unsigned char *buf)
    { outportb(_FG_CONTROL_PORT,0x16 + (((row/128) + ivw() * 4) * 32));
      movedata(_DS,(unsigned) buf,_FG_IMAGE_BASE,row * 512 + start,count);
    } void getrowavw(unsigned row, unsigned start, size_t count, unsigned char *buf)
    { outportb(_FG_CONTROL_PORT,0x16 + (((row/128) + avw() * 4) * 32));
      movedata(_FG_IMAGE_BASE,row * 512 + start,_DS,(unsigned) buf,count);
    } void putrowavw(unsigned row, unsigned start, size_t count, unsigned char *buf)
    { outportb(_FG_CONTROL_PORT,0x16 + (((row/128) + avw() * 4) * 32));
      movedata(_DS,(unsigned) buf,_FG_IMAGE_BASE,row * 512 + start,count);
    } void makehistogram(histarray h,int x_inc, int y_inc)
    { int x,y;
      unsigned char *buf;
      buf = (unsigned char *) malloc(512 * sizeof(unsigned char));
      for (x = 0; x < 256; x++)
         h[x] = 0;
      for (y = 0;y < 480; y += y_inc) {
         outportb(_FG_CONTROL_PORT,0x16 + ((y / 128) + avw() * 4) * 32);
         movedata(_FG_IMAGE_BASE,y * 512,_DS,(unsigned) buf,512);
         for (x = 0; x < 512; x += x_inc)
            h[(int) *(buf+ x)]++;
         }
      free(buf);
```

```c
}
void initialize_again()
{
    int find_odd=0;
    short temp;

initialize();
    while(find_odd == 0)   /* wait until odd field occurs */
    {
      temp = inportb(_FG_CONTROL_PORT + 5);
      if((temp & 0x04) == 0)
        {
                delay(2);
          temp = inportb(_FG_CONTROL_PORT + 5);
                if((temp & 0x04) == 0x04) find_odd = 1;
        }
      } continuous();          /* perform a grab */

} void newgrabnswitch()
{
  delay(1);
  panswitch();
}\032
``` fastfind.c

```c
/****************************************************************/
/* This file contains the routines that will identify the center of the*/
/* pupil and the glint by THRESHHOLDING. The threshhold for the glint */
/* is established by computing a histogram over the entire image and  */
/* selecting the highest values. The threshhold for the pupil is      */
/* established by first locating the glint, and then computing the    */
/* histogram over a 150x150 box centered at the glint. The histogram  */
/* should then appear as two peaks and a valley, with the valley      */
/* representing the threshhold value.                                 */
/*                                                                    */
/* Authors: David Handelsman and Kevin Spetz                          */
/* Date   : 8/22/89                                                   */
/****************************************************************/ define PI 3.141592653
define FINDRES 20              /* Resolution used to scan image for pupil */
#define MINCORDLEN 26           /* Minimum eye width */
#define MINGLINTSIZE 1          /* Minimum glint size */
#define ALLOWEDFAILURES 20      /* # of failures before recalibrating */
#define MINGLINTSIZE 1          /* Minimum glint size */
#define NUMMISS 2               /* Allowed # of skipped pixels in chord */
#define x_image_start 10        /* smallest usable x frame coord */
#define x_image_stop 470        /* largest usable x frame coord */
#define y_image_start 24        /* smallest usable y frame coord */
define y_image_stop 470        /* largest usable y frame coord */ include <mem.h>
include <stdio.h>
#include <ctype.h>
#include <conio.h>
#include <fcntl.h>
#include <string.h>
#include <io.h>
#include <stat.h>
#include <dos.h>
#include <math.h>
#include <alloc.h>
#include "c:\cgaze\fgroutns.h"

/* GLOBAL STATIC VARIABLES */
typedef struct {
    double x;
    double y;
} xycoords;

float p_x;                      /* pupil center x     */
float p_y;                      /* pupil center y     */
float q_x;                      /* glint center x     */
float q_y;                      /* glint center y     */
int   q_thresh;                 /* glint edge threshhold */
int   p_thresh=255;             /* pupil threshhold   */
int   vpupildiam;               /* vertical pupil diameter */
int   hpupildiam;               /* horizontal pupil diameter */
int   previous_eye=0;           /* 1=pervious info available */
unsigned char frame_buffer[512]; /* row of frame buffer */

/*******************************
global debugging variables start
*******************************/
int no_glint_global;
int no_pupil_global;
```

```c
int global_failed;
int global_found;
int no_glint_local;
int no_pupil_local;
int local_failed;
int local_found;
int no_start;
int bad_aspect;
/*********************************
global debugging variables end
*********************************/

/* Routine returns ratio of two numbers passed in parameters.  0 - 1 */
double aspect(int x, int y)
{
 if (x > y)
    return((double) y/x);
 else return((double) x/y);
}

/*
 * Sets a threshold for glint detection.
 * Returns success or failure.
 */
unsigned setthresholds(void)
{
  int gp;
  histarray localh;

makehistogram(localh,2,2);
  gp = 0;
  g_thresh = 256;
  while ((gp+=localh[--g_thresh]) < 5);
  g_thresh--;

if (g_thresh >100) return(1);
  else return(0);
}

/* Following four routines: Look in a given direction until NUMMISS points
 * in a row are below the threshold t.  Used by to find the edges
 * the pupil.
 */
int lookbackx (int x, int y,int t)
{
  int misses;

for (misses = 0; misses < NUMMISS;misses++)
    while(inpic(--x,y,ivw()) > t)
       misses = 0;
  return(x + NUMMISS);
} int lookforwx (int x, int y,int t)
{
  int misses;

for (misses = 0; misses < NUMMISS;misses++)
    while(inpic(++x,y,ivw()) > t)
       misses = 0;
  return(x - NUMMISS);
} int lookbacky (int x, int y,int t)
{
  int misses;

for (misses = 0; misses < NUMMISS;misses++)
    while(inpic(x,--y,ivw()) > t)
       misses = 0;
  return(y + NUMMISS);
} int lookforwy (int x, int y,int t)
{
  int misses;

for (misses = 0; misses < NUMMISS;misses++)
    while(inpic(x,++y,ivw()) > t)
       misses = 0;
  return(y - NUMMISS);
}

/*
 * Determines the location of the new bright spot (glint) by searching a
 * limited area around the old glint.
 * Returns success or failure.
 */
int local_quick_find_glint (int old_x, int old_y, int *x, int *y)
{
  int i;
  int j;
  int temp;
  int counter;
```

```
   int direction=2;
   int width=125;

counter=0;
  j=old_y;
  while (counter < 30)
     {
     getrowivw(j,old_x-60,width,frame_buffer);
     for (i=(0);i<(120);i++)
        {
        temp=*(frame_buffer+i);
        if ( temp>g_thresh)
           {
           *x=i+old_x-60;
           *y=j;
           return(1);
           }
        } counter+=1;
     j+=counter*direction;
     direction=direction*(-1);
     }
  return(0);
}

/*
 * Uses previous information to find the glint quickly. Searches out
 * from the previous glint to find the new glint.
 * Returns success or failure.
 */
unsigned localfindglint(void)
{
  int tx;
  int ty;
  int x;
  int y;
  int v_chordend;
  int v_chordbeg;

x = (int)g_x;
  y = (int)g_y;

if (!local_quick_find_glint( (int)g_x,(int)g_y,&x,&y))
     {
     return(0);
     } tx = (lookforwx(x,y,g_thresh) + lookbackx(x,y,g_thresh)) / 2.0;
  v_chordbeg = lookbacky(tx,y,g_thresh);
  v_chordend = lookforwy(tx,y,g_thresh);
  ty = g_y = (v_chordend + v_chordbeg) / 2.0;
  if ( abs(v_chordend - v_chordbeg) > MINGLINTSIZE)
     {
     g_x = (lookforwx(tx,ty,g_thresh) + lookbackx(tx,ty,g_thresh)) / 2.0;
     return(1);
     }
  else
     {
     return(0);
     }
}

/* Global routine to find the glint.
 * Returns success or failure.
 */
unsigned globalfindglint(void)
{
  int tx;
  int ty;
  int x;
  int i;
  int y;
  int v_chordend;
  int v_chordbeg;

x = x_image_start;    /* initial x position */
  y = y_image_start;    /* initial y position */
  while (y< y_image_stop)
     {                                    /* Finding Glint */
     getrowivw(y,x_image_start,x_image_stop-x_image_start-2,frame_buffer);
     x=x_image_start;
     while (x < x_image_stop)
        {
        i=x-x_image_start;
        if ( *(frame_buffer+i) > g_thresh)
           {
           tx = (lookforwx(x,y,g_thresh) + lookbackx(x,y,g_thresh)) / 2.0;
           v_chordbeg = lookbacky(tx,y,g_thresh);
           v_chordend = lookforwy(tx,y,g_thresh);
           ty = g_y = (v_chordend + v_chordbeg) / 2.0;
           if (abs(v_chordend - v_chordbeg) > MINGLINTSIZE)
              {
              g_x=(lookforwx(tx,ty,g_thresh)+lookbackx(tx,ty,g_thresh))/2.0;
              return(1);
```

```
            }
         x+=3;
         }
      y+=2;
      }
   return(0);
}

/*******************************************************/
         /*********   GLINT SEARCH ROUTINES END   ***********/
         /*******************************************************/
/*
 * Identifies the pupil threshhold by first computing a local histogram
 * centered around the glint, and then identifying the valley between two
 * peaks as the pupil threshhold. Returns success or failure.
 */
int get_pupil_thresh(void)
{
 int i;
 int j;
 int hist[256];
 int h[256];
 int min=256;
 int max=0;
 int temp;
 int status;
 int x;
 int y;

x=(int)g_x;
 y=(int)g_y;
 memset(hist,0,512);

for (j=y-50;j<=y+50;j+=4)              /* make histogram */
    {
    getrowivw(j,x-50,110,frame_buffer);
    for (i=0;i<=100;i+=4)
        {
        if ( ((j>=(y-10)) && (j<=(y+10))) && ((i<=(60)) && (i>=(40))) )
            {
            /* skip over glint */
            }
        else
            {
            temp=*(frame_buffer+i);
            hist[temp]++;
            if (temp <min) min=temp;
            if (temp >max) max=temp;
            }
        }
    } for (i=min;i<=max;i++)                 /* median filter */
    {
    h[i]=(hist[i-1]+hist[i]+hist[i+1])/3;
    } status=0;                              /* identify threshhold */
 for (i=max;i>min;i--)
    {
    switch (status) {
       case 0:if (h[i]>h[i-1])          /* look for peak */
              {
              status=1;
              }
              break;
       case 1:if (h[i]<h[i-1])          /* look for valley */
              {
              p_thresh=i;
              status=2;
              }
              break;
       case 2:if (h[i]>h[i-1])          /* look for peak */
              {
              return(1);
              }
              break;
       }
    }
 return(0);
}

/*
 * Search the area near the glint for three consecutive pixels that are
 * above the pupil threshhold. These three pixels are used as an arbitrary
 * starting point INSIDE the pupil. Returns success or failure.
 */
int find_pupil_start(int *xstart, int *ystart)
{
   int i;
   int j;
   int done=0;
   int width;
   int x;
   int y;
   int offset;
```

```
x=(int)g_x;
y=(int)g_y;

width=101;
offset=width/2;
j=y+10;
if (j>y_image_stop) j=y_image_stop-5;

while ( (j>(y-offset)) && (!done) )
   {
   getrowivw(j,x-offset,width,frame_buffer);
   i=1;
   done=0;
   while ( (i<(100)) && (!done) )
      {
      if ( (i>(offset-10)) && (i<(offset+10)) && (j>(y-7)) && (j<(y+7)) )
         {
         /* skip over glint */
         }
      else
         {
         if ( (*(frame_buffer+i-1)>p_thresh) && (*(frame_buffer+i)>p_thresh)
             && (*(frame_buffer+i+1)>p_thresh) )
            {
            *xstart=i+x-offset;
            *ystart=j;
            return(1);
            }
         }
      i++;
      }
   j-=2;
   }
return(0);
}

/*
* Identifies the center of the pupil when no previous information is
* available.  This routine calls the pupil-threshholding routine.  Returns
* success or failure.
*/
unsigned global_pupil_search(void)
{ int tx;
int ty;
int x;
int y;
int v_chordend;
int v_chordbeg;
int h_chordbeg;
int h_chordend;
int xstart;
int ystart;

if (!get_pupil_thresh())
   {
   return(0);
   } if (!find_pupil_start(&xstart,&ystart))
   {
   return(0);
   } x = xstart;
y = ystart;

while (1)
   {
   if (inpic(x,y,ivw()) > p_thresh)
      {
      tx = (lookforwx(x,y,p_thresh) + lookbackx(x,y,p_thresh)) / 2.0;
      v_chordbeg = lookbacky(tx,y,p_thresh);
      v_chordend = lookforwy(tx,y,p_thresh);
      ty = p_y = (v_chordend + v_chordbeg) / 2.0;
      if (((vpupildiam - (v_chordend - v_chordbeg))) > MINCORDLEN)
         {
         h_chordbeg = lookbackx(tx - 20,ty,p_thresh);
         h_chordend = lookforwx(tx + 20,ty,p_thresh);
         hpupildiam = h_chordend - h_chordbeg;

p_x=(h_chordbeg+h_chordend)/2;
         if (aspect(hpupildiam,vpupildiam) < 0.75)
            {
            return(0);
            }
         return(1);
         }
      else
         {
         /* No action, try another point */
         }
      }
   if ((x+=FINDRES) > x_image_stop)          /* jump to a new pixel */
      {
```

```
         x = xstart;
         if ((y-=FINDRES) < (g_y-100))
             {
             return(0);
             }
         }
     }
}

/*
 * Identifies the center of the pupil if the threshhold is known.
 * Returns success or failure.
 */
unsigned local_pupil_search(void)
{
  int ty;
  int x;
  int y;
  int h_chordend;
  int h_chordbeg;
  int v_chordend;
  int v_chordbeg;
  int xstart;
  int ystart;
  int temp_x;

if (!find_pupil_start(&xstart,&ystart))
     {
     no_start++;
     return(0);
     } x = xstart;
  y = ystart;

v_chordbeg = lookbacky(x,y - 10,p_thresh);
  v_chordend = lookforwy(x,y + 10,p_thresh);
  ty = p_y = (v_chordend + v_chordbeg) / 2.0;

h_chordbeg = lookbackx(x - 10,ty,p_thresh);
  h_chordend = lookforwx(x + 10,ty,p_thresh);
  hpupildiam = h_chordend - h_chordbeg;
  p_x=temp_x=(h_chordbeg+h_chordend)/2;
  v_chordbeg = lookbacky(temp_x,ty - 10,p_thresh);
  v_chordend = lookforwy(temp_x,ty + 10,p_thresh);
  ty = p_y = (v_chordend + v_chordbeg) / 2.0;
  vpupildiam=v_chordend-v_chordbeg;
  if (aspect(hpupildiam,vpupildiam) < 0.75)
     {
     bad_aspect++;
     return(0);
     }
  return(1);
}

/********************************************************/
          /***** GLOBAL AND LOCAL SEARCH CONTROLLING ROUTINES *****/
          /********************************************************/
/*
 * Identifies the glint and pupil centers from within the entire image.
 * Returns success or failure.
 */
int globalsearch(xycoords *p, xycoords *g, int *hdiameter, int *vdiameter)
{
    static int glint_misses;

if (!globalfindglint())
        {
        no_glint_global++;
        global_failed++;
        glint_misses++;
        if (glint_misses>10)
           {
           glint_misses=0;
           }
        return(0);
        }
outpic ( (int)g_x,(int)g_y,(unsigned char)0,ivw());

if (global_pupil_search())
   {
   global_found++;
   p->x=p_x;
   p->y=p_y;
   g->x=g_x;
   g->y=g_y;
   *hdiameter=hpupildiam;
   *vdiameter=vpupildiam;
   outpic( (int)p_x,(int)p_y,(unsigned char)200,ivw());
   return(1);
   }
else
   {
   global_failed++;
   no_pupil_global++;
```

```
      return(0);
      }
}

/*
 * Identifies the glint and pupil centers from within a portion of the
 * image, as determined by the previous glint and pupil centers.
 * Returns success or failure.
 */
int localsearch (xycoords *p, xycoords *g, int *hdiameter, int *vdiameter)
{ if (!localfindglint())
      {
      local_failed++;
      no_glint_local++;
      return(0);
      }
   outpic ( (int)g_x,(int)g_y,(unsigned char)0,ivw());

if (!(local_pupil_search()))
      {
      local_failed++;
      no_pupil_local++;
      return(0);
      }
   else
      {
      local_found++;
      p->x=p_x;
      p->y=p_y;
      g->x=g_x;
      g->y=g_y;
      *hdiameter=hpupildiam;
      *vdiameter=vpupildiam;
      outpic ( (int)p_x,(int)p_y,(unsigned char)200,ivw());
      return(1);
      }
} unsigned get_deltas(double *dx, double *dy,int *hpupdia, int *vpupdia, double numr)
{
  int count;
  int i;
  int noeye =0;
  int done  =0;
  int found =0;
  int thpd  =0;
  int tvpd  =0;
  int hpd   =0;
  int vpd   =0;
  double tx =0;
  double ty =0;
  xycoords pupil;
  xycoords glint;

for (count = 0; count < numr;count++)       /* get numr lookpoints */
     {
     found=0;
     if (!previous_eye)      /* NO PREVIOUS INFORMATION */
        {
        newgrabnswitch();
/*continuous();*/
        if (globalsearch(&pupil,&glint,&thpd, &tvpd))
           {
           previous_eye=1;
           found=1;
           }
        }
     else                    /* PREVIOUS INFORMATION */
        {                    /* TRY 5 local searches */
        i=0;
        done=0;
        while ( (i<5) && (!done) )
           {
           newgrabnswitch();
/*continuous();*/
           if (localsearch(&pupil,&glint,&thpd, &tvpd))
              {
              done=1;
              found=1;
              previous_eye=1;
              }
           else
              {
              i++;
              }
           }
        }                    /* search completed - success or failure */ if (!found)      /* failure */
        {
        previous_eye=0;
        noeye++;
```

```
            count--;
            if (count <0) count=0;
            if (noeye > ALLOWEDFAILURES)
                {
                    return(0);
                }
            }
        else                    /* success */
            {
            tx += glint.x - pupil.x;
            ty += glint.y - pupil.y;
/*ND    modhpd += hpd+thpd;
        vpd += vpd+tvpd;
*/      hpd = hpd+thpd;
        vpd = vpd+tvpd;
            }
        }

*dx = tx/numr;            /* average raw lookpoint information */
  *dy = ty/numr;
  *hpupdia = hpd/(int)numr;
  *vpupdia = vpd/(int)numr;
  if ((abs(*dx) > 75.0) || (abs(*dy) > 75.0))
     {
     previous_eye=0;
     return(0);
     }
  return(1);
} void print_stats ()
{
 printf ("\nDebugging information\n");
 printf ("Global glint failed   : %4d\n",no_glint_global);
 printf ("Global pupil failed   : %4d\n",no_pupil_global);
 printf ("Global failed         : %4d\n",global_failed);
 printf ("Global found          : %4d\n",global_found);
 printf ("\n");
 printf ("Local glint failed    : %4d\n",no_glint_local);
 printf ("Local pupil failed    : %4d\n",no_pupil_local);
 printf ("Local failed          : %4d\n",local_failed);
 printf ("Local found           : %4d\n",local_found);
 printf ("\n");
 printf ("Bad aspect            : %4d\n",bad_aspect);
 printf ("No start              : %4d\n",no_start);
 getch();
}
\032

/***************************************************************
 * Module GAZE.C                           Last Revision 1-18-89
 * Author Kevin Spetz
 *
 * Coming Soon: Edge Detection by Dave Handelsman
 *
 *    These routines are responsible for generating and returning a
 * lookpoint to the calling program. To use: include the file gaze.h
 * and link this file with the program of interest
 *
 * Interface:
 *          void initgaze(xr,yr,numave,numcal);
 *              xr : Defines X resolution for returned lookpoints
 *              yr : Defines Y resolution for returned lookpoints
 *              numave : Number of lookpoints kept in the running filter
 *              numcal : Number of calibration points used
 *
 *          unsigned getgazeposition(int *x, int *y, int *pupdia);
 *              *x : Returns X lookpoint
 *              *y : Returns Y lookpoint
 *              *pupdia : Returns pupil diameter
 *              Returns : 1 - Success or 0 - failure
 ***************************************************************/ define _FG_IMAGE_BASE 0xD000       /* Base address of Frame Grabber */
define _FG_CONTROL_PORT 0x0300     /* Control Port for framegrabber */
#define PI 3.141592653
#define WINDOW 10                   /* Window used in setting thresholds */
#define FINDRES 40                  /* Resolution used to scan image for pupil */
#define MINCORDLEN 26               /* Minimum eye width */
#define MINGLINTSIZE 1              /* Minimum glint size */
#define HWSZ 45                     /* Half of the horizontal window size placed around pupil */
#define VWSZ 85                     /* Half of the vertical window placed around pupil */
#define NUMMISS 2                   /* Allowed # of skipped pixels in eye cord */
#define ALLOWEDFAILURES 20          /* # of failures before recalibrating */
#define NOPUPIL 0                   /* Error codes */
#define NOGLINT 1
#define SMALLPUPIL 2
#define SMALLGLINT 3
#define LARGEDXDY 4
#define BADPUPIL 5
#define TOOMANYFAILS 6
#define BADCAL 7
#define NUMERRMSGS 8                /* Current number of tracked errors */
#define DEFAULT_TEXT_COLOR CYAN
```

```c
#include <dos.h>
#include <stdio.h>
#include <stdlib.h>
#include <conio.h>
#include <graphics.h>
#include <math.h>
#include <ctype.h>
#include "c:\cgaze\matrixde.h"
#include "c:\cgaze\fgroutns.h"
#include "c:\cgaze\gaze.h"
#include "c:\cgaze\findeye.h"
#include "c:\ericalib\tools.h"
#include "c:\ericalib\grtools.h"

#include "c:\cgaze\lstowyd.c"          /* Include file with desired calibration */
                                       /* curve fit */

/**********************************************************************
 * Local Static Variables
 **********************************************************************/
                          /* Coefficient Matrices and running filter */
static Matrix *cal_coeffsx = NULL, *cal_coeffsy = NULL;
static Matrix *oldcalcoeffsx = NULL, *oldcalcoeffsy = NULL;
static filtertype *filter_pos = NULL;

/* General Gaze routine running Variables */
static xycoords pupil, glint;
unsigned do_recalibrate;
static int x_res, y_res, num_cal_points;
static double x_scale_fact, y_scale_fact;
static int iconcolor, iconsize;

static struct palettetype regpalette, curpalette;
static showcalpoints = 1;    /* When true routines will display calibration */
                             /* information, pause, then continue */ static int calmaxx, calmaxy; /* Max X and Y coordinates when calibration */
                             /* was performed */

/**********************************************************************
 * Global Declarations
 **********************************************************************/
                          /* Currently must be set externally */
extern int GraphDriver, GraphMode;

/* Variables for Error Tracking */
unsigned eye_errarray[10];
char *eye_errmsgs[] = {
  "No Pupil Found", "No Glint Found", "Pupil Too Small", "Glint Too Small",
  "dx or dy Too Large", "Pupil Not Round Enough", "Too Many Failures",
  "Bad Calibration"
  };

FILE *output_file;

/**********************************************************************/ static void init_graph_needs (Matrix *ix, Matrix *iy)
  { int count;
    calmaxx = getmaxx();
    calmaxy = getmaxy();
    x_scale_fact = (double)x_res / calmaxx;
    y_scale_fact = (double)y_res / calmaxy;
    switch(num_cal_points) {
      case 2 : elem(ix,0,0) = 0.8 * calmaxx;   elem(iy,0,0) = 0.2 * calmaxy;
               elem(ix,1,0) = 0.2 * calmaxx;   elem(iy,1,0) = 0.8 * calmaxy;
               break;
      case 4 : elem(ix,0,0) = 0.2 * calmaxx;   elem(iy,0,0) = 0.2 * calmaxy;
               elem(ix,1,0) = 0.8 * calmaxx;   elem(iy,1,0) = 0.2 * calmaxy;
               elem(ix,2,0) = 0.2 * calmaxx;   elem(iy,2,0) = 0.8 * calmaxy;
               elem(ix,3,0) = 0.8 * calmaxx;   elem(iy,3,0) = 0.8 * calmaxy;
               break;
      case 5 : elem(ix,0,0) = 0.1 * calmaxx;   elem(iy,0,0) = 0.1 * calmaxy;
               elem(ix,1,0) = 0.9 * calmaxx;   elem(iy,1,0) = 0.1 * calmaxy;
               elem(ix,2,0) = 0.5 * calmaxx;   elem(iy,2,0) = 0.5 * calmaxy;
               elem(ix,3,0) = 0.1 * calmaxx;   elem(iy,3,0) = 0.9 * calmaxy;
               elem(ix,4,0) = 0.9 * calmaxx;   elem(iy,4,0) = 0.9 * calmaxy;
               break;
      case 8 : elem(ix,0,0) = 0.1 * calmaxx;   elem(iy,0,0) = 0.1 * calmaxy;
               elem(ix,1,0) = 0.9 * calmaxx;   elem(iy,1,0) = 0.1 * calmaxy;
               elem(ix,2,0) = 0.5 * calmaxx;   elem(iy,2,0) = 0.3 * calmaxy;
               elem(ix,3,0) = 0.3 * calmaxx;   elem(iy,3,0) = 0.5 * calmaxy;
               elem(ix,4,0) = 0.7 * calmaxx;   elem(iy,4,0) = 0.5 * calmaxy;
               elem(ix,5,0) = 0.5 * calmaxx;   elem(iy,5,0) = 0.7 * calmaxy;
               elem(ix,6,0) = 0.1 * calmaxx;   elem(iy,6,0) = 0.9 * calmaxy;
               elem(ix,7,0) = 0.9 * calmaxx;   elem(iy,7,0) = 0.9 * calmaxy;
               break;
      default : fprintf(stderr,"Incorrect number of calibration points\n");
                fprintf(stderr,"Specified (%d) : Possible(2,4,5,8)\n",num_cal_points);
                exit(0);
                break;
      }
    if (GraphDriver == EGA) {
```

```
        iconsize = 36;
        iconcolor = CYAN;
        }
    else { iconsize = 18;
           iconcolor = 1;
         }
    for (count = 0; count < 16; count++)      /* Save the Config for a Regular Palette */
        regpalette.colors[count] = count;
    regpalette.size = 16;
    }

/* AUTHOR: Kevin S. Spetz
 * DATE: 11/15/88
 * Routine generates a circular linked list with # of nodes numnodes and
 * returns a pointer into that circle.  Will provide for real-time averaging
 * of the generated lookpoints, and will help eliminate time-delays
 */
static filtertype *init_filter(int numnodes)
    { int count;
      filtertype near *firstnode, near *currentnode, near *tempnode;
      if ((currentnode = (filtertype near *) malloc(sizeof(filtertype))) == NULL) {
          return(NULL);
          }
      firstnode = currentnode;
      firstnode->xlp = 0.0;
      firstnode->ylp = 0.0;
      firstnode->next = NULL;
      if (numnodes > 1) {
          for (count = 0; count < numnodes - 1; count++) {
              tempnode = currentnode;
              if ((currentnode = (filtertype near *) malloc(sizeof(filtertype))) == NULL) {
                  return(NULL);
                  }
              tempnode->next = currentnode;
              currentnode->xlp = 0.0;
              currentnode->ylp = 0.0;
              currentnode->next = NULL;
              }
          }
      currentnode->next = firstnode;
      return(firstnode);
      }

/* AUTHOR: Kevin S. Spetz
 * DATE: 11/15/88
 * Destroys the running filter created by init_filter
 */
static filtertype *kill_filter(filtertype *knode)
    { filtertype *nextnode;
      filtertype *start;
      filtertype *temp;
      int c = 0;

start = temp = knode;
      c++;
      nextnode = start->next;
      free(temp);
      while (nextnode != start) {          /* Work through the loop  */
          c++;
          temp = nextnode;
          nextnode = nextnode->next;       /* Go to next node        */
          free(temp);
          }
      return(NULL);
      }

/* AUTHOR: Kevin S. Spetz
 * DATE: 11/15/88
 * Increments the filter_pos and sets x and y with the filtered values.
 */
static filtertype *lp_filter(filtertype *cnode, double *x, double *y)
    { filtertype *nextnode;                /* Pointer marking pos in circle  */
      filtertype *start;                   /* Pointer marking Start in Circle */
      double tx = 0.0, ty = 0.0;
      int c = 0;

start = cnode;                       /* Set Start to passed pointer pos */
      tx+= start->xlp;
      ty+= start->ylp;
      c++;
      nextnode = start->next;
      while (nextnode != start) {          /* Work through the loop  */
          tx += nextnode->xlp;
          ty += nextnode->ylp;
          c++;
          nextnode = nextnode->next;       /* Go to next node        */
          }
      nextnode = nextnode->next;
      nextnode->xlp = *x;
      nextnode->ylp = *y;
      *x = tx/c;
      *y = ty/c;
      return(nextnode);                    /* Return the new pointer pos */
      }

/* AUTHOR: Kevin S. Spetz
```

```
* DATE: 7/88
* Routine to place and icon centered around the point (x,y)
*/
static void place_icon(int x, int y)
   {  setcolor(iconcolor);
      circle(x,y,iconsize/2);
      circle(x,y,iconsize/4);
      putpixel(x,y,iconcolor);
      delay(1500);
   }

/* AUTHOR: Kevin S. Spetz
 * DATE: 7/88
 * An anti-place_icon routine
 */
static void remove_icon(int x, int y)
   {  setcolor(0);
      circle(x,y,iconsize/2);
      circle(x,y,iconsize/4);
      putpixel(x,y,0);
   }

/* AUTHOR: Kevin S. Spetz
 * DATE: 7/88
 * The following routines manage and display the errors encountered by the
 * gaze routines.  Problems are shown on the calibration screen
 */
void clearerrs(void)
   {  int index;
      for (index = 0; index < NUMERRMSGS; index++)
         eye_errarray[index] = 0;
   }

/* AUTHOR: Kevin S. Spetz
 * DATE: 7/88
 */
static void showerrs(void)
   {  int index,xloc,yloc;
      gotoxy(12,23 - NUMERRMSGS);
      textcolor(CYAN);
      cprintf("Last Error Msgs : ");
      xloc = wherex();
      yloc = 0;
      textcolor(RED);
      for (index = 0; index < NUMERRMSGS; index++) {
         gotoxy(xloc,23 - NUMERRMSGS + yloc);
         if (eye_errarray[index]) {
            gotoxy(xloc,23 - NUMERRMSGS + yloc++);
            cprintf("%s (%d)",eye_errmsgs[index],eye_errarray[index]);
         }
      }
   }

/* AUTHOR: Kevin S. Spetz
 * DATE: 7/88
 */
static void show_cal_msg(void)
   {  gotoxy(5,12);
      textcolor(LIGHTCYAN);
      cprintf("Performing Calibration --");
      gotoxy(17,13);
      textcolor(CYAN);
      cprintf("Stare at each icon as it appears on the screen");
      showerrs();
      delay(2500);
      clearerrs();
   }

/* AUTHOR: Kevin S. Spetz
 * DATE: 7/88
 */
static void show_ega_cal_msg(void)
   {  int index,yloc;
      changetextstyle(SANS_SERIF_FONT,HORIZ_DIR,3);
      settextjustify(LEFT_TEXT,CENTER_TEXT);
      setcolor(LIGHTCYAN);
      outtextxy(getmaxx()/10,getmaxy() * 0.4,"Performing Calibration --");
      changetextstyle(SMALL_FONT,HORIZ_DIR,5);
      setcolor(CYAN);
      outtextxy(getmaxx()/5,getmaxy() * 0.5,
               "Stare at each icon as it appears on the screen");
      outtextxy(getmaxx()/5,getmaxy() - (textheight("X") * NUMERRMSGS),
               "Last Error Msgs : ");
      setcolor(RED);
      yloc = 0;
      for (index = 0; index < NUMERRMSGS; index++) {
         if (eye_errarray[index])
            outtextxy(getmaxx()/2,(getmaxy() - (textheight("X") * (NUMERRMSGS - yloc++))),
                     eye_errmsgs[index]);
      }
      delay(2500);
   }
```

```c
/* AUTHOR: Kevin S. Spetz
 * DATE: 10/88
 * Routine tests the current calibration and returns success if the calibration
 * is good, failure if the current calibration is not close enough
 */
static unsigned goodcal(Matrix *mx, Matrix *my, Matrix *ix, Matrix *iy, Matrix *dx, Matrix *dy)
{   int index,ipx,ipy,cpx,cpy;
    int good = 1;
    for (index = 0; index < num_cal_points; index++) {

/* ip? = icon position, cp? = calculated point */
        ipx = (int) elem(ix,index,0);
        cpx = (int) calc_lp(mx,elem(dx,index,0),elem(dy,index,0));
        if (abs(ipx - cpx) > 40) {
            eye_errarray[BADCAL]++;
            good = 0;
        } ipy = (int) elem(iy,index,0);
        cpy = (int) calc_lp(my,elem(dy,index,0),elem(dx,index,0));
        if (abs(ipy - cpy) > 40)) {
            eye_errarray[BADCAL]++;
            good = 0;
        } if (showcalpoints) {
            setcolor(iconcolor);
            circle(ipx,ipy,iconsize/2);
            circle(ipx,ipy,iconsize/4);
            putpixel(ipx,ipy,iconcolor);
            setcolor(RED);
            rectangle(cpx - 2, cpy - 2, cpx + 2, cpy + 2);
        }

}
    if (showcalpoints)
        delay(3000);
    cleardevice();
    return(good);
}

/* AUTHOR: Kevin S. Spetz
 * DATE: 7/88
 * Routine performs a calibration and tests it for validity. Managed by
 * calibrate.
 */
static unsigned cal(Matrix *mx, Matrix *my)
{  int index,thpd,tvpd;
   Matrix *iconx, *icony, *dxm, *dym;
   double dx,dy;
   static int program_start=1;

if (program_start)
       {
/*       initialize_again();*/
       program_start=0;
       } iconx = newzeromatrix(num_cal_points,1);
   icony = newzeromatrix(num_cal_points,1);
   dxm = newzeromatrix(num_cal_points,1);
   dym = newzeromatrix(num_cal_points,1);
   if ((iconx == NULL) || (icony == NULL) || (dxm == NULL) || (dym == NULL)) {
       fprintf(stderr,"Memory Allocation Failure -- Not Enough Room for Matrices\n");
       exit(0);
   } init_graph_needs(iconx,icony);
   place_icon(0.5 * getmaxx(),0.5 * getmaxy());
continuous();
newgrabnswitch();
continuous();
newgrabnswitch();
/*   grabframe();*/
   setthresholds();
   remove_icon(0.5 * getmaxx(),0.5 * getmaxy());
   for (index = 0; index < num_cal_points; index++) {
       place_icon(elem(iconx,index,0),elem(icony,index,0));
/*     grabframe(); */       /* Make Sure the IVM will have a good image */
/*     newgrabnswitch();*/
       if(!get_deltas(&dx,&dy,&thpd,&tvpd,5.0)) {
           freeMatrix(dxm); freeMatrix(dym); freeMatrix(iconx); freeMatrix(icony);
           return(0);
       }
       else { elem(dxm,index,0) = dx;
              elem(dym,index,0) = dy;
            }
       remove_icon(elem(iconx,index,0),elem(icony,index,0));
   }
   if(!gen_coeffs(mx,my,iconx,icony,dxm,dym)) {
      freeMatrix(dxm); freeMatrix(dym); freeMatrix(iconx); freeMatrix(icony);
      return(0);
   }
   if (!goodcal(mx,my,iconx,icony,dxm,dym)) {
      freeMatrix(dxm); freeMatrix(dym); freeMatrix(iconx); freeMatrix(icony);
      return(0);
```

```
    }
    freeMatrix(dxm); freeMatrix(dym); freeMatrix(iconx); freeMatrix(icony);
    return(1);
}

/* AUTHOR: Kevin S. Spetz
 * DATE: 7/88
 * Routine takes care of the screen and then call cal. Will quit to DOS
 * if 'q' pressed. Returns success if a succesful calibration is
 * completed.
 */
unsigned calibrate(Matrix *mx,Matrix *my)
{   char scrbuf[80*25*2];
    void * buffer;
    unsigned size;
    int sm;
    unsigned success;
    int cur;

/*    continuous();*/
    clearmatrix(mx);
    clearmatrix(my);
                                        /* Want to find out what type of screen
                                         * we have before saving the screen and
                                         * performing a recalibration
                                         */
    switch(screen_mode()) {             /* Calibration called from text screen
                                         * Must save text and establish graphics
                                         * screen and calibrate. Text restored
                                         */
        case TEXT     : gettext(0,0,79,24,scrbuf);
                        cur = getcursor();
                        textbackground(BLACK);
                        clrscr();
                        show_cal_msg();
                        setupgraphics(EGA,EGAHI);
                        success = cal(mx,my);
                        closegraph();
                        puttext(0,0,79,24,scrbuf);
                        if (kbhit())
                            if (toupper(getch()) == 'Q') exit(0);
                        setcursor(cur);
                        break;
                                        /* Calibrate called from Graphics screen
                                         * with one page of memory. Graphics
                                         * screen saved and calibration performed.
                                         * Graphics restored.
                                         */
        case ONE_PAGE : size = imagesize(0,0,getmaxx(),getmaxy());
                        if ((buffer = malloc(size)) == NULL) {
                            fprintf(stderr,"Memory Allocation Error -- Not Enough Memory for Screen\n");
                            exit(0);
                        }
                        getimage(0,0,getmaxx(),getmaxy(),buffer);
                        sm = getgraphmode();
                        restorecrtmode();
                        textbackground(BLACK);
                        clrscr();
                        show_cal_msg();
                        setgraphmode(sm);
                        success = cal(mx,my);
                        putimage(0,0,buffer,COPY_PUT);
                        free(buffer);
                        if (kbhit())
                            if (toupper(getch()) == 'Q') exit(0);
                        break;
                                        /* Calibration called from Graphics screen
                                         * with two pages of memory. Assuming
                                         * second graphics screen free. Switch
                                         * pages and calibrate
                                         * Pages swithched back
                                         */
        case TWO_PAGES : setactivepage(1);
                         setvisualpage(1);
                         cleardevice();
                         getpalette(&curpalette);
                         setallpalette(&regpalette);
                         show_ega_cal_msg();
                         cleardevice();
                         success = cal(mx,my);
                         setallpalette(&curpalette);
                         setactivepage(0);
                         setvisualpage(0);
                         if (kbhit())
                            if (toupper(getch()) == 'Q') exit(0);
                         break;
    }
continuous();
    return(success);
}

/* AUTHOR: Kevin S. Spetz
 * DATE: 7/88
 * Routine called externally to setup the function of the gaze routines.
```

```
 * Manage the calibration matrix memory, the running filter, etc.
 */
void initgaze(int xr, int yr, int numave, int numcal)
   { if (cal_coeffsx != NULL)
        freeMatrix(cal_coeffsx);
     if (cal_coeffsy != NULL)
        freeMatrix(cal_coeffsy);
     if ((cal_coeffsx = newzeromatrix(CAL_COSIZE,1)) == NULL) {
        fprintf(stderr,"Memory Allocation Error -- Initgaze : Making Coef Matrix\n");
        exit(0);
        }
     if ((cal_coeffsy = newzeromatrix(CAL_COSIZE,1)) == NULL) {
        fprintf(stderr,"Memory Allocation Error -- Initgaze : Making Coef Matrix\n");
        exit(0);
        }
     pupil.x = 256;
     pupil.y = 256;
     x_res = xr;                      /* Resolution X lookpoin is return in */
     y_res = yr;                      /* Resolution Y     "    "   "   " */
     num_cal_points = numcal;       , /* Specify the Number of Calibration points */
     if (filter_pos != NULL)
        filter_pos = kill_filter(filter_pos);
     if ((filter_pos = init_filter(numave)) == NULL) {
        fprintf(stderr,"Memory Allocation Failure -- initfilter");
        exit(0);
        }
     do_recalibrate = 1;              /* Want to start with a calibrate   */
     clearerrs();
   }

/* AUTHOR: Kevin S. Spetz
 * DATE: 12/88
 * Routine that forces a recalibration on the next call to getgazeposition
 */
void set_recalibrate(void)
    { do_recalibrate = 1;
    } void clear_recalibrate(void)
    { do_recalibrate = 0;
    }

/* AUTHOR: Kevin S. Spetz
 * DATE: 1/31/89
 * Routine that allows the user to set the X and Y resolution in which the
 * screen lookpoints are returned in,
 */
void set_gaze_res(int xr, int yr)
    { calmaxx = getmaxx();
      calmaxy = getmaxy();
      x_scale_fact = (double)xr / calmaxx;
      y_scale_fact = (double)yr / calmaxy;
      x_res = xr;
      y_res = yr;
    }

/* AUTHOR: Kevin S. Spetz
 * DATE: 1/18/89
 * Routine sets the showcalpoints variable to on or off. When on the
 * calibration routines will display the calibration points and the
 * corresponding calculated lookpoints on the screen, pause for 3 seconds
 * and continue. The default is off. If on = 0, calibration results are
 * not shown, they are shown otherwise.
 */
void show_cal(int on)
    { showcalpoints = on;
    }

/* AUTHOR: Kevin S. Spetz
 * DATE: 7/88
 * Routine called externally to read an x and y lookpoint and the pupil
 * diameter
 */
unsigned getgazeposition(int *x, int *y,int *hpupdia, int *vpupdia)
   { double dx,dy;
     unsigned done;
     int temp_x;
     int temp_y;

do {
       if (do_recalibrate) {
          while(!calibrate(cal_coeffsx,cal_coeffsy));
          do_recalibrate = 0;
          }
       done = 0;
       if (get_deltas(&dx,&dy,hpupdia,vpupdia,1)) {
          filter_pos = lp_filter(filter_pos,&dx,&dy);
          *x = (int)(x_scale_fact * calc_lp(cal_coeffsx,dx,dy));
          *y = (int)(y_scale_fact * calc_lp(cal_coeffsy,dy,dx));
          done = 1;
```

```
            }
        else return(0);
        } while (!done);
/*
output_file=fopen("crash.dat","a");
fprintf (output_file,"x:%d y:%d\n",*x,*y);
fclose(output_file);
*/
    temp_x=*x;
    temp_y=*y;
    if ((temp_x > 0) && (temp_x < x_res) && (temp_y > 0) && (temp_y < y_res+100 ))
        {
        return(1);
        }
    else
        {
        *x = 1;
        *y = 1;
        return(0);
        }
    } void save_cal(void)
    {
    dupMatrix(cal_coeffsx, &oldcalcoeffsx);
    dupMatrix(cal_coeffsy, &oldcalcoeffsy);
    } void restore_cal(void)
    {
    dupMatrix(oldcalcoeffsx, &cal_coeffsx);
    dupMatrix(oldcalcoeffsy, &cal_coeffsy);
    clear_recalibrate();
    freeMatrix(oldcalcoeffsx);
    freeMatrix(oldcalcoeffsy);
    oldcalcoeffsx = NULL;
    oldcalcoeffsy = NULL;
    } unsigned eval_calibrate(void)
    {
    return(calibrate(cal_coeffsx, cal_coeffsy));
    }
\032
``` tools.c

```
#define ULCORNER 0
#define URCORNER 1
#define LLCORNER 2
#define LRCORNER 3
#define HRZ_LINE 4
define VRT_LINE 5 include <conio.h>
include <stdlib.h>
#include <mem.h>
#include <dir.h>
#include <stdio.h>
#include <io.h>
#include <fcntl.h>
#include <dos.h>
#include <stdarg.h>
#include <alloc.h>
#include <ctype.h>
#include <string.h>
#include <graphics.h>
#include "c:\ericalib\tools.h"

static char boxmem[2][6] = {
    { 218,191,192,217,196,179},
    { 201, 187, 200, 188, 205, 186}
    };

static int linetype = DOUBLE;

static int allowtagging = 0;

/* AUTHOR: Kevin S. Spetz
 * DATE: 1/24/89
 *
 * Routine that extract the filename and extension from a path and returns
 * a pointer to that extracted string.  Uses fnsplit to do this.
 */
char *extract_fn(char *ext_fn, char *path)
    { char drive[MAXDRIVE], dir[MAXDIR], file[MAXFILE], ext[MAXEXT];
      fnsplit(path,drive,dir,file,ext);
      sprintf(ext_fn,"%s%s",file,ext);
      return(ext_fn);
    }

/* Routine which inquires to see in what mode the screen currently rests
```

```c
*/
screenmodes screen_mode(void)
    { union REGS regs;
      screenmodes sm;
      regs.h.ah = 0x0F;
      int86(0x10,®s,®s);
      switch(regs.h.al) {
          case 0x00 :
          case 0x01 :
          case 0x02 :
          case 0x03 :
          case 0x07 : sm = TEXT;
                      break;
          case 0x04 :
          case 0x05 :
          case 0x06 :
          case 0x08 :
          case 0x09 :
          case 0x0A :
          case 0x0B :
          case 0x0C :
          case 0x0D :
          case 0x0E :
          case 0x0F : sm = ONE_PAGE;
                      break;
          case 0x10 : sm = TWO_PAGES;
                      break;
        }
      return(sm);
    }

/* AUTHOR: Kevin S. Spetz
 * DATE: 11/16/88
 *
 * Routine to define the shape of the cursor
 */
void setcursor(unsigned int shape)
    { union REGS reg;

reg.h.ah = 1;
      reg.x.cx = shape;
      int86(0X10, ®, ®);
    }

/* AUTHOR: Kevin S. Spetz
 * DATE: 11/16/88
 *
 * Routine to read the shape of the cursor
 */
unsigned int getcursor(void)
    { union REGS reg;

reg.h.ah = 3;
      int86(0X10, ®, ®);
      return(reg.x.cx);
    }

/* AUTHOR: Kevin S. Spetz
 * DATE: 11/18/88
 *
 * Routine to read in a string from the keyboard.  The routine will use the
 * current forground and background color when showing what is typed.
 */
char *getstring(char *str)
    { char c;
      char *s;
      int done = 0;
      int x,y;

s = str;
      x = wherex();
      y = wherey();
      setcursor(SHORT_CURSOR);
      do {
          c = getch();
          if ((c > 31) && (c < 127)) {
              *s++ = c;
              *s = 0;
              gotoxy(x,y);
              cprintf("%s",str);
            }
          if (c == RET) {
              *s = 0;
              done = 1;
            }
          if ((c == BCKSP) && (s > str)) {
              *--s = 0;
              gotoxy(x,y);
              clreol();
              cprintf("%s",str);
            }
        } while (!done);
      setcursor(NO_CURSOR);
      return(str);
    }
```

```c
/* AUTHOR: Kevin Spetz (adapted from the TurboC Microcalc program)
 * DATE: 8/7/89
 *
 * Routine accepts the string input s, and allows a user to edit that string.
 * The string legal defines which characters are legal input for the string s.
 * If legal is an empty string, then all characters are legal. The string s
 * can be no longer than maxlength. If the first character entered is an
 * editing command, then the old value of s is maintained, and the user may
 * edit it. If a character is the first string, then the old string is
 * erased, and the user starts fresh. Insert and typeover modes are supported
 */
unsigned editstring(char *s, char *legal, int maxlength)
  { int c, len = strlen(s), pos = len, insert = 1;
    int oldcursor = getcursor(), firstchar = 1;
    int x = wherex(), y = wherey(), fgc = getfgc(), bgc = getbgc();
    setcursor(TALL_CURSOR);
    fastwrite(x,y,bgc | 0x08,fgc & 0x07,s);   /* Inverse video before first char */
    do {
      gotoxy(pos + x, y);
      switch(c = getch()) {
        case 0 :
          switch(c = getch()) {
            case RtArrow :
              if (pos < len)
                pos++;
              break;
            case LfArrow :
              if (pos > 0)
                pos--;
              break;
            case Home :
              pos = 0;
              break;
            case End :
              pos = len;
              break;
            case Del :
              if (pos < len) {
                movmem(&s[pos + 1], &s[pos], len - pos);
                len--;
                }
              break;
            case Insert :
              insert = !insert;
              if (insert) setcursor(TALL_CURSOR);
              else setcursor(SHORT_CURSOR);
              break;
            }
          break;
        case BCKSP :
          if (pos > 0) {
            movmem(&s[pos], &s[pos - 1], len - pos + 1);
            pos--;
            len--;
            }
          break;
        case RET :
          break;
        case ESC :
          len = 0;
          break;
        default :
          if (firstchar) {
            gotoxy(x,y);
            clreol();
            len = 0;
            pos = 0;
            s[0] = 0;
            }
          if (((legal[0] == 0) || (strchr(legal,c) != NULL)) &&
              ((c >= ' ') && (c <= '~')) && ((len < maxlength) ||
              ((pos < len) && (!insert)))) {
            if (insert) {
              memmove(&s[pos + 1], &s[pos], len - pos + 1);
              len++;
              }
            else if (pos >= len)
                    len++;
            s[pos++] = c;
            }
          break;
        }
      s[len] = 0;
      fastwrite(x,y,fgc,bgc,s);
      fastwrite(x + len, y, fgc, bgc," ");
      firstchar = 0;
      } while ((c != RET) && (c != ESC));
    setcursor(oldcursor);
    return(c != ESC);
  }

/* AUTHOR: Kevin S. Spetz
 * DATE: 11/16/88
 *
 * Routine returns the current background color at the cursor position
 */
```

```c
unsigned xybgcolor(void)
    { union REGS regs;
      unsigned bgc;
      regs.h.ah = 0x08;
      regs.h.bh = 0x00;
      int86(0x10,®s,®s);
      bgc = (regs.h.ah & 0x70) >> 4;
      return(bgc);
    } unsigned getfgc(void)
    { struct text_info t;
      gettextinfo(&t);
      return(t.attribute & 0x0F);
    } unsigned getbgc(void)
    { struct text_info t;
      gettextinfo(&t);
      return((t.attribute & 0x70) >> 4);
    }

/* AUTHOR: Kevin S. Spetz
 * DATE: 8/12/88
 *
 * Routine prints a string at the specified xy location in the specified
 * color
 */
void xycprintf(int x, int y, int color, char *st,...)
    { struct text_info ti;
      char lst[128];
      va_list argptr;

gettextinfo(&ti);
      gotoxy(x,y);
      textcolor(color);
      textbackground(xybgcolor());
      va_start(argptr,st);
      vsprintf(lst,st,argptr);
      va_end(argptr);
      cprintf("%s",lst);
      textattr(ti.attribute);
    }

/* AUTHOR: Kevin S. Spetz
 * DATE:
 * Routine which prompts a user with the string *st and expects the user to
 * respond by entering an interger.
 */
int getnum(int x, int y, int color, char *st)
    { char temp[10] = "";
      int h;
      gotoxy(x,y);
      textcolor(color);
      cprintf("%s",st);
      editstring(temp,"0123456789",10);
      sscanf(temp,"%d",&h);
      return(h);
    }

/* AUTHOR: Kevin S. Spetz
 * DATE:
 * Routine which writes a string in the colors fgc, and bgc.  The string is
 * written at the point x, y and is directly written to screen memory.
 * FAST, FAST!!!!  Does not obey TC text window confines.
 */
void fastwrite(int x, int y, int fgc, int bgc, unsigned char *st)
    { unsigned screenseg, offset;
      unsigned char attr;
      struct text_info ti;
      int far *screenloc;

if ((peekb(0000,1040) & 48) != 48)
          screenseg = 0xB800;
      else screenseg = 0xB000;
      attr = (bgc << 4) | fgc;
      gettextinfo(&ti);
      offset = ((ti.winleft - 1 + x - 1) * 2) + ((ti.wintop - 1 + y - 1) * 160);
      screenloc = (int far *) MK_FP(screenseg,offset);
      while(*st != 0)
          *screenloc++ = (attr << 8) | *st++;
    }

/* AUTHOR: Kevin S. Spetz
 * DATE: 11/16/88
 *
 * Routine puts count number of chars at the location xy in the colors fgc
 * and bgc
 */
void cputchar(int x ,int y, unsigned char fgc, unsigned char bgc,unsigned char count, unsigned char c)
    { long screenseg, offset;
      int j;
      short attr;
      struct text_info ti;
```

```c
    if ((peekb(0000,1040) & 48) != 48)
        screenseg = 0xB800;
    else screenseg = 0xB000;
    attr = (bgc << 4) | fgc;
    gettextinfo(&ti);
    for (j = 0; j < count; j++) {
        offset = ((j + ti.winleft - 1 + x - 1) * 2) + ((ti.wintop - 1 + y - 1) * 160);
        pokeb(screenseg,offset++,c);
        pokeb(screenseg,offset,attr);
        }
    }

/* AUTHOR: Kevin S. Spetz
 * DATE: 11/16/88
 *
 * Routine to automatically put the attribute created by fgc and bgc in
 * the screen memory locations starting at x,y and extending to x+count,y.
 * The routine does not affect the characters on the screen.
 */
void cputattr(int x, int y, unsigned char fgc, unsigned char bgc, int count)
    { long screenseg, offset;
    int j;
    short attr;
    struct text_info ti;

if ((peekb(0000,1040) & 48) != 48)
        screenseg = 0xB800;
    else screenseg = 0xB000;
    attr = (bgc << 4) | fgc;
    gettextinfo(&ti);
    for (j = 0; j < count; j++) {
        offset = ((j + ti.winleft + x - 1) * 2) + 1 + ((ti.wintop + y - 1) * 160);
        pokeb(screenseg,offset,attr);
        }
    }
/* AUTHOR: Kevin S. Spetz
 * DATE: 11/16/88
 *
 * Routine sets the attribute of the current text window to the attribute
 * defined by fgc and bgc
 */
void setattr(unsigned char fgc, unsigned char bgc)
    { long screenseg, offset;
    int i,j;
    unsigned char attr;
    struct text_info ti;
    unsigned char far *screenloc;    /* Char so we can address just the attribute */ if ((peekb(0000,1040) & 48) != 48)       /* Determine the correct screen */
        screenseg = 0xB800;                   /* address */
    else screenseg = 0xB000;
    gettextinfo(&ti);
    attr = (bgc << 4) | fgc;
    for (i = ti.wintop; i < ti.winbottom + 1; i++) {
        offset = ((ti.winleft - 1) * 2) + 1 + ((i - 1) * 160);
        screenloc = (unsigned char far *) MK_FP(screenseg,offset);
        for (j = ti.winleft; j < ti.winright + 1; j++) {
            *screenloc++ = attr;        /* Write attribute to screen memory */
            screenloc++;                /* Skip over the character location */
            }
        }
    }

/* AUTHOR: Kevin S. Spetz
 * DATE 6/29/89
 * Sets what type of line is used by the draw box routine, single or double
 */
void set_box_line(int lt)
    { linetype = lt;
    }

/* AUTHOR: Kevin S. Spetz
 * DATE: 11/16/88
 *
 * Routine draws a box with corners defined by ulx...lry in the colors fgc
 * and bgc. Setting shadow to 1 will float the box above the screen
 */
void draw_a_box (int ulx, int uly, int lrx, int lry, int fgc, int bgc, int shdw)
    { int i;
    struct text_info ti;
    gettextinfo(&ti);
    if (shdw) {                                    /* Set the shadow attributes */
        window(ulx + 2,uly + 1,lrx + 2,lry + 1);
        setattr(LIGHTGRAY,BLACK);
        }
    window(ulx,uly,lrx,lry);
    textbackground(bgc);
    clrscr();
    window(1,1,80,25);
    cputchar(ulx,uly,fgc,bgc,boxmem[linetype][HRZ_LINE]);
    cputchar(ulx,lry,fgc,bgc,lrx-ulx,boxmem[linetype][HRZ_LINE]);
    for (i = uly; i < lry; i++) {
```

```
        cputchar(ulx,i,fgc,bgc,1,boxmem[linetype][VRT_LINE]);
        cputchar(lrx,i,fgc,bgc,1,boxmem[linetype][VRT_LINE]);
        }
    cputchar(ulx,uly,fgc,bgc,1,boxmem[linetype][ULCORNER]);
    cputchar(lrx,uly,fgc,bgc,1,boxmem[linetype][URCORNER]);
    cputchar(ulx,lry,fgc,bgc,1,boxmem[linetype][LLCORNER]);
    cputchar(lrx,lry,fgc,bgc,1,boxmem[linetype][LRCORNER]);
    textattr(ti.attribute);
    }

/* AUTHOR: Kevin S. Spetz
 * DATE: 11/16/88
 *
 * Routine draws a box defined by ulx...lry in the colors fgc and bgc and
 * returns a pointer to a structure defining the characteristic of the window
 * the active text window is set inside the box such that 1,1 is just inside
 * the lines. The structure windowtype holds the xy coords of the corners,
 * a structure with the previous screen state information and a pointer to
 * a buffer with the screen that was under the window
 */
windowtype *open_window(int ulx, int uly, int lrx, int lry, int fgc, int bgc, int shadow,char *format,.
..)
    { va_list argptr;
      char pbuf[128];
      int dummy;
      windowtype *win;
      if ((win = (windowtype *) malloc(sizeof(windowtype))) == NULL) {
          fprintf(stderr,"Error! 1 Memory allocation failure -- open_window");
          exit(0);
          }
      if ((win->prevscrn = (void *) malloc((lrx - ulx + 3) * (lry - uly + 2) * 2)) == NULL) {
          fprintf(stderr,"Error! 2 Memory allocation failure -- open_window");
          exit(0);
          }
      win->ulx = ulx;
      win->uly = uly;
      if (shadow) {
          win->lrx = lrx + 2;
          win->lry = lry + 1;
          }
      else {
          win->lrx = lrx;
          win->lry = lry;
          }
      gettextinfo(&(win->ti));
      textcolor(fgc);
      textbackground(bgc);
      if (shadow)
          dummy = gettext(ulx,uly,lrx + 2,lry + 1,win->prevscrn);
      else
          dummy = gettext(ulx, uly, lrx, lry, win->prevscrn);
      draw_a_box(ulx,uly,lrx,lry,fgc,bgc,shadow);
      va_start(argptr,format);
      vsprintf(pbuf,format,argptr);
      if (strlen(pbuf) > 0)
          xycprintf(ulx + 1, uly, fgc," %s ",pbuf);
      va_end(argptr);
      window(ulx + 1, uly + 1, lrx - 1, lry - 1);
      return(win);
      }

/* AUTHOR: Kevin S. Spetz
 * DATE: 11/16/88
 *
 * Routine closes a window opened by open_window. Simply pass the name of
 * the opened window and close_window will replace the information under
 * the window and free all memory associated with the window
 */
void close_window(windowtype *win)
    { puttext(win->ulx,win->uly,win->lrx, win->lry, win->prevscrn);
      window(win->ti.winleft,win->ti.wintop,win->ti.winright,win->ti.winbottom);
      gotoxy(win->ti.curx,win->ti.cury);
      textattr(win->ti.attribute);
      free(win->prevscrn);
      free(win);
      }

/* AUTHOR: Kevin S. Spetz
 * DATE:
 * Routine which displays a lightly shades bar at the location x,y. The bar is
 * filled up to the percentage point indicated by cur/total.
 */
void percentbar(int x, int y, int len, long cur, long int total)
    { int b;
      static int lastperctg = 0;
      if (total > 0) {
b = (int)((float) len * ((float) cur/(float) total));
if (b != lastperctg) {
   cputchar(x,y,YELLOW,BLUE,b,'\333');
   cputchar(x + b,y,WHITE,BLUE,len - b,'-');
   xycprintf(x + len/2 - 4, y + 1, YELLOW,"%4.0f",(float) ( 100.0 * (float)cur/(float)total));
   xycprintf(wherex(), y + 1, WHITE,"%% done");
   lastperctg = b;
```

```
/* AUTHOR: Kevin S. Spetz
 * DATE:
 * Routine to check and see if a file exists
 */
int file_exists(char *st)
{   int han;
    if ((han = open(st,O_RDONLY)) != -1) {
        close(han);
        return(1);
        }
    return(0);
}

/* AUTHOR: Kevin S. Spetz
 * DATE: 5/15/89
 * Routine which takes the parameter *n and makes sure that it is not greater
 * than t or less than b.  If it is, *n is clipped to these boundaries.
 */
void bind (int *n, int b, int t)
{   if (*n < b)
        *n = b;
    else if (*n > t)
        *n = t;
}

/***************************************************************************
 ****************************************************************************
 *
 * Routines for showing a directory on the screen and selecting a file from
 * that directory.  These routines rely on the routines above that open
 * windows etc.
 ****************************************************************************
 ***************************************************************************/

/* AUTHOR: Kevin S. Spetz
 * DATE: 1/16/88
 *
 * Routine that scans the directory defined by filespec and returns a
 * pointer to a linked list of these filenames.  Also returns the number
 * of files in the directory
 */
static dirtype *getdirlist(char *filespec, int *numfiles)
{   int done;
    struct ffblk tmpffblk;
    dirtype *firstentry, *curentry, *tmpentry;
    char far *curdta;
    curdta = getdta();

done = findfirst(filespec,&tmpffblk,0);
    if (done) return(NULL);
    *numfiles = 1;
    if ((curentry = (dirtype *) malloc(sizeof(dirtype))) == NULL) {
        fprintf(stderr, "Error! Memory allocation -- getdirlist");
        exit(1);
        }
    firstentry = curentry;
    firstentry->nextentry = NULL;
    firstentry->tagged = 0;
    strcpy(firstentry->filename,tmpffblk.ff_name);
    while (!done) {
        tmpentry = curentry;
        if (((done = findnext(&tmpffblk))) == 0) {
            (*numfiles)++;
            if ((curentry = (dirtype *) malloc(sizeof(dirtype))) == NULL) {
                fprintf(stderr, "Error! Memory allocation -- getdirlist");
                exit(1);
                }
            tmpentry->nextentry = curentry;
            strcpy(curentry->filename,tmpffblk.ff_name);
            curentry->nextentry = NULL;
            curentry->tagged = 0;
            }
        }
    setdta(curdta);
    return(firstentry);
}

/* AUTHOR: Kevin S. Spetz
 * DATE: 1/16/88
 *
 * Routine that destroys the linked list containing the directory entries.
 * The linked list is created by the routine getdirlist
 */
void killdirlist (dirtype *dirlist)
{   dirtype *curentry, *nextentry;
    nextentry = dirlist->nextentry;
    curentry = dirlist;
    while (curentry != NULL) {
        free(curentry);
```

```c
         curentry = nextentry;
         nextentry = curentry->nextentry;
         }
  }

/* AUTHOR: Kevin S. Spetz
 * DATE: 1/16/88
 *
 * Routine that move the pointer to the directory list forward from the pointer
 * position startentry to the position startentry + num.  If the new location
 * is past the end of the list the routine returns a pointer to the last file
 * in the list
 */
static dirtype *moveplus_dir(dirtype *startentry,int num)
  { int count = 0;
    dirtype *curentry,*preventry;
    preventry = curentry = startentry;

while ((curentry->nextentry != NULL) && (count < num)) {
       preventry = curentry;
       curentry = curentry->nextentry;
       count++;
       }
    if (preventry->nextentry == NULL)
       return(preventry);
    else return(curentry);                /* Don't lose list if run into end */
  }

/* AUTHOR: Kevin S. Spetz
 * DATE: 1/16/88
 *
 * Routine that displays the directory dir starting at startnum and displaying
 * the files is a rectangular matrix defined by rows and cols
 */
#define COLOR  BLUE
static void showdir(dirtype *dir,int startnum, int cols, int rows)
   {  int col, row,done;
      dirtype *curentry;
      char t[15];

col = 0;
     row = 0;
     done = 0;
/*     clrscr();*/
     curentry = moveplus_dir(dir,startnum);
     while ((curentry != NULL) && (!done)) {
        sprintf(t,"%-12s",strlwr(curentry->filename));
        fastwrite(col * 15 + 2,row + 1,WHITE,COLOR,t);
        if (curentry->tagged)
           fastwrite(col*15+1,row + 1,WHITE,COLOR,"fl");
        if (++row > rows - 1) {
           row = 0;
           if (++col + 1 > cols) {
              done = 1;
              }
           }
        curentry = curentry->nextentry;
        }
   }

/* AUTHOR: Kevin S. Spetz
 * DATE:
 * Routine which extracts all the files in *dirlist which have been
 * "tagged".  The tagged list is returned in *maketaglist.
 */
static dirtype *maketaglist(dirtype *dirlist)
  { int done = 0;
    dirtype *firstentry, *curentry, *tmpentry;
    dirtype *tmplist;

tmplist = dirlist;
    while((!tmplist->tagged) && (tmplist->nextentry != NULL)) {
       tmplist = tmplist->nextentry;
       }
    if (tmplist->nextentry == NULL) {
       if (tmplist->tagged) {
          if ((firstentry = (dirtype *) malloc(sizeof(dirtype))) == NULL) {
             fprintf(stderr, "Error! Memory allocation -- maketaglist");
             exit(1);
             }
          return(firstentry);
          }
       else return(NULL);
       }
    if ((firstentry = (dirtype *) malloc(sizeof(dirtype))) == NULL {
       fprintf(stderr,"Error! Memory allocation -- maketaglist");
       exit(1);
       }
    firstentry->nextentry = NULL;
    strcpy(firstentry->filename,tmplist->filename);
    curentry = firstentry;
    while (!done) {
```

```
             tmplist = tmplist->nextentry;
             if ((tmplist->tagged) && (tmplist != NULL)) {
                tmpentry = curentry;
                if ((curentry = (dirtype *) malloc(sizeof(dirtype))) == NULL) {
                    fprintf(stderr,"Error! Memory allocation -- maketaglist");
                    exit(1);
                    }
                tmpentry->nextentry = curentry;
                strcpy(curentry->filename,tmplist->filename);
                curentry->nextentry = NULL;
                }
            if (tmplist == NULL) done = 1;
            }
        return(firstentry);
        }

/* AUTHOR: Kevin S. Spetz
 * DATE 2/29/89
 *
 * Routine which sets the allow tagging flag for the select file routine.
 * If tagging is allowed the routines will allow the user to press T when
 * highlighting a file and tag it.  When the select file routine is exited
 * all of the tagged files are returned in a list
 */
void setfiletagging(int stat)
    { allowtagging = stat;
    }

/* AUTHOR: Kevin S. Spetz
 * DATE: 1/16/88
 *
 *
 * Routine which displays a directory defined by filespec, and allows the
 * user to select a file with the arrow keys, etc.  The filename is returned
 * by the pointer filename.  The window used is defined by xstart, ystart,
 * rows and cols.  If all of the directory entries won't fit in the box,
 * the user can page up and down.
 */
#define COLOR1 LIGHTCYAN
#define COLOR2 CYAN
unsigned selectfile (char *filespec, char *filename, int *taglist, int xstart, int ystart, int cols, in
t rows)
    { windowtype *buf;
      dirtype *dirlist, *curentry;
      int numdirfiles;
      int startnum,row,col,done = 0;
      char efn[MAXFILE+MAXEXT],boxlab[64];

if (cols > 4) cols = 4;
      if (rows > 21) rows = 21;
      if (xstart + (16 * cols) + 3 > 80) xstart = 0;
      if (ystart + rows + 3 > 25) ystart = 0;
      if (cols > 2)
          strcpy(boxlab,filespec);
      else strcpy(boxlab,extract_fn(efn,filespec));
      buf = open_window(xstart,ystart,xstart + (cols * 15) + 1, ystart + rows + 1,COLOR1,COLOR2,1,boxla
b);

if ((dirlist = getdirlist(filespec,&numdirfiles)) == NULL) {
          fastwrite(1,1,WHITE,RED," No Entries ");
          getch();
          close_window(buf);
          strcpy(filename," ");
          return(0);
          }
      startnum = 0;
      row = 0;
      col = 0;
      showdir(dirlist,startnum, cols, rows);
      cputattr(col * 15 + 1, row, WHITE, RED, 13);
      while (!done) {
          switch(toupper(getch())) {
             case 0   : cputattr(col * 15 + 1, row, WHITE, COLOR2, 13);
                         switch (getch()) {
                             case UpArrow : if (--row < 0) {
                                                row = rows - 1;
                                                if (--col < 0) {
                                                    col = 0;
                                                    row = 0;
                                                    if (--startnum > -1)
                                                        showdir(dirlist,startnum,cols,rows);
                                                    else startnum = 0;
                                                    }
                                                }
                                             break;
                             case DnArrow : if (startnum + col * rows + ++row > numdirfiles - 1)
                                                row--;
                                             else if (row > rows - 1) {
                                                 if (++col > cols - 1) {
                                                     row--;
                                                     col--;
                                                     showdir(dirlist,++startnum,cols,rows);
                                                     }
                                                 else { row = 0;
                                                     }
```

```
                          break;
            case RtArrow : if (++col > cols - 1) {
                              col--;
                              if ((startnum = startnum + rows) > numdirfiles - 1) {
                                  startnum = startnum - rows;
                                  }
                              else { if (startnum + col * rows + row > numdirfiles - 1)
                                        if (--col < 0) {
                                            col++;
                                            startnum = startnum - rows;
                                            }
                                     clrscr();
                                     showdir(dirlist,startnum,cols,rows);
                                     }
                              }
                          else if (startnum + col * rows + row > numdirfiles - 1)
                              col--;
                          break;
            case LfArrow : if (--col < 0) {
                              col = 0;
                              if ((startnum = startnum - rows) < 1)
                                  startnum = 0;
                              showdir(dirlist,startnum,cols,rows);
                              }
                          break;
            case PgUp    : startnum = startnum - rows * cols;
                          if (startnum < 0)
                              startnum = 0;
                          row = 0;
                          col = 0;
                          clrscr();
                          showdir(dirlist,startnum,cols,rows);
                          break;
            case PgDn    : startnum = startnum + rows * cols;
                          if (startnum < numdirfiles) {
                              row = 0;
                              col = 0;
                              clrscr();
                              showdir(dirlist,startnum,cols,rows);
                              }
                          else startnum = startnum - rows * cols;
                          break;
            case Home    : col = 0;
                          row = 0;
                          break;
            case End     : col = cols - 1;
                          row = rows - 1;
                          if (startnum + col * rows + row > numdirfiles - 1) {
                              col = (numdirfiles - startnum - 1) / rows;
                              row = numdirfiles - startnum - (col * rows) - 1;
                              }
                          break;
            }
            cputattr(col * 15 + 1, row, WHITE, RED, 13);
            break;
     case 'T' : if (allowtagging) {
                  cputattr(col * 15 + 1, row, WHITE, COLOR2, 13);
                  curentry = moveplus_dir(dirlist,startnum + col * rows + row);
                  curentry->tagged = 1 - curentry->tagged;
                  if (curentry->tagged)
                     fastwrite(col*15+1,row + 1,WHITE,COLOR2,"n");
                  else fastwrite(col*15+1,row + 1,WHITE,COLOR2," ");
                  if (startnum + col * rows + ++row > numdirfiles - 1)
                     row--;
                  else if (row > rows - 1) {
                        if (++col > cols - 1) {
                            row--;
                            col--;
                            showdir(dirlist,++startnum,cols,rows);
                            }
                        else row = 0;
                        }
                  cputattr(col * 15 + 1, row, WHITE, RED, 13);
                  }
              break;
     case RET : done = 1;
                curentry = moveplus_dir(dirlist,startnum + col * rows + row);
                strcpy(filename,curentry->filename);
                break;
     case ESC : strcpy(filename," ");            /* Cancel file request */
                close_window(buf);
                killdirlist(dirlist);
                *taglist = 0;                    /* Set tag list to null */
                return(0);
     }
  }
  close_window(buf);
  *taglist = (int) maketaglist(dirlist);
  killdirlist(dirlist);
  return(1);
}

ChooseDirFile(char *filespec, char *filename, char *heading)
{
 int col=0;
```

```c
            int row=0;
            int done=0;
            int cols=1;
            int rows=19;
            int numfiles;
            int startnum=0;
            windowtype *fwin;
            dirtype *dirlist, *curentry;
            fwin = open_window(55,4,80,25,YELLOW,BLUE,0,heading);
            if ((dirlist = getdirlist(filespec,&numfiles)) == NULL) {
                fastwrite(1,1,WHITE,RED," No Entries ");
                getch();
                close_window(fwin);
                strcpy(filename," ");
                return(0);
            }
            showdir(dirlist,startnum,cols,rows);
            cputattr(1, row, WHITE, RED, 20);
            while (!done) {
                switch(toupper(getch())) {
                    case 0  : cputattr(1, row, WHITE, BLUE, 20);
                              switch (getch()) {
                                  case UpArrow : if (--row < 0) {
                                                     row = rows - 1;
                                                     if (--col < 0) {
                                                         col = 0; row = 0;
                                                         if (--startnum > -1)
                                                             showdir(dirlist,startnum,cols,rows);
                                                         else startnum = 0;
                                                     }
                                                 }
                                                 break;
                                  case DnArrow : if (startnum + col * rows + ++row > numfiles - 1)
                                                     row--;
                                                 else if (row > rows - 1) {
                                                     if (++col > cols - 1) {
                                                         row--; col--;
                                                         showdir(dirlist,++startnum,cols,rows);
                                                     }
                                                     else { row = 0;
                                                     }
                                                 }
                                                 break;
                                  case PgUp    : startnum = startnum - rows * cols;
                                                 if (startnum < 0)
                                                     startnum = 0;
                                                 row = 0; col = 0;
                                                 clrscr();
                                                 showdir(dirlist,startnum,cols,rows);
                                                 break;
                                  case PgDn    : startnum = startnum + rows * cols;
                                                 if (startnum < numfiles) {
                                                     row = 0;
                                                     col = 0;
                                                     clrscr();
                                                     showdir(dirlist,startnum,cols,rows);
                                                 }
                                                 else
                                                     startnum = startnum - rows * cols;
                                                 break;
                                  case Home    : col = 0;
                                                 row = 0;
                                                 break;
                                  case End     : col = cols - 1;
                                                 row = rows - 1;
                                                 if (startnum + col * rows + row > numfiles - 1) {
                                                     col = (numfiles - startnum - 1) / rows;
                                                     row = numfiles - startnum - (col * rows) - 1;
                                                 }
                                                 break;
                              }
                              cputattr(1, row, WHITE, RED, 20);
                              break;
                    case RET : done = 1;
                               curentry = moveplus_dir(dirlist,startnum + col * rows + row);
                               strcpy(filename,curentry->filename);
                               break;
                    case ESC : strcpy(filename," ");    /* Cancel file request */
                               killdirlist(dirlist);
                               close_window(fwin);
                               return(0);
                }
            }
    close_window(fwin);
    killdirlist(dirlist);
    return(1);
}

/*
main ()
    { int x;
    windowtype *buf;
    char f[64] = "";
    int fgc = 1, bgc;
    clrscr();
    fprintf(stdout,"Started with %u\n",coreleft());
```

```
    textbackground(BLACK);
    while(selectfile("c:\\saccade\\pictures\\*.pic",f,&fgc,5,5,2,14))
        fprintf(stderr,"%s\n",f);
    fprintf(stdout,"Ended with %u\n",coreleft());
}
*/\032
``` grtools.c

```c
include <stdio.h>
include <conio.h>
include <stdlib.h>
#include <math.h>
include <graphics.h> int fred;

struct linestruct {
   int x1, y1, x2, y2;
   unsigned *buf;
   };
typedef struct linestruct linetype;

int GraphDriver, GraphMode;

/* Routine to set up a graphics screen.  Set up to require an EGA card, can
 * be designed for autodetection.
 */
void setupgraphics(int GD, int GM)
   {  int errcode;
      GraphDriver = GD;
      GraphMode = GM;
      initgraph(&GraphDriver, &GraphMode,"c:\\turboc\\");
      errcode = graphresult();
      if (errcode != grOk)
         {  closegraph();
            textcolor(LIGHTRED);
            clrscr();
            cprintf("ERROR!, Encountered Graphics Error : %s",grapherrormsg(errcode));
            exit(1);
         }
   } void newsetupgraphics(int GD, int GM)
   {  int errcode;
      GraphDriver = GD;
      GraphMode = GM;

if (registerbgidriver(EGAVGA_driver) < 0)
      {
         fprintf (stderr,"Error with EGAVGA driver\n");
         exit(1);
      }
      initgraph(&GraphDriver, &GraphMode,"c:\\turboc\\");
      errcode = graphresult();
      if (errcode != grOk)
         {  closegraph();
            textcolor(LIGHTRED);
            clrscr();
            cprintf("ERROR!, Encountered Graphics Error : %s",grapherrormsg(errcode));
            exit(1);
         }
   }

/* AUTHOR: Kevin S. Spetz
 * DATE:
 * Routine to change the text style used by the graphics libraries. Checks for
 * errors.
 */
void changetextstyle(int font, int direction, int charsize)
   { int ErrorCode;

graphresult();                      /* clear error code     */
     settextstyle(font, direction, charsize);
     ErrorCode = graphresult();          /* check result         */
     if( ErrorCode != grOk ){            /* if error occured     */
        closegraph();
        printf(" Graphics System Error: %s\n", grapherrormsg( ErrorCode ) );
        exit(1);
     }
   } linetype *place_line(int x1, int y1, int x2, int y2, unsigned color)
      { int x, y, x_end, y_end, p, const1, const2, points;
        unsigned dx, dy;
        linetype *tmpbuf;
        unsigned *linebuf;

if ((tmpbuf = malloc(sizeof(linetype))) == NULL) {
```

```c
        fprintf(stderr,"Memory Allocation Error, place_line.\n");
        exit(1);
        }
    tmpbuf->x1 = x1; tmpbuf->x2 = x2; tmpbuf->y1 = y1; tmpbuf->y2 = y2;

dx = abs(x1 - x2);
    dy = abs(y1 - y2);

points = (int) sqrt(dx * dx + dy * dy);
    if ((linebuf = malloc(points * sizeof(unsigned))) == NULL) {
        fprintf(stderr,"Memory Allocation Error, place_line.\n");
        fprintf(stderr,"\tNot enough room for line buffer.\n");
        exit(1);
        }
    tmpbuf->buf = linebuf;

if (dx < dy) {
        p = 2 * dx - dy;
        const1 = 2 * dx;
        const2 = 2 * (dx - dy);
        if (y1 > y2) {
            y = y2; x = x2;
            y_end = y1;
            }
        else { x = x1; y = y1;
            y_end = y2;
            }
        *linebuf++ = (unsigned) getpixel(x,y);
        putpixel(x,y,color);
        fred = 1;
        while (y < y_end) {
            y++;
            if (p < 0) p+=const1;
            else { x++;
                p+=const2;
                }
            *linebuf++ = (unsigned) getpixel(x,y);
            putpixel(x,y,color);
            fred++;
            }
        }
    else { p = 2 * dy - dx;
        const1 = 2 * dy;
        const2 = 2 * (dy - dx);
        if (x1 > x2) {
            x = x2; y = y2;
            x_end = x1;
            }
        else { x = x1; y = y1;
            x_end = x2;
            }
        *linebuf++ = (unsigned) getpixel(x,y);
        putpixel(x,y,color);
        fred = 1;
        while (x < x_end) {
            x++;
            if (p < 0) p+=const1;
            else { y++;
                p+=const2;
                }
            *linebuf++ = (unsigned) getpixel(x,y);
            putpixel(x,y,color);
            fred++;
            }
        }
    return(tmpbuf);
    } void remove_line(linetype *line)
    { int dx, dy, x, y, x_end, y_end, p, const1, const2;
    int x1, x2, y1, y2;
    unsigned *linebuf;

x1 = line->x1; x2 = line->x2; y1 = line->y1; y2 = line->y2;
    linebuf = line->buf;

dx = abs(x1 - x2);
    dy = abs(y1 - y2);

if (dx < dy) {
        p = 2 * dx - dy;
        const1 = 2 * dx;
        const2 = 2 * (dx - dy);
        if (y1 > y2) {
            y = y2; x = x2;
            y_end = y1;
            }
        else { x = x1; y = y1;
            y_end = y2;
            }
        putpixel(x,y,*linebuf++);
        fred = 1;
        while (y < y_end) {
            y++;
            if (p < 0) p+=const1;
            else { x++;
```

```
                    p+=const2;
                    }
                putpixel(x,y,*linebuf++);
                fred++;
                }
            }
        else { p = 2 * dy - dx;
            const1 = 2 * dy;
            const2 = 2 * (dy - dx);
            if (x1 > x2) {
                x = x2; y = y2;
                x_end = x1;
                }
            else { x = x1; y = y1;
                    x_end = x2;
                }
            putpixel(x,y,*linebuf++);
            fred = 1;
            while (x < x_end) {
                x++;
                if (p < 0) p+=const1;
                else { y++;
                        p+=const2;
                        }
                putpixel(x,y,*linebuf++);
                fred++;
                }
            }
        }
    free(line->buf);
    free(line);
    }
\032
``` moustool.c

```c
include <stdio.h>
#include <stdlib.h>
#include <dos.h>
#include "c:\ericalib\tools.h"
#include "c:\ericalib\moustool.h"

static int arrow[] =
    { 0x3fff,0x1fff,0x0fff,0x07ff,0x03ff,0x01ff,0x00ff,0x007f,
      0x003f,0x001f,0x01ff,0x10ff,0x30ff,0xf87f,0xf87f,0xfc3f,
      0x0000,0x4000,0x6000,0x7000,0x7800,0x7c00,0x7e00,0x7f00,
      0x7f80,0x78c0,0x7c00,0x4600,0x0600,0x0300,0x0300,0x0180
    };

static int hour_glass[] =
    { 0x0000,0x0000,0x0000,0x0000,0x8001,0xc003,0xe007,0xf00f,
      0xe007,0xc003,0x8001,0x0000,0x0000,0x0000,0x0000,0xffff,
      0x0000,0xffff,0x8001,0x4002,0x27e4,0x13c8,0x0990,0x0990,
      0x0990,0x1188,0x23c4,0x4ff2,0x9ff9,0xffff,0x0000,0x0000
    };

static int pointing_hand[] =
    { 0xe1ff,0xe1ff,0xe1ff,0xe1ff,0xe1ff,0xe000,0xe000,0xe000,
      0x0000,0x0000,0x0000,0x0000,0x0000,0x0000,0x0000,0x0000,
      0x0c00,0x1200,0x1200,0x1200,0x1200,0x13fe,0x1249,0x5249,
      0xb249,0x9001,0x9001,0x9001,0x8001,0x8001,0x4002,0x3ffc
    };

void mouse(int m1, int m2, int m3, int m4)
    { union REGS regs;
    regs.x.ax = m1;
    regs.x.bx = m2;
    regs.x.cx = m3;
    regs.x.dx = m4;
    int86(0x33,®s,®s);
    } void pmouse(int *m1, int *m2, int *m3, int *m4)
    { union REGS regs;
    regs.x.ax = *m1;    regs.x.bx = *m2;
    regs.x.cx = *m3;    regs.x.dx = *m4;
    int86(0x33,®s,®s);
    *m1 = regs.x.ax;    *m2 = regs.x.bx;
    *m3 = regs.x.cx;    *m4 = regs.x.dx;
    } int mouse_installed(void)
    { union REGS regs;
    regs.x.ax = 0;
    int86(0x33,®s,®s);
    return(regs.x.ax);
    } void mouse_on(void)
    { mouse(1,0,0,0);
    } void mouse_off(void)
    { mouse(2,0,0,0);
    }
```

```
void set_mouse_cursor(int hotx, int hoty, int bitmap)
    { union REGS regs;
        regs.x.ax = 9;
        regs.x.bx = hotx;
        regs.x.cx = hoty;
        regs.x.dx = bitmap;
        _ES = _DS;
        int86(0x33,®s,®s);
    }
void set_mouse_shape(int sh)
    { switch(sh) {
        case ARROW :
            set_mouse_cursor(-1,-1,(int) arrow);
            break;
        case HOURGLASS :
            set_mouse_cursor(7,7,(int) hour_glass);
            break;
        case POINTINGHAND :
            set_mouse_cursor(5,-1,(int) pointing_hand);
            break;
        }
    } void get_mouse_position(int *mb, int *mx, int *my)
    { int m1;
        m1 = 3;
        pmouse(&m1,mb, mx, my);
    } void set_mouse_position(int mx, int my)
    { mouse(4,0,mx,my);
    } void mouse_button_presses(int button, int *bs, int *bc, int *bx, int *by)
    { int m1;
        m1 = 5;
        pmouse(&m1,&button,bx,by);
        *bc = button;
        *bs = m1;
    } void mouse_button_releases(int button, int *bs, int *bc, int *bx, int *by)
    { int m1;
        m1 = 6;
        pmouse(&m1,&button,bx,by);
        *bc = button;
        *bs = m1;
    } void set_mouse_hminmax(int hmin, int hmax)
    { mouse(7,0,hmin,hmax);
    } void set_mouse_vminmax(int vmin, int vmax)
    { mouse(8,0,vmin,vmax);
    } int get_mouse_click(int *mx, int *my)
    { int bc = 0, dummy = 0;
        mouse_button_releases(LEFTBUTTON,&dummy,&bc,mx,my);
        if (screen_mode() == TEXT) {
            *mx = *mx/8 + 1;
            *my = *my/8 + 1;
        }
        return(bc);
    } int mouse_rb_down(void)
    { int m1 = 3;
        int m2, m3, m4;
        pmouse(&m1,&m2,&m3,&m4);
        if (m2 & 0x2)
            return(1);
        else return(0);
    } int mouse_lb_down(void)
    { int m1 = 3;
        int m2, m3, m4;
        pmouse(&m1,&m2,&m3,&m4);
        if (m2 & 0x1)
            return(1);
        else return(0);
    }
\032
``` timex.c

```
#include <dos.h>
#include <stdio.h>
#include <stdlib.h>
#include "c:\ericalib\timex.h"
#define TIMER0 0x40
```

```c
#define CNTRL 0x43
#define READ_BACK 0xc2
#define BIOSSEG 0x40
#define TICS_LO 0x6c
define TICS_HI 0x6e define CONVERT_TM 18.643469 unsigned long timer(void)
{
 unsigned tmp1, tmp2, tmp3, tmp4, hi, lo;
 int status;
 unsigned far *add1;
 unsigned far *add2;
 long ticks1, ticks2;

add1=(unsigned far *) (BIOSSEG * 16 + TICS_LO);
 add2=(unsigned far *) (BIOSSEG * 16 + TICS_HI);

disable();
 outp (CNTRL,READ_BACK);
 status=inp(TIMER0);
 lo=(unsigned)inp(TIMER0);
 hi=(unsigned)inp(TIMER0);

tmp1=(unsigned) *add1;
 tmp2=(unsigned) *add2;
 enable();

hi=hi << 2 | lo >> 6;

disable();
 tmp3=(unsigned) *add1;
 tmp4=(unsigned) *add2;
 enable();

if ( !(lo & 63) ) hi--;
 hi=(-hi & 1023) >> 1;
 if (!(status & 128)) hi |=512;

ticks1=(long)tmp2<<16 | tmp1;
 ticks2=(long)tmp4 <<16 |tmp3;

if (ticks2 > ticks1 +1) return(-1);

if (hi & 512) return(ticks1<<10 | hi);
 else return (ticks2<<10 | hi);

} float timex(void)
{ unsigned long temp_clk;
  float time_clk;

temp_clk = timer();
  time_clk = (float)temp_clk/CONVERT_TM;
  return(time_clk);
}

/*
main()
{
unsigned long ztime, etime;
float elapsed;
int random_num;

printf ("program begins...\n");

while (1)
  {
  printf ("press ENTER to start timing\n");
  getchar();
  random_num=random(30)*100;
  ztime=timex();
  delay(random_num);
  etime=timex();

if (ztime<0 || etime < 0) break;
  printf ("delay:%d\n",random_num);

etime-=ztime;
  elapsed=(float)etime/18.643469;
  printf ("time was %f ms \n",elapsed);

}
  printf ("timing error\n");
}
*/\032
``` imagebox.c

```
/************************************************************
 *                                                          *
 *  BOX DEFINITION ROUTINES FOR DEFINING IMPORTANT REGIONS  *
 *                                                          *
 *  OVER A LOADED IMAGE SCREEN.                             *
 *                                                          *
 *  AUTHOR:  Nirav R. Desai                                 *
 *  DATE:    7/28/90-8/15/90                                *
 *                                                          *
 *                                                          *
 ************************************************************/ include <stdio.h>
include <dos.h>
#include <alloc.h>
#include <stdlib.h>
#include <conio.h>
#include <string.h>
#include <io.h>
#include <fcntl.h>
#include <dir.h>
#include <sys\stat.h>
/*#include <stdarg.h>
#include <ctype.h>
#include <math.h>*/
#include <graphics.h>
#include "c:\cgaze\fgroutns.h"
#include "c:\cgaze\gaze.h"
#include "c:\ericalib\tools.h"
#include "c:\ericalib\grtools.h"
#include "c:\ericalib\menu.h"
#include "c:\ericalib\moustool.h"
#include "c:\ericalib\timex.h"
#include "c:\maryland\imagebox.h"
#include "c:\maryland\sacimprc.h"
#include "c:\maryland\sacresul.h"
#include "c:\maryland\saccade.h"
include "c:\maryland\sacboxes.h"   /* Was saccade\sacboxes.h*/ typedef char menulabel[20];

menulabel box_def_menu[6] = {"Clear a Box","Save Box File","Edit Box File",
                              "Define a Box","Show a Box", "Quit"};
activeboxtype *boxdef_boxes = NULL;
int colors[6] = {EGA_LIGHTGREEN, EGA_LIGHTRED, EGA_CYAN,
                 EGA_YELLOW, EGA_LIGHTBLUE, EGA_BROWN};

boxdeftype image_boxes[MAX_BOXES];

void set_boxdef_boxes(void)
{   int i, x, y;
    for (i = 0; i < 6; i++) {
        x = (i%3)*215;
        y = (i%6)<3 ? 0: 35;
        if (boxdef_boxes == NULL)
            boxdef_boxes = start_activebox(i+1,x,y,x+208,y+32);
        else add_activebox(boxdef_boxes,i+1,x,y,x+208,y+32);
    }
} void init_image_boxes(void)
{ int i;
  for (i = 1; i<=MAX_BOXES; i++) {
      image_boxes[i-1].ul.x = -1;
      image_boxes[i-1].ul.y = -1;
      image_boxes[i-1].br.x = -1;
      image_boxes[i-1].br.y = -1;
  }
}

/* AUTHOR: Nirav R. Desai
 * DATE:   7/27/90
 * Draws a box using the predefined graphics function "rectangle"
 * and labels the box with the specified menulabel.
 */
void Draw_a_Box (int x1, int y1, int box_color, char *menulabel)
{
    setcolor(box_color);
    rectangle(x1,y1,x1+208,y1+32);
    setcolor(EGA_WHITE);
    outtextxy(x1+105,y1+16,menulabel);
}

/* AUTHOR: Nirav Desai
 * DATE:   7/27/90
 * Routine which presents menu choices to user for defining
 * boxes on the screen image. Uses mouse input.
 */
```

```c
void show_boxdef_choices(void)
{   int x,y,i;
    setfillstyle(SOLID_FILL, BLACK);
    bar(0,0,640,100);
    settextjustify(CENTER_TEXT,CENTER_TEXT);
    settextstyle(SMALL_FONT,HORIZ_DIR,6);
    for (i=0; i<=5; i++) {
        x=(i%3)*215;
        y=(i%6)<3 ? 0 : 35;
        Draw_a_Box(x,y,colors[i],box_def_menu[i]);
    }
} static int boxchoice(activeboxtype *abl, int x, int y)
{   activeboxtype *tmpb;
    tmpb = abl;
    while (tmpb != NULL) {
        if ((x > tmpb->ulx) && (x < tmpb->lrx) && (y > tmpb->uly)
            && (y < tmpb->lry) && (tmpb->enable))
            return(tmpb->num);
        tmpb = tmpb->next;
    }
    return(0);
}

/* AUTHOR: Nirav Desai
 * DATE:   7/27/90
 * Routine which uses mouse input to determine selection from boxdef_menu.
 */
int get_boxdef_choice(activeboxtype *abl)
{   int x, y, curbox;

setfillstyle(SOLID_FILL,EGA_BLACK);
    settextstyle(SMALL_FONT,HORIZ_DIR,4);
    settextjustify(LEFT_TEXT,CENTER_TEXT);
    bar(0,70,639,95);
    outtextxy(0,75,"Select a choice from the menu above.");
    set_mouse_shape(POINTINGHAND);
    mouse_on();
    x = -1;
    y = -1;
    while(!(curbox = boxchoice(abl,x,y))){
        while (!get_mouse_click(&x,&y)){ }
    }
    mouse_off();
    return(curbox);
}

/* AUTHOR: Nirav Desai
 * DATE:   7/27/90
 * Routine allows user to define corners of box areas on a graphics
 * screen using a mouse interface.
 */
void get_mouse_pos(unsigned int *xpos, unsigned int *ypos)
{   int x_pos, y_pos;
    set_mouse_shape(POINTINGHAND);
    mouse_on();
    x_pos = -1;
    y_pos = -1;
    while (!get_mouse_click(&x_pos,&y_pos)){ }
    /*printf("xpos = %d, ypos = %d\n",x_pos, y_pos);*/
    mouse_off();
    *xpos = x_pos;
    *ypos = y_pos;
}

/* AUTHOR: Nirav R. Desai
 * DATE:   8/2/90
 * Routine displays MAX_BOXES boxes, each containing a number between
 * must_choose(0 or 1) and MAX_BOXES, inclusive. User uses the mouse
 * to select which box number he wishes to clear, define, or show, as
 * defined by *msg.
 */
int choose_box_num(char *msg, int must_choose)
{   int i, box;
    div_t n;
    char ch[3];

unsigned int boxx=0, boxy=0;
    settextstyle(SMALL_FONT,HORIZ_DIR,4);
    setcolor(EGA_WHITE);
    setfillstyle(SOLID_FILL, EGA_BLACK);
    bar(0,70,639,95);
    settextjustify(LEFT_TEXT,CENTER_TEXT);
    outtextxy(0,75,msg);
    settextjustify(CENTER_TEXT,CENTER_TEXT);
    for(i=must_choose; i<=MAX_BOXES; i++) {
        rectangle(i*40,80,(i+1)*40-1,94);
        outtextxy(i*40+20,87,itoa(i,ch,10));
```

```c
    }
    while( boxx>((MAX_BOXES+1)*40) ||
        boxx<(must_choose*40) || boxy <80 || boxy>94) {
        get_mouse_pos(&boxx,&boxy);
    }
    n = div(boxx,40);
    box = n.quot;
    bar(0,70,639,95);
    settextjustify(LEFT_TEXT,CENTER_TEXT);
    return(box);
} void open_file(char *pathname)
{   char drive[MAXDRIVE], dir[MAXDIR], box_file[MAXFILE],ext[MAXEXT];
    int i;
    char ch;
    char temppath[MAXPATH];
    /*printf("Input the name of the box file (XXXX.BOX): ");
    gets(box_file);*/
    bar(0,70,639,95);
    settextjustify(LEFT_TEXT,CENTER_TEXT);
    outtextxy(0,75,"Input the name of the box file: ");
    i = 0;
    do {
        temppath[i] = ch = (char) getch();
        temppath[i+1] = '\0';
        bar(200,70,639,95);
        outtextxy(200,75,(char *)temppath);
        i++;
    } while(ch != '\r' && ch !='\n' && ch != ' ' && i<MAXPATH);
    *(temppath+i-1) = '\0';
    fnsplit(temppath,drive,dir,box_file,ext);

if(strlen(drive)==0) strcpy(drive,"C:");
    if(strlen(dir)==0)   strcpy(dir,"\\SACCADE\\BOX\\");
    if(strlen(ext)==0)   strcpy(ext,".BOX");
    fnmerge(pathname,drive,dir,box_file,ext);
} void save_box_file(void)
{   char pathname[MAXPATH];
    FILE *outfile;
    int i;

open_file(pathname);
    outfile = fopen(pathname,"w");
    if(outfile < 0) {
        perror("System error encountered");
        exit(1);
    }
    else {
        fprintf(outfile,"%s\n",BOXMARK);
        for (i=1; i<=MAX_BOXES; i++) {
            fprintf(outfile,"%d %d %d %d\n",image_boxes[i-1].ul.x,
                                            image_boxes[i-1].ul.y,
                                            image_boxes[i-1].br.x,
                                            image_boxes[i-1].br.y);
        }
    }
    fclose(outfile);
} void edit_box_file(void)
{   char pathname[MAXPATH];
    int i;
    FILE *infile;
    markertype marker;

open_file(pathname);
    infile = fopen(pathname,"r");
    if(infile < 0) {
        perror("System error encountered");
        exit(1);
    }
    else {
        fscanf(infile,"%s\n",marker);
        for (i=1; i<=MAX_BOXES; i++) {
            fscanf(infile,"%d %d %d %d\n",&image_boxes[i-1].ul.x,
                                          &image_boxes[i-1].ul.y,
                                          &image_boxes[i-1].br.x,
                                          &image_boxes[i-1].br.y);
        }
    }
    fclose(infile);
} void *show_corner(int x, int y, int color)
{   void *s;
    setcolor(color);
    bind(&x,0,635);
    bind(&y,5,345);
    s = malloc(imagesize(max(0,x - 4), y - 4, x + 4, y + 4));
```

```c
        getimage(max(0,x - 4), y - 4, x + 4, y + 4, s);
        line(x-4,y,x+4,y);
        line(x,y-4,x,y+4);
        return(s);
} void remove_corner(int x, int y, void *s)
{
    bind(&x,0,635);
    bind(&y,5,345);
    putimage(max(0,x - 4), y - 4, s, COPY_PUT);
    free(s);
} void remove_box(int x1, int y1, int x2, int y2, unsigned int *rect, int wait)
{   int i;
    unsigned int *rectptr, dummyx, dummyy;
    char message[81];
    if (wait) {
        sprintf(message,"ulx:%d  uly:%d  brx:%d  bry:%d   Click mouse to remove box from screen\n",x1,y1,x2,y2);
        bar(0,70,639,95);
        outtextxy(0,75,message);
        get_mouse_pos(&dummyx, &dummyy);
    }
    rectptr = rect;
    for (i=x1; i<x2; i++) {
        putpixel(i,y1,*rectptr);
        *rectptr++;
    }
    for (i=y1; i<y2; i++) {
        putpixel(x2,i,*rectptr);
        *rectptr++;
    }
    for (i=x2; i>x1; i--) {
        putpixel(i,y2,*rectptr);
        *rectptr++;
    }
    for (i=y2; i>y1; i--) {
        putpixel(x1,i,*rectptr);
        *rectptr++;
    }
} unsigned int *show_box(int x1, int y1, int x2, int y2, int color)
{   unsigned int *rect, *rectptr;
    unsigned int boxsize;
    int i;
    setcolor(color);
    bind(&x1,0,635);
    bind(&y1,5,345);
    bind(&x2,0,635);
    bind(&y2,5,345);
    boxsize = ((x2-x1)*2) + ((y2-y1)*2);
    rect = (unsigned int *) malloc(boxsize*sizeof(unsigned int));
    if (!rect) { closegraph();
            printf("Not enough memory to store boxes\n");
            exit(1);
            }
    rectptr = rect;
    for (i=x1; i<x2; i++) {
        *rectptr = getpixel(i,y1);
        putpixel(i,y1,color);
        *rectptr++;
    }
    for (i=y1; i<y2; i++) {
        *rectptr = getpixel(x2,i);
        putpixel(x2,i,color);
        *rectptr++;
    }
    for (i=x2; i>x1; i--) {
        *rectptr = getpixel(i,y2);
        putpixel(i,y2,color);
        *rectptr++;
    }
    for (i=y2; i>y1; i--) {
        *rectptr = getpixel(x1,i);
        putpixel(x1,i,color);
        *rectptr++;
    }
    return(rect);
} void clear_box(void)
{   int box;
    char message[81];
    unsigned int *boxptr;
    if ((box = choose_box_num("Click on the number of the box you wish to erase [0 to quit]:",0))!=0) {
        if (image_boxes[box-1].ul.x == -1) {
            bar(0,70,639,95);
            sound(400);
            sprintf(message,"Box %d is already clear\n",box);
            outtextxy(0,75,message);
```

```
            delay(1000);
            nosound();
            bar(0,70,639,95);
            return;
        }
        else{
            boxptr = show_box(image_boxes[box-1].ul.x,image_boxes[box-1].ul.y,
                        image_boxes[box-1].br.x,image_boxes[box-1].br.y,
                        EGA_WHITE);
            delay(500);
            remove_box(image_boxes[box-1].ul.x,image_boxes[box-1].ul.y,
                    image_boxes[box-1].br.x,image_boxes[box-1].br.y,
                    boxptr,0);
            free(boxptr);
            image_boxes[box-1].ul.x = -1;
            image_boxes[box-1].ul.y = -1;
            image_boxes[box-1].br.x = -1;
            image_boxes[box-1].br.y = -1;
        }
    }
} void define_a_box(void)
{   int box;
    unsigned int x1=1, y1=1, x2=0, y2=0;
    void *cl;
    char message[81];
    unsigned int *boxptr;
    if ((box = choose_box_num("Click on the number of the box you wish to define [0 to quit]:",0))!=0) {
        while(x1>=x2 || y1>=y2) {
            bar(0,70,639,95);
            sprintf(message,"Use the mouse pointer to define the top left corner of box %d",box);
            outtextxy(0,75,message);
            get_mouse_pos(&x1,&y1);
            image_boxes[box-1].ul.x =x1;
            image_boxes[box-1].ul.y =y1;
            cl = show_corner(x1,y1, EGA_WHITE);
            bar(0,70,639,95);
            outtextxy(0,83,"Now define the bottom right corner");
            get_mouse_pos(&x2,&y2);
            image_boxes[box-1].br.x =x2;
            image_boxes[box-1].br.y =y2;
            remove_corner(x1,y1,cl);
            bar(0,70,639,95);
        }
        boxptr = show_box(x1,y1,x2,y2, EGA_WHITE);
        remove_box(x1,y1,x2,y2,boxptr,1);
        free(boxptr);
    }
} void show_a_box(void)
{   int box;
    char message[81];
    unsigned int *boxptr;
    box = choose_box_num("Click on the number of the box you wish to view:",1);
    if (image_boxes[box-1].ul.x == -1) {
        bar(0,70,639,95);
        sound(400);
        sprintf(message,"Box %d is not defined\n",box);
        outtextxy(0,75,message);
        delay(1000);
        nosound();
        bar(0,70,639,95);
        return;
    }
    else {
        boxptr = show_box(image_boxes[box-1].ul.x,image_boxes[box-1].ul.y,
                    image_boxes[box-1].br.x,image_boxes[box-1].br.y,
                    EGA_WHITE);
        remove_box(image_boxes[box-1].ul.x,image_boxes[box-1].ul.y,
                image_boxes[box-1].br.x,image_boxes[box-1].br.y,
                boxptr,1);
        free(boxptr);
    }
}

/* AUTHOR: Nirav R. Desai
 * DATE:   7/30/90
 * This is the main routine which allows manipulation of boxes
 * which define the areas of interest on the image screen
 */
void define_image_boxes(void)
{   int choice, end;
    init_image_boxes();
    show_boxdef_choices();
    for (end=0;!end;) {
        switch(choice = get_boxdef_choice(boxdef_boxes)) {
        case 1: clear_box();
                break;
```

```
        case 2: save_box_file();
                break;
        case 3: edit_box_file();
                break;
        case 4: define_a_box();
                break;
        case 5: show_a_box();
                break;
        case 6: end = 1;
                break;
        }
        sound(choice*50);
        delay(200);
        nosound();
    }
    closegraph();
    return;
}
\032
``` saccade.h

```c
#define HALFSIZE 2
#define FULLSIZE 1
#define REDUCED 0          /* Marks a Fullsize image */
#define WAIT 1             /* Marks a Reduced image */
#define NOWAIT 0           /* Loadimage will wait for a key */
#define BATCH 0            /* Loadimage won't wait...used when performing test */
#define RESULTS 1          /* File type flag, used to decide where to look for file */
#define PICTURE 2          /*  "      "   --- */
#define S_TEXT 3           /*  "      "   --- */
#define BOX 4              /*  "      "   --- */
                           /*  "      "   --- */

/* When the file format for the four different files that
         * saccade deals with are changed, the file version marker
         * should be updated */ define RESMARK "RS3"
define PICMARK "IMG"      /* Most current Results file version */
#define TXTMARK "TXT"      /* Most current Picture file version */
#define BTCMARK "BT1"      /* Most current Text file version */
#define BOXMARK "BX1"      /*ND mod*/  /* Most current Batch file version */
#define MENUFG WHITE       /* Most current Box file version */
#define MENUBG BLUE        /* Standard menu colors used */
#define MENUSC YELLOW      /* FG = Foreground, BG = Background */
#define MENUBR RED         /* SC = Select Char Color */
                           /* BR = Bar Color */ define x_image_start 10   /* smallest usable x frame coord */
define x_image_stop 490   /* largest usable x frame coord */
#define y_image_start 24   /* smallest usable y frame coord */
define y_image_stop 470   /* largest usable y frame coord */ define NUMPICS 2 include <dir.h>
include <time.h>

/* Typedef for marker at beginning of file to specify type */
typedef char markertype[4];

/* Structure for information header for picture files */
struct pictrect {
    char marker[4];
    int size;
    char name[128];
};

typedef struct pictrect picture;

typedef char imagename[MAXPATH];

struct imagestruct {
    imagename name;
    char active;
};

typedef struct imagestruct imagetype;

/* Structure holding a list of images to be displayed on
         * the same screen */
/*ND mod*/
struct imageliststruct {
    int size;
    imagetype image[NUMPICS];
    char results[MAXPATH];
    char boxdefs[MAXPATH];      /* The results file for the screen */
                                /* The box file for the screen */
};

typedef struct imageliststruct imagelisttype;

/* Data structure for information gathered during a test */
struct datastruct {
    int x;
```

```
    int y;
    int hd;
    int vd;
    int mark;
    float time;
};

typedef struct datastruct datatype;

struct subjectstruct {
    char name[41];          /* 40, 10, and 80 characters plus */
    char number[11];        /* the NULL terminator */
    char info[81];
};
typedef struct subjectstruct subjecttype;

void close_outfile(void);
void status(char *st);
void boundlines(void);
void remove_status(void);
void initcolors(void);
void icon(int xloc, int yloc);
unsigned validfile(char *st, char *vl);
char *makefilename(char *mfn, int typefile);
char *getimagedescr(char *iname);
unsigned char create_textoutfile(FILE *h, char *st, char *attr);
unsigned getnewfilename(char *f, char *msg, int typefile);
unsigned getboxfilename(char *f, char *msg);
unsigned getresultsfile(char *resultsname, char *filespec);
unsigned getimagelist(imagelisttype *i, int test);
void drawimage(int size, int wait, int box_x, int box_y);
void loadimage(imagelisttype *i, int wait);
void saveimage(void);
void show_main(char *m);
\032
``` imagebox.h

```
define MAX_BOXES 15 typedef struct corner {
                    int x;
                    int y;
                };
typedef struct corner cornertype;

typedef struct boxdef {
                    cornertype ul;
                    cornertype br;
                };

typedef struct boxdef boxdeftype;

void set_boxdef_boxes(void);
void get_mouse_pos(unsigned int *xpos, unsigned int *ypos);
int choose_box_num(char *msg, int must_choose);
unsigned int *show_box(int x1, int y1, int x2, int y2, int color);
void define_image_boxes(void);
void remove_box(int x1, int y1, int x2, int y2, unsigned int *rect, int wait);\032
``` sacboxes.h

```
#define BUFSIZE 275
struct activeboxstruct {
    struct activeboxstruct *next;
    int num;
    int ulx, uly, lrx, lry;
    int enable;
};
typedef struct activeboxstruct activeboxtype;

void set_gaze_speed(int sp);
void set_box_mark(int on);
void set_nobox_mark(int on);
void *place_lp(int x, int y, int color);
void remove_lp(int x, int y, void *s);
void add_activebox(activeboxtype *abl, int num, int ulx, int uly, int lrx, int lry);
activeboxtype *start_activebox(int num, int ulx, int uly, int lrx, int lry);
int lookupbox(activeboxtype *abl, int x, int y);
int getbox(activeboxtype *abl, int *box, int han, unsigned maxlp, int useboxes, float start_time);
void dispose_activeboxlist(activeboxtype *abl);
\032
``` gaze_umd.h

```c
struct filterstruct {
    struct filterstruct near *next;
    double xlp;
    double ylp;
};

typedef struct filterstruct filtertype;

void initgaze(int xr, int yr, int numave, int numcal);
void set_gaze_res(int xr, int yr);
void set_recalibrate(void);
void reset_calpts(int numcal);
void clear_recalibrate(void);
unsigned get_deltas(double *dx, double *dy, int *hpupdia, int *vpupdia, double *tdx, double *tdy, double *numr);
unsigned getgazeposition(int *x, int *y, int *hpupdia, int *vpupdia);
void fill_Gr_arrays(int num_start, int num_stop, int xmove, int ymove, int A, int B, int C, int cal);
void get_animation_configuration(void);
void assign_anim_buffers(void *anim_buffer[13], void *smiley);
void init_graph_needs (Matrix *ix, Matrix *iy, void *anim_buffer[13], void *smiley);
void animate(void *anim_buffer[13], void *smiley, int *counter);
void clear_graphics(void);
static unsigned calibrate(Matrix *mx, Matrix *my);
\032
``` sacimprc.h

```c
typedef double rhistarray[256];

void smooth_image(void);
void reduce_image(void);
void equalize_image(void);
void reverse_image(void);
void binary_image(int threshold);
\032
``` sacresul.h

```c
void summarize_results(char *resfile);
void listresults(char *resfile);
void graph_results(char *resfile);
void supimp_results(char *resfile, int waitforkey);
void analysis_options(void);\032
``` boxdef.c

```c
/*****************************************************************
 * AUTHOR: Kevin S. Spetz
 * LAST REVISION: 5/5/89   LAST MODIFICATION 3/29/90
 *
 * Program which allows a user to generate text and picture stimuli, then
 * monitor a subject's pupil diameter and look-point as the stimuli are
 * presented on the screen.
 *****************************************************************
 */ include <stdio.h>
include <conio.h>
#include <string.h>
#include <io.h>
#include <dos.h>
#include <ctype.h>
#include <stdlib.h>
#include <alloc.h>
#include <stdarg.h>
#include <fcntl.h>
#include <stat.h>
#include <math.h>
include <graphics.h>
#include "c:\cgaze\fgroutns.h"
#include "c:\cgaze\gaze.h"
#include "c:\maryland\sacboxes.h"    /* Was saccade\sacboxes.h*/
#include "c:\ericalib\tools.h"
#include "c:\ericalib\grtools.h"
#include "c:\ericalib\menu.h"
#include "c:\ericalib\moustool.h"
#include "c:\ericalib\timex.h"
#include "c:\maryland\imagebox.h"
#include "c:\maryland\sacimprc.h"
#include "c:\maryland\sacresul.h"
#include "c:\maryland\saccade.h"

extern activeboxtype *boxdef_boxes;

char outname[128];
```

```c
struct palettetype palette;
static subjecttype subjectinfo;

static int filterpts = 1;          /* Number of points used in the running
                                    * look-point filter.  Used when initgaze
                                    * is called
                                    */ static int calibpts = 8;           /* Number of icon positions used during
                                    * calibration.  Sent to initgaze
                                    */ static int box_lp_on = 0;          /* Determines whether or not a look-point
                                    * is shown within active boxes.
                                    */ static int nobox_lp_on = 0;        /* Determines whether or not a look-point
                                    * is shown outside of active boxes.  If
                                    * boxes are not active, this determines
                                    * whether a look-point is shown at all.
                                    */ static int total_lp = 0;           /* Total number of look-points allowed
                                    * on an individual screen.
                                    */ static int num_box_lp = 0;         /* Number of look-points required to
                                    * select a box.
                                    */ static int useboxes = 0;           /* Flag to determine whether or not the
                                    * screen boxes are active or not.
                                    */

/* Standard menu color definitions, used
                                    * by menu software in menu.c
                                    */
static menucolortype blue_menu = {WHITE,BLUE,YELLOW,RED,LIGHTGRAY};
static menucolortype gray_menu = {BLACK,LIGHTGRAY,WHITE,RED,DARKGRAY};

/* Menu definitions used in the saccade
                                    * menu structure.
                                    */
static menuitemtype main_menu[] = {
   {1,0,"Digitize and Store an Image"},
   {1,20,"Generate and Save a Text Screen"},
   {1,0,"Perform saccadic motion test"},
   {1,0,"Analyze Results"},
   {1,0,"Register a Subject"},
   {1,0,"Quit"},
   {1,0,"EOM"}
   };

static int last_mm_option = 0;

static menuitemtype picture_menu[] = {
   {1,7,"Grab a Frame"},
   {1,0,"Continuous"},
   {1,11,"Make Image Binary"},
   {1,0,"Draw the image on a graphics screen"},
   {1,0,"Equalize the image"},
   {1,25,"Reverse the intensities (Negative)"},
   {1,14,"Perform image Reduction"},
   {1,0,"Average image intensities, smoothing"},
   {1,2,"Box on image"},
   {1,0,"Load image from disk"},
   {1,0,"Save image on disk"},
   {1,0,"Quit"},
   {1,0,"EOM"},
   };

static int last_pm_option = 0;

static menuitemtype picsize_menu[] = {
   {1,0, "Full Sized"},
   {1,0, "Reduced"},
   {1,0, "EOM"}
   };

static menuitemtype text_io_menu[] = {
   {1,0,"Load text screen"},
   {1,0,"Save current screen"},
   {1,0,"Quit"},
   {1,0,"EOM"}
   };

static menuitemtype test_menu[] = {
   {1,0,"Perform test with a set of pictures or text"},
```

```c
    {1,0,"Create a Picture test batch file"},
    {1,0,"Edit Batch file"},
    {1,23,"Execute a picture test Batch file"},
    {1,1,"Configure test environment"},
    {1,7,"Define Important areas of image"},
    {1,0,"Quit"},
    {1,0,"EOM"}
    };

static int last_tm_option = 0;

static menuitemtype config_menu[] = {
    {1,10,"Number of Calibration Points"},
    {1,11,"Look-Point Filter Window Size"},
    {1,7,"Active Box lookpoint feedback"},
    {1,0,"No Box feedback"},
    {1,0,"Total lookpoints allowed"},
    {1,0,"Look-points required to select a box"},
    {1,0,"Active boxes status"},
    {1,0,"Quit"},
    {1,0,"EOM"},
    };

static menuitemtype box_menu[] = {
    {1,0,"1 (\334 _ _)"},
    {1,0,"2 (_ \334 _)"},
    {1,0,"3 (_ _ \334)"},
    {1,0,"Quit"},
    {1,0,"EOM"}
    };
static int last_cm_option = 0;

static menuitemtype calibpts_menu[] = {
    {1,0,"4"},
    {1,0,"5"},
    {1,0,"8"},
    {1,0,"EOM"},
    };

static menuitemtype on_off_menu[] = {
    {1,0,"On"},
    {1,1,"off"},
    {1,0,"EOM"}
    };

/* Mod for two images instead of four: 29 MAR 90 Greg Schubert
   (and the program is written for the top LEFT corner)       */

/* Screen locations for placing images on a graphics screen two at a time.
 * Points represent the (x,y) locations of the upper right hand corner of
 * each image. WILL WANT TO CHANGE THIS WHEN NUMBER OF BOXES WILL BE
 * VARIABLE. PROBABLY READ IT IN OR SOMEHOW DEFINE IT DYNAMICALLY.
 */ int image_loc[4] = {
    0,101,376,101
    };

int text_box_loc[3][4] = {
    {9,17,24,23},
    {33,17,48,23},
    {57,17,72,23},
    };

/* ND mod to add time stamping */
float start_time;

static void showmem(void)
    { xycprintf(60,2,WHITE,"Core = %u",coreleft());
    }

/* Routine that displays a message to the user
 */
void status(char *st)
    { int xp;
      struct text_info ti;
      gettextinfo(&ti);
      xp = 79 - strlen(st);
      if (xp > 15)
         xycprintf(xp,24,LIGHTCYAN,"%s",st);
      textattr(ti.attribute);
    } void remove_status(void)
    { cputchar(11,24,BLUE,BLUE,66,' ');
    }
void boundlines(void)
    {
    xycprintf(1,3, CYAN,"--------------------------------------------------------------------------------");
    xycprintf(1,23,CYAN,"--------------------------------------------------------------------------------");
    }
```

```c
/*
 * 15 color Blues palette Used as a "grey" scale
 * for image presentation.
 */
void initcolors(void)
  { getpalette(&palette);
    palette.colors[0] = 0;
    palette.colors[1] = 8;
    palette.colors[2] = 1;
    palette.colors[3] = 33;
    palette.colors[4] = 17;
    palette.colors[5] = 49;
    palette.colors[6] = 9;
    palette.colors[7] = 41;
    palette.colors[8] = 25;
    palette.colors[9] = 57;
    palette.colors[10] = 11;
    palette.colors[11] = 43;
    palette.colors[12] = 27;
    palette.colors[13] = 59;
    palette.colors[14] = 31;
    palette.colors[15] = 63;
    palette.size = 15;
    setallpalette(&palette);
  }

/* Routine to place a small icon at the screen location xloc, yloc.
 */
void icon(int xloc, int yloc)
   { setcolor(0);
     circle(xloc,yloc,5);
     circle(xloc,yloc,4);
     circle(xloc,yloc,3);
     circle(xloc,yloc,2);
     setcolor(15);
     circle(xloc,yloc,1);
   }

/* AUTHOR: Kevin S. Spetz
 * DATE:
 * Routine to draw an image held in the frame buffer on the graphics screen.
 * The parameter size indicate a reduced or fullsize image, and the parameter
 * wait tells drawimage whether or not to wait for a key to be pressed before
 * returning
 */
/* Modified 27 MAR 90  Greg Schubert  */ void drawimage(int size, int wait, int box_x, int box_y)
  {
/*ND mod int xoffset, maxx;*/
      int yoffset,xstart,ystart,xstop,ystop,x,y, maxy;
      unsigned char near *buf;
      int counter=0;
      int max_counter=1000;
      int y_counter=0;

if ((buf = (unsigned char near *) malloc(512 * sizeof(unsigned char))) == NULL) {
         clrscr();
         fprintf(stderr,"Not enough memory for image buffer -- Aborting.");
         exit(0);
         }
      newsetupgraphics(EGA,EGAHI);
      initcolors();
/*ND mod      maxx = getmaxx();*/
      maxy = getmaxy();
      if (size == FULLSIZE) {
/*ND mod       xoffset = (maxx - 512)/2;*/
        yoffset = (maxy - 512)/2;
        xstart = ystart = 0;
        xstop = 512;
        ystop = y_image_stop;
        y_counter=ystart;
        max_counter=4;
        }
      else if (size==HALFSIZE)
        {
/*ND mod       xoffset=(maxx-512)/2;*/
        yoffset=(maxy-512)/2;
        xstart=box_x;
        ystart=box_y;
        xstop=xstart+240;
        ystop=ystart+400;
        max_counter=4;
        y_counter=ystart;
        }
      else { /*ND mod xoffset = 235;*/
             yoffset = 95;
             xstart = ystart = 0;
/* mod */    xstop = 256;
/* mod */    ystop = 239;
             y_counter=ystart;
             }
      if (yoffset < 0)
         yoffset = 0;
```

```c
    for (y = ystart; y < ystop; y++)
        {
        counter++;
        if (counter:=max_counter)
            {
            getrowavw(y,0,512,buf);
            for(x = xstart; x < xstop; x++)
                {
                putpixel(x-xstart, y_counter-ystart,
                        (int) ((*(buf + x) * (palette.size + 1))/256.0));
                }
            y_counter++;
            }
        else
            {
            counter=0;
            }
        }
    if (wait) {
        getch();
        closegraph();
        } free(buf);
    }

/* AUTHOR: Kevin S. Spetz
 * DATE:
 * Routine to load an image from disk to the EGA screen
 */
/* modified 27 MAR 90 Greg Schubert */
void loadimage(imagelisttype *i,int wait)
    { void * buffer;
    char buffer2[1984];
    unsigned size;
    int han;
    picture descr;
    int count;
    markertype marker;
    int k;
    /*, j;
    signed offset, offset2;
    int change;
    long int tmpint;
    unsigned tmpnum, numbytes;*/ if (validfile(i->image[0].name,TXTMARK)) {
        setcursor(NO_CURSOR);
        textbackground(BLACK);
        clrscr();
        if ((han = open(i->image[0].name,O_RDONLY)) != -1) {
            _read(han,&marker,sizeof(markertype));
            if ((buffer = malloc(80*21*2)) == NULL) {
                fprintf(stderr,"Memory Allocation Error -- load image\n");
                exit(0);
            }
            _read(han,buffer,80*21*2);
            puttext(1,3,80,23,buffer);
            free(buffer);
            close(han);
            if (wait) {
                getch();
                clrscr();
                return;
            }
            else return;
        }
        else { fprintf(stderr,"Error! File won't open -- loadimage");
            exit(1);
        }
    }
    newsetupgraphics(EGA,EGAHI);
    setvisualpage(1);
    initcolors();
    for (count = 0; count < i->size; count++) {
        if ((han = open(i->image[count].name,O_RDONLY)) != -1) {
            _read(han,&descr,sizeof(picture));
            if (descr.size == FULLSIZE) {
                size = imagesize(0,0,639,117);
                if ((buffer = malloc(size)) == NULL) {
                    closegraph();
                    fprintf(stderr,"Error! Memory Allocation -- Load image(large) -- coreleft = %u needed %u",coreleft(),size);
                    exit(1);
                }
                _read(han,buffer,size);
                putimage(0,0,buffer,COPY_PUT);
                _read(han, buffer,size);
                putimage(0,118,buffer,COPY_PUT);
                free(buffer);
                size = imagesize(0,236,639,349);
                if ((buffer = malloc(size)) == NULL) {
                    closegraph();
                    fprintf(stderr,"Error! Memory Allocation -- load image(large) -- Coreleft = %u needed
```

```
             %u",coreleft(),size);
                  exit(1);
                  }
                  _read(han, buffer,size);
                  putimage(0,236,buffer,COPY_PUT);
                  close(han);
                  free(buffer);
                  }
/* mod        else {
                  size = imagesize( 0, 0,256,239);
                  if ((buffer = malloc(size)) == NULL) {
                      closegraph();
                      fprintf(stderr,"Error! Memory Allocation -- load image(small) -- coreleft = %u",corel
eft());
                      exit(1);
                      }
                  _read(han,buffer,size);
                  putimage(image_loc[count * 2],image_loc[count * 2 + 1],buffer,COPY_PUT);
                  close(han);
                  free(buffer);
*/
/* mod */    else {
                  /*printf("(left) upper left x: ");
                  fscanf(stdin,"%d",&ulx);
                  printf("(top) upper left y: ");
                  fscanf(stdin,"%d",&uly);
                  printf("(bottom) bottom right x: ");
                  fscanf(stdin,"%d",&brx);
                  printf("(right) bottom right y: ");
                  fscanf(stdin,"%d",&bry);
                  size = imagesize( ulx,uly,brx,bry);

printf("Enter offset from beg. of buffer2: ");
       fscanf(stdin,"%d",&offset);

printf("    Enter int to add to buf2: ");
       fscanf(stdin,"%d",&change);

printf("    Enter #bytes to read: ");
       fscanf(stdin,"%u",&numbytes);
*/
                  _read(han,buffer2,1984);
             /*   tmpchr[1] = '\0';
                  printf("buffer2 loc = %p",buffer2);
                  for (j=0;j<12;j++) {
                      memcpy(tmpchr, (char *)(buffer2+j), 1);
                      tmpint = (int) tmpchr[0];
                      if (min(tmpint,0)<0) tmpint = 256+tmpint;
                      printf("\ntmpchr = %s, buf2, byte %d contains %ld - also:%d",tmpchr, j,tmpint,peekb(_
DS,(buffer2+j)));
                      }
                  getch();*/
                  memset(buffer2+2,14,1);
                  putimage(image_loc[count * 2],image_loc[count * 2 + 1],buffer2,COPY_PUT);

for (k = 15; k<240;k+=15) {
                    _read(han,buffer2+4,1980);
                 /* if (k<76) {
                       printf("k = %d",k);
                       for (j=0;j<18;j++) {
                           memcpy(tmpchr, (char *)(buffer2+j), 1);
                           tmpint = (int) tmpchr[0];
                           if (min(tmpint,0)<0) tmpint = 256+tmpint;
                           printf("\ntmpchr = %s, buf2, byte %d contains %ld - also:%d",tmpchr, j,tmpint,p
eekb(_DS,(buffer2+j)));
                           }
                       }*/
                    putimage(image_loc[count * 2],image_loc[count * 2 + 1]+k,buffer2,COPY_PUT);
                    }
                  close(han);
                  }
              }
         else { outtextxy(image_loc[count*2] + 5,image_loc[count * 2 + 1]+ 5,"Error!");
                outtextxy(image_loc[count*2] + 5,image_loc[count * 2 + 1] + 15,"No Picture file found");
                }
         }
     setvisualpage(0);
     if (wait) {
        getch();
        closegraph();
     }
  }

/* AUTHOR: Kevin S. Spetz
 * DATE:
 * Routine to save an image from the screen to disk.
 */
/* modified 27 MAR 90 Greg Schubert */
void saveimage(void)
   { void * buffer;
     windowtype *tbuf;
     int han;
     unsigned size;
     char ch;
     picture descr;
```

```c
    tbuf = open_window(10,5,73,19,WHITE,CYAN,1,"");
    textcolor(WHITE);
    xycprintf(2,3,LIGHTCYAN,"Please enter filename to save the image under: ");
    getstring(outname);
    strupr(outname);
    makefilename(outname,PICTURE);
    xycprintf(4,6,LIGHTCYAN,"Enter a description of the picture :");
    xycprintf(4,7,YELLOW,"-> ");
    getstring(descr.name);
    if ((han = open(outname,O_WRONLY | O_CREAT,S_IREAD | S_IWRITE)) != -1) {
       setcursor(SHORT_CURSOR);
       xycprintf(4,10,LIGHTCYAN,"Save the Entire image or the Reduced one (E/R)? ");
       while(((ch = toupper(getch())) != 'E') && (ch != 'R') );
       setcursor(NO_CURSOR);
       close_window(tbuf);
       if (ch == 'E') {
           strcpy(descr.marker,PICMARK);
           descr.size = FULLSIZE;
           _write(han,&descr,sizeof(picture));
           drawimage(FULLSIZE,NOWAIT,0,0);
           size = imagesize(0,0,639,117);
           if ((buffer = malloc(size)) == NULL) {
              closegraph();
              fprintf(stderr,"Error! Memory Allocation -- Save image\n");
              exit(1);
           }
           getimage(0,0,639,117,buffer);
           _write(han,buffer,size);
           getimage(0,118,639,235,buffer);
           _write(han,buffer,size);
                free(buffer);
           size = imagesize(0,236,639,349);
           if ((buffer = malloc(size)) == NULL) {
              closegraph();
              fprintf(stderr,"Error! Memory Allocation -- Save image\n");
              exit(1);
           }
           getimage(0,236,639,349,buffer);
           _write(han,buffer,size);
           free(buffer);
           close(han);
           closegraph();
           }
       else {
           descr.size = REDUCED;
           strcpy(descr.marker,PICMARK);
           _write(han,&descr,sizeof(picture));
           drawimage(REDUCED,NOWAIT,0,0);
/* mod */  size = imagesize(0,0,256,239);
           if ((buffer = malloc(size)) == NULL) {
              closegraph();
              fprintf(stderr,"Error! Memory Allocation -- Save image\n");
              exit(1);
           }
/* mod */  getimage(0,0,256,239,buffer);
           _write(han,buffer,size);
           free(buffer);
           close(han);
           closegraph();
           }
       }
    else { close_window(tbuf);
         xycprintf(1,25,RED,"Can't open file %s -- terminating program with error %d\n",outname,errno
);
         exit(1);
         }
    } char *text_screen_io(char *filename)
 { windowtype *tbuf1;
   int lo = 0;
   int tag, han;
   void * buffer;
   unsigned done1;
   char fname[MAXPATH];
   char temp[16];
   markertype marker;

tbuf1 = open_window(5,5,30,11,LIGHTCYAN,BLUE,0,"File I/O");
   switch(menuselect(4,2,text_io_menu,&lo)) {
      case 'L' :
         done1 = 0;
         while (!done1) {
            selectfile("c:\\saccade\\text\\*.txt",fname,&tag,55,5,1,14);
            if (!validfile(makefilename(fname,S_TEXT),TXTMARK)) {
               extract_fn(temp,fname);
               strcat(temp," is not a valid");
               error(temp,"text file!");
               }
            else done1 = 1;
            }
         close_window(tbuf1);
         if ((han = open(fname,O_RDONLY)) != -1) {
            _read(han,&marker,sizeof(markertype));
```

```c
            if ((buffer = (void *) malloc(80*21*2)) == NULL) {
                fprintf(stderr,"Error! Memory Allocation -- save image.\n");
                exit(-1);
                }
            _read(han,buffer,80*21*2);
            puttext(1,3,80,23,buffer);
            free(buffer);
            close(han);
            }
        else { fprintf(stderr,"Error! Couldn't open file %s.\n",fname);
               exit(-1);
               }
        break;
    case 'S' :
        close_window(tbuf1);
        if ((buffer = malloc(80*21*2)) != NULL) {
            gettext(1,3,80,23,buffer);
            tbuf1 = open_window(12,9,68,15,LIGHTCYAN,CYAN,1,"");
            textcolor(WHITE);
            gotoxy(2,3);
            if (getnewfilename(fname,"Enter the file to save the Text in: ",S_TEXT)) {
                han = open(fname,O_WRONLY | O_CREAT, S_IREAD | S_IWRITE);
                strcpy(marker,TXTMARK);
                _write(han,&marker,sizeof(markertype));
                _write(han,buffer,80*21*2);
                close(han);
                free(buffer);
                }
            else free(buffer);
            close_window(tbuf1);
            message("Successfully save the text screen");
            }
        else { xycprintf(1,25,RED,"Not Enough Memory to get screen");
               exit(1);
               }
        break;
    case 'Q' :
        close_window(tbuf1);
        strcpy(fname,"");
        break;
    }
    extract_fn(filename,fname);
    return(filename);
    }

/* AUTHOR: Kevin S. Spetz
 * DATE.
 * Routine which allows a user to enter text onto the screen, then allows the
 * screen to be saved to disk.
 */
void savetext (void)
    { int x,y,color = CYAN;
unsigned done;
char temp[16];
char ch;

textbackground(BLACK);
setcursor(SHORT_CURSOR);
clrscr();
textcolor(CYAN);
cputchar(1,2,CYAN,BLACK,80,'~');
cputchar(1,24,CYAN,BLACK,80,'~');
xycprintf(1,1,LIGHTRED,"Text Screen");
xycprintf(30,1,RED,"File:");
xycprintf(1,25,GREEN,"F1: File I/O   F2: Clear/Restart");
xycprintf(36,25,CYAN,"F3: Change Color");
xycprintf(55,25,GREEN,"F4: Add Boxes");
xycprintf(71,25,WHITE,"ESC: Quit");
x = 1; y = 3;
done = 0;
while (!done) {
    xycprintf(67,1,WHITE,"Row:%2d  Col:%2d",y - 2,x);
    gotoxy(x,y);
    switch (ch = getch()) {
        case 0    : switch (ch = getch()) {
                        case F1    : xycprintf(36,1,YELLOW,"%12s",text_screen_io(temp));
                                     break;
                        case F2    : window(1,3,80,23);
                                     clrscr();
                                     window(1,1,80,25);
                                     x = 1; y = 3;
                                     break;
                        case F3    : if (++color > 15)
                                         color = 1;
                                     textcolor(color);
                                     xycprintf(36,25,color,"F3: Change Color");
                                     break;
                        case F4    : set_box_line(SINGLE);
                                     switch(choose("Draw which box?","1, 2, or 3",box_menu)) {
                                         case '1' :
                                             draw_a_box(text_box_loc[0][0],text_box_loc[0][1],
                                                        text_box_loc[0][2],text_box_loc[0][3],
                                                        color,BLACK,0);
                                             break;
                                         case '2' :
                                             draw_a_box(text_box_loc[1][0],text_box_loc[1][1],
```

```
                                            text_box_loc[1][2],text_box_loc[1][3],
                                            color,BLACK,0);
                                break;
                             case '3' :
                                draw_a_box(text_box_loc[2][0],text_box_loc[2][1],
                                            text_box_loc[2][2],text_box_loc[2][3],
                                            color,BLACK,0);
                                break;
                            }
                            set_box_line(DOUBLE);
                            break;
              case UpArrow : y--;
                             bind(&y,3,23);
                             break;
              case DnArrow : y++;
                             bind(&y,3,23);
                             break;
              case LfArrow : x--;
                             bind(&x,1,80);
                             break;
              case RtArrow : x++;
                             bind(&x,1,80);
                             break;
                           }
                           break;
          case BCKSP: x--;
                      bind(&x,1,80);
                      gotoxy(x,y);
                      putch(' ');
                      break;
          case RET  : x = 1;
                      y++;
                      bind (&y,3,23);
                      break;
          case ESC  : done = 1;
                      break;
          default   : putch(ch);
                      x++;
                      bind(&x,1,80);
                      break;
         }
       }
       setcursor(NO_CURSOR);
}

/* AUTHOR: Kevin S. Spetz
 * DATE: 7/17/89
 * Routine which looks in the imagelist and builds a box list for use by the
 * sacboxes routines. Uses the Active flag to decide how to build the list.
 * for image files active is 1 or 0; depending on the value the image position
 * is added to or not added to the box list. For Text screens the value is
 * 0 - 7, where the first bit is the first allows box on the text screen,
 * the second bit is the second, and the third the third. In the future this
 * method should be improved.
 */
activeboxtype *build_abl(imagelisttype *i)
{    activeboxtype *b = NULL;
     int count;
     if (validfile(i->image[0].name,TXTMARK)) {
        if (i->image[0].active & 0x01)
           b = start_activebox(1,text_box_loc[0][0],text_box_loc[0][1],
                            text_box_loc[0][2],text_box_loc[0][3]);
        if (i->image[0].active & 0x02) {
           if (b == NULL)
              b = start_activebox(2,text_box_loc[1][0], text_box_loc[1][1],
                            text_box_loc[1][2], text_box_loc[1][3]);
           else add_activebox(b,2,text_box_loc[1][0], text_box_loc[1][1],
                            text_box_loc[1][2], text_box_loc[1][3]);
        }
        if (i->image[0].active & 0x04) {
           if (b == NULL)
              b = start_activebox(3,text_box_loc[2][0], text_box_loc[2][1],
                            text_box_loc[2][2], text_box_loc[2][3]);
           else add_activebox(b,2,text_box_loc[2][0], text_box_loc[2][1],
                            text_box_loc[2][2], text_box_loc[2][3]);
        }
     }
     for (count = 0; count < i->size + 1; count++) {
        if (i->image[count].active) {
           if (b == NULL)
/*ND mod */      b = start_activebox(count+1,image_loc[count*2],image_loc[count*2+1],image_loc[count*2]+256,image_loc[count*2+1]+239);
/*ND mod */      else add_activebox(b,count+1,image_loc[count*2],image_loc[count*2+1],image_loc[count*2]+256,image_loc[count*2+1]+239);
        }
     }
     return(b);
}

/* AUTHOR: Kevin S. Spetz
 * DATE:
 * Routine which displays the images (picture or text) held in *i and then
 * monitors the subject's pupil diameter and look-point as the stimuli
 * is displayed. The test will cease after a number of look-points, or
 * when the space bar is pressed. If any other key is pressed that key
```

```c
 * will be stored in the data file as a label.
 */
void performtest(imagelisttype *i)
   { int han;
     char marker[4];
     int box;
     activeboxtype *abl = NULL;
     unsigned tp;

if (total_lp == 0)
tp = 32000;                    /* trying to grab 0 lookpoints means
                                  just wait for a key, ie make tp big*/
   else tp = total_lp;
   strcpy(marker,RESMARK);
   if ((han = open(i->results,O_WRONLY | O_TRUNC | O_CREAT,S_IREAD | S_IWRITE)) != -1) {
      _write(han,&marker,sizeof(marker));
      _write(han,&subjectinfo,sizeof(subjecttype));
      _write(han,i,sizeof(imagelisttype));
      abl = build_abl(i);
      getbox(abl,&box,han,tp,useboxes, start_time);
      dispose_activeboxlist(abl);
      close(han);
      }
  }

/* Routine to show the main screen.
 */
void show_main(char *m)
   { setcursor(NO_CURSOR);
     draw_a_box(1,1,80,25,CYAN,BLUE,0);
     boundlines();
     fastwrite(3,24,LIGHTGREEN,BLUE,"Messages:");
     fastwrite(3,2,LIGHTRED,BLUE,m);
     fastwrite(10,7,YELLOW,BLUE,"Please Make a Selection");
     showmen();
   }

/* AUTHOR: Kevin S. Spetz
 * DATE:
 * Routine which asks the user to select a batch file and then executes it.
 */
void batch_test(void)
   { int han, done,x,y,dummyint;
     windowtype *buf;
     char outname[128];
     imagelisttype imagelist;
     markertype marker;
     int tag;

/*****************May have to do something here for grapics error*/
     set_recalibrate();
     continuous();
     textcolor(WHITE);
     done = 0;
     while (!done) {
        if (selectfile("c:\\saccade\\batch\\*.btc",outname,&tag,8,7,4,14)) {
           if (validfile(makefilename(outname,BATCH),BTCMARK)) {
              textbackground(BLACK);
              clrscr();
              buf = open_window(25,10,55,14,CYAN,BLACK,1,"");
              xycprintf(3,2,WHITE,"Press any Key to begin...");
              getch();
              close_window(buf);
              getgazeposition(&x,&y,&dummyint,&dummyint);
              han = open(outname,O_RDONLY);
              _read(han,&marker,sizeof(markertype));
/*ND mod*/    start_time = timex();
              while (_read(han,&imagelist,sizeof(imagelisttype)) == sizeof(imagelisttype) ) {
                 loadimage(&imagelist,0);
                 performtest(&imagelist);
                 if (screen_mode() != TEXT)
                    closegraph();
                 }
              done = 1;
              close(han);
              }
           else { buf = open_window(10,12,70,14,WHITE,RED,1,"");
                  xycprintf(2,1,WHITE,"%s is not a valid batch file",outname);
                  delay(2000);
                  close_window(buf);
                  }
              }
        else done = 1;
        }
   }

/* AUTHOR: Kevin S. Spetz
 * DATE:
 * Routine which allows the user to select a batch file and then edit
 * the results file list it holds.  Allows the batch file to be updated
 * to have new, unique names to store data in during a test.
 */
```

```
void edit_batchfile(void)
  { int han,han2, done,count;
    windowtype *buf,*buf2;
    char outname[64];
    char seed[64] = "";
    char tmpname[32];
    char tempfile[64];
    imagelisttype imagelist;
    int tag;
    markertype marker;

textcolor(WHITE);
    done = 0;
    buf = open_window(15,4,65,12,BLACK,LIGHTGRAY,1,"Batch file edit");
    xycprintf(5,3,BLACK,"Filename: _____");
    xycprintf(5,4,BLACK,"    Seed: ");
    xycprintf(5,5,BLACK,"   Range: ");
    while (!done) {
        if (selectfile("c:\\saccade\\batch\\*.btc",outname,&tag,55,3,1,19)) {
            if (validfile (makefilename(outname,BATCH),BTCMARK)) {
                xycprintf(15,3,WHITE,"        ");
                xycprintf(15,3,WHITE,"%s",outname);
                xycprintf(15,4,BLACK,"_____");
                buf2 = open_window(20,15,53,19,WHITE,CYAN,1,"");
                xycprintf(2,2,LIGHTCYAN,"Enter Seed: ");
                textcolor(WHITE);
                textbackground(CYAN);
                if (editstring(seed,"",5)) {
                    close_window(buf2);
                    xycprintf(15,4,WHITE,"%s   ",seed);
                    tmpnam(tempfile);
                    han = open(outname,O_RDONLY);
                    han2 = open(tempfile,O_WRONLY | O_CREAT,S_IREAD | S_IWRITE);
                    _read(han,&marker,sizeof(markertype));
                    _write(han2,&marker,sizeof(markertype));
                    count = 0;
                    xycprintf(15,5,WHITE,"%s000.res",seed);
                    xycprintf(28,5,BLACK,"to");
                    while(_read(han,&imagelist,sizeof(imagelisttype)) == sizeof(imagelisttype)) {
                        sprintf(tmpname,"%s%03d",seed,count);
                        xycprintf(31,5,WHITE,"%s.res",tmpname);
                        strcpy(imagelist.results,makefilename(tmpname,RESULTS));
                        _write(han2,&imagelist,sizeof(imagelisttype));
                        count++;
                    }
                    close(han);
                    close(han2);
                    remove(outname);
                    rename(tempfile,outname);
                    remove(tempfile);
                    xycprintf(13,7,BLACK + BLINK,"Press any key to continue");
                    getch();
                    done = 1;
                }
                else { close_window(buf2);
                       done = 1;
                     }
            }
            else { buf2 = open_window(10,12,70,14,WHITE,RED,1,"");
                   xycprintf(2,1,WHITE,"%s is not a valid batch file",outname);
                   delay(2000);
                   close_window(buf2);
                 }
        }
        else done = 1;
    }
    close_window(buf);
  }

/* AUTHOR: Kevin S. Spetz
 * DATE:
 * Routine which allows the user to select a stimuli then monitors the
 * subject as the stimuli is displayed.  The test length is limited to
 * one screen.
 */
void single_test(void)
  { windowtype *buf;
    int x,y,dummyint;
    imagelisttype imagelist;

/* *************** May have to do something about calibration here*/
    set_recalibrate();
    continuous();
    if (getimagelist(&imagelist,1)) {
        textbackground(BLACK);
        clrscr();
        buf = open_window(25,10,55,14,CYAN,BLACK,0,"");
        xycprintf(3,2,WHITE,"Press any Key to begin...");
        getch();
        close_window(buf);
        getgazeposition(&x,&y,&dummyint,&dummyint);
/*ND mod*/
        start_time = timex();
        loadimage(&imagelist,0);
        performtest(&imagelist);
```

```
        if (screen_mode() != TEXT)
            closegraph();
        }
    } void test_configure(void)
    { windowtype *buf, *buf2;
      int done = 0;
      char ch;
      menucolortype tmp;

getmenucolors(&tmp);
      setmenucolors(&gray_menu);
      buf = open_window(3,3,54,14,BLACK,LIGHTGRAY,1,"Configure:");
      while (!done) {
          xycprintf(45,2,WHITE,"(%4d)",calibpts);
          xycprintf(45,3,WHITE,"(%4d)",filterpts);
          if (box_lp_on) xycprintf(45,4,WHITE,"( On)");
          else xycprintf(45,4,WHITE,"( Off)");
          if (nobox_lp_on) xycprintf(45,5,WHITE,"( On)");
          else xycprintf(45,5,WHITE,"( Off)");
          xycprintf(45,6,WHITE,"(%4d)",total_lp);
          xycprintf(45,7,WHITE,"(%4d)",num_box_lp);
          if (useboxes) xycprintf(45,8,WHITE,"( On)");
          else xycprintf(45,8,WHITE,"( Off)");
          ch = menuselect(5,2,config_menu,&last_cm_option);
          switch(ch) {
              case 'C' : switch(choose("How Many Calibration Points","to use",calibpts_menu)) {
                              case '4' : calibpts = 4; break;
                              case '5' : calibpts = 5; break;
                              case '8' : calibpts = 8; break;
                              }
                         initgaze(80,25,filterpts,calibpts);
                         break;
              case 'F' : buf2 = open_window(15,14,75,18,LIGHTCYAN,CYAN,1,"Input");
                         do {
                              filterpts = getnum(3,2,WHITE,"How many points to use in running Filter? ");
                              if ((filterpts > 8) || (filterpts < 0)) {
                                  error("Acceptable Numbers of Points to Filter","Over Range from 1 to 8");
                                  clrscr();
                                  }
                              } while ((filterpts > 8) || (filterpts < 0));
                         close_window(buf2);
                         initgaze(80,25,filterpts,calibpts);
                         break;
              case 'B' : switch(choose("Should Look-point feedback in active","boxes be On or Off?",on_off
_menu)) {
                              case 'O' : box_lp_on = 1; break;
                              case 'F' : box_lp_on = 0; break;
                              }
                         set_box_mark(box_lp_on);
                         break;
              case 'N' : switch(choose("Should look-point feedback outside","of active boxes be On or Off?
",on_off_menu)) {
                              case 'O' : nobox_lp_on = 1; break;
                              case 'F' : nobox_lp_on = 0; break;
                              }
                         set_nobox_mark(nobox_lp_on);
                         break;
              case 'T' : buf2 = open_window(12,10,68,15,LIGHTCYAN,CYAN,1,"Input");
                         xycprintf(4,4,LIGHTCYAN,"Enter 0 to operate until a key is pressed.");
                         total_lp = getnum(2,2,WHITE,"How many look-points to use during tests? ");
                         close_window(buf2);
                         break;
              case 'L' : buf2 = open_window(12,10,68,15,LIGHTCYAN,CYAN,1,"Input");
                         xycprintf(4,4,LIGHTCYAN,"Turn Active boxes off to disable this option.");
                         num_box_lp = getnum(2,2,WHITE,"How many look-points activate an active box? ");
                         set_gaze_speed(num_box_lp);
                         close_window(buf2);
                         break;
              case 'A' : switch(choose("Should the active boxes be","on or off?",on_off_menu)) {
                              case 'O' : useboxes = 1; break;
                              case 'F' : useboxes = 0; break;
                              }
                         break;
              case 'Q' : done = 1;
                         break;
              }
          }
      close_window(buf);
      setmenucolors(&tmp);
    } void draw_half_box (char *right, char *left, char *top, char *bottom,
                int x, int y, int width, int height)
{
int i;
unsigned char temp[500];

for (i=0;i<height;i++)
    {
    left[i] =inpic(x,i+y,avw());
    right[i]=inpic(x+width,i+y,avw());
    outpic (x,i+y,(unsigned char)200,avw());
```

```
        outpic (x+width,i+y,(unsigned char)200,avw());
        } getrowavw(y,x,width,top);
   getrowavw(y+height,x,width,bottom);
   memset (temp,200,width);
   putrowavw(y,x,width,temp);
   putrowavw(y+height,x,width,temp);
   } void clear_half_box (char *right, char *left, char *top, char *bottom,
                int x, int y, int width, int height)
   {
   int i;

putrowavw(y,x,width,top);
   putrowavw(y+height,x,width,bottom);
   for (i=0;i<height;i++)
       {
       outpic (x,i+y,(unsigned char)left[i],avw());
       outpic (x+width,i+y,(unsigned char)right[i],avw());
       }
   } void position_half_box(int *x_coord, int *y_coord)
{
#define UpArrow 72
#define DnArrow 80
#define LfArrow 75
#define RtArrow 77
define RETURN  13 int x;
  int y;
  char c;
  char right_buffer[500];
  char left_buffer[500];
  char top_buffer[300];
  char bot_buffer[300];
  int done=0;
  windowtype *tbuf;
  int height=400;
  int width= 240;

tbuf = open_window(24,15,57,18,WHITE,CYAN,1,"");
  textcolor(WHITE);
  xycprintf(2,1,EGA_YELLOW,"Use arrow keys to position box");
  xycprintf(2,2,EGA_YELLOW,"Press return when complete...");

x = y = 40;
  draw_half_box(left_buffer,right_buffer,top_buffer,bot_buffer,x,y,width,height);
  while (!done)
    {
    if ((c = toupper(getch())) == RETURN) done=1;
    else if (c==0)
       {
       c=toupper(getch());
       if ( (c==UpArrow) || (c==DnArrow) || (c==RtArrow) || (c==LfArrow) )
          {
          clear_half_box(left_buffer,right_buffer,top_buffer,bot_buffer,x,y,width,height);
          if (c==UpArrow) y-=5;
          else if (c==DnArrow) y+=5;
          else if (c==RtArrow) x+=10;
          else if (c==LfArrow) x-=10;

if ((x+width) > x_image_stop) x=x_image_stop-width;
          if ((y+height) > y_image_stop) y=y_image_stop-height;
          if (x < x_image_start) x=x_image_start;
          if (y < y_image_start) y=y_image_start;

draw_half_box(left_buffer,right_buffer,top_buffer,bot_buffer,x,y,width,height);
          }
       }
    }
  clear_half_box(left_buffer,right_buffer,top_buffer,bot_buffer,x,y,width,height);
  *x_coord = x;
  *y_coord = y;
  close_window(tbuf);
}

/* ND mod void savehalfimage(int x, int y) */
void savehalfimage(void)
{
  void * buffer;
/*ND mod  windowtype *tbuf;
  char ch;*/
  int han;
  unsigned size;
  picture descr;

textcolor(WHITE);
  xycprintf(2,16,LIGHTCYAN,"Enter filename for image: ");
  getstring(outname);
  if (strlen(outname)==0)
```

```
        {
/*ND mod     close_window(tbuf); */
    return;
    } strupr(outname);
    makefilename(outname,PICTURE);
    xycprintf(2,17,LIGHTCYAN,"Enter description:");
    getstring(descr.name);

if ((han = open(outname,O_WRONLY | O_CREAT,S_IREAD | S_IWRITE)) != -1)
        {
        setcursor(SHORT_CURSOR);

strcpy(descr.marker,PICMARK);
        descr.size = HALFSIZE;
        _write(han,&descr,sizeof(picture));
/*      drawimage(HALFSIZE,NOWAIT,x,y);*/
        size = imagesize(0,0,240,100);
        if ((buffer = malloc(size)) == NULL) {
            closegraph();
            fprintf(stderr,"Error! Memory Allocation -- Save image\n");
            getch();
            fflush(stdin);
            exit(1);
            }
        getimage(0,0,240,100,buffer);
        _write(han,buffer,size);
        getimage(0,101,240,200,buffer);
        _write(han,buffer,size);
        getimage(0,201,240,300,buffer);
        _write(han,buffer,size);
        getimage(0,301,240,400,buffer);
        _write(han,buffer,size);
        free(buffer);
        close(han);
        closegraph();
        }
    else
        {
/*ND mod     close_window(tbuf);*/
        }
} void box_and_save(void)
{
    int box_x;
    int box_y;

position_half_box (&box_x, &box_y);
    drawimage(HALFSIZE,NOWAIT,box_x,box_y);
/*ND mod  savehalfimage(box_x, box_y);*/
    savehalfimage();
    closegraph();
} void pic_options(void)
    { char ch;
      imagelisttype imagelist;
      int done;
      int tag;
      char temp[64];

show_main("Picture Menu");
            /* Entire menu only active when
             * frame grabbed.
             */
    menuchoice_disable(picture_menu,'D'); menuchoice_disable(picture_menu,'E');
    menuchoice_disable(picture_menu,'R'); menuchoice_disable(picture_menu,'B');
    menuchoice_disable(picture_menu,'N'); menuchoice_disable(picture_menu,'A');
    menuchoice_disable(picture_menu,'X');
/*ND mod menuchoice_disable(picture_menu,'I'); */
    continuous();
    while ((ch = menuselect(25,10,picture_menu,&last_pm_option)) != 'Q') {
        switch(ch) {
            case 'F' : grabframe();
                       menuchoice_enable(picture_menu,'D'); menuchoice_enable(picture_menu,'E');
                       menuchoice_enable(picture_menu,'R'); menuchoice_enable(picture_menu,'B');
                       menuchoice_enable(picture_menu,'N'); menuchoice_enable(picture_menu,'A');
                       menuchoice_enable(picture_menu,'X');
                       break;
            case 'C' : continuous();
                       menuchoice_disable(picture_menu,'D'); menuchoice_disable(picture_menu,'E');
                       menuchoice_disable(picture_menu,'R'); menuchoice_disable(picture_menu,'B');
                       menuchoice_disable(picture_menu,'N'); menuchoice_disable(picture_menu,'A');
                       menuchoice_disable(picture_menu,'X');
                       break;
            case 'D' : switch(choose("Draw the Fullsized picture","or the Reduced one?",picsize_menu)) {
                           case 'F' : drawimage(FULLSIZE,1,0,0);
                                      break;
                           case 'R' : drawimage(REDUCED,1,0,0);
                                      break;
                           }
                       show_main("Picture Menu");
                       break;
```

```
                case 'E' : equalize_image();
                           break;
                case 'L' : do {
                              done = 1;
                              if (selectfile("c:\\saccade\\pictures\\*.pic",imagelist.image[0].name,&tag,45,4,
2,17)) {
                                  if (!validfile(makefilename(imagelist.image[0].name,PICTURE),PICMARK)) {
                                      extract_fn(temp,imagelist.image[0].name);
                                      strcat(temp," is not a valid");
                                      error(temp,"picture file");
                                      done = 0;
                                  }
                                  else { imagelist.size = 1;
                                         loadimage(&imagelist,1);
                                  }
                              }
                           } while (!done);
                           show_main("Picture Menu");
                           break;
                case 'S' : saveimage();
                           show_main("Picture Menu");
                           break;
                case 'R' : reduce_image();
                           break;
                case 'B' : binary_image(70);
                           break;
                case 'N' : reverse_image();
                           break;
                case 'A' : smooth_image();
                           break;
                case 'X' : box_and_save();
                           show_main("Picture Menu");
                           break;
            }
        }
    } void subject_registration(void)
  { windowtype *win;

win = open_window(5,10,75,20,WHITE,CYAN,1,"Registration");
    xycprintf(2,2,WHITE,"Subject Name: ");
    editstring(subjectinfo.name,"",40);
    xycprintf(2,3,WHITE,"Subject Number: ");
    editstring(subjectinfo.number,"",10);
    xycprintf(2,4,WHITE,"Subject Info:");
    xycprintf(4,5,WHITE,"-> ");
    editstring(subjectinfo.info,"",65);
    close_window(win);
  } main ()
  { char ch;
    int han;
    markertype marker;
    imagelisttype imagelist;
    windowtype *buf;

setcursor(NO_CURSOR);
    if ((han = open("saconfig.sc",O_RDONLY)) != -1) {
       _read(han,&filterpts, sizeof(int));
       _read(han,&calibpts, sizeof(int));
       _read(han,&box_lp_on,sizeof(int));
       _read(han,&nobox_lp_on,sizeof(int));
       _read(han,&total_lp,sizeof(int));
       _read(han,&num_box_lp,sizeof(int));
       _read(han,&useboxes,sizeof(int));
       close(han);
    }
    set_box_mark(box_lp_on);
    set_nobox_mark(nobox_lp_on);
    set_gaze_speed(num_box_lp);
/*ND mod*/ set_boxdef_boxes();
    initialize();
    continuous();
    initgaze(80,25,filterpts,calibpts);
    show_main("Main Menu");
    setmenucolors(&blue_menu);
    setfiletagging(0);
    while ((ch = menuselect(25,11,main_menu,&last_mm_option)) != 'Q') {
       switch(ch) {
          case 'D' : pic_options();
                     break;
          case 'T' : savetext();
                     break;
          case 'P' : show_main("Test Menu");
                     while ((ch = menuselect(25,11,test_menu,&last_tm_option)) != 'Q') {
                        switch (ch) {
                           case 'P' : single_test();
                                      show_main("Test menu");
                                      break;
                           case 'C' : buf = open_window(10,11,70,15,LIGHTCYAN,CYAN,1,"Input:");
                                      gotoxy(3,2);
                                      textcolor(WHITE);
                                      if (getnewfilename(outname,"Enter the filename to use for the Ba
```

```
tch file: ",BATCH)) {
                                      close_window(buf);
                                      han = open(outname,O_WRONLY | O_CREAT, S_IREAD | S_IWRITE);
                                      strcpy(marker,BTCMARK);
                                      _write(han,&marker,sizeof(markertype));
                                      while(getimagelist(&imagelist,1)) {
                                          _write(han,&imagelist,sizeof(imagelisttype));
                                      }
                                      close(han);
                                  }
                                  else close_window(buf);
                                  break;
                       case 'E': edit_batchfile();
                                  break;
                       case 'B': batch_test();
                                  show_main("Test menu");
                                  break;
                       case 'O': test_configure();
                                  break;
             /*ND mod*/ case 'I': getimagelist(&imagelist,0); /*Select images for working with the
                                                                 screen, not to use them for a test
*/
                                  loadimage(&imagelist,0);    /*0 tells load image not to
                                                                 erase the image screen */
                                  define_image_boxes();
                                  show_main("Picture Menu");
                                  break;
                                }
                       }
                       break;
             case 'A' : analysis_options();
                        break;
             case 'R' : subject_registration();
                        break;
        }
        show_main("Main Menu");
    }
    setcursor(SHORT_CURSOR);
    textbackground(BLACK);
    textcolor(CYAN);
    clrscr();
/*ND mod*/ dispose_activeboxlist(boxdef_boxes);
    if ((han = open("saconfig.sc",O_WRONLY | O_CREAT, S_IREAD | S_IWRITE)) != -1) {
        _write(han,&filterpts, sizeof(int));
        _write(han,&calibpts, sizeof(int));
        _write(han,&box_lp_on,sizeof(int));
        _write(han,&nobox_lp_on,sizeof(int));
        _write(han,&total_lp,sizeof(int));
        _write(han,&num_box_lp,sizeof(int));
        _write(han,&useboxes,sizeof(int));
        close(han);
    }
}

\032
``` sacresul.c

```
#include <stdio.h>
#include <stdlib.h>
#include <conio.h>
#include <fcntl.h>
#include <string.h>
#include <math.h>
#include <dos.h>
#include <ctype.h>
#include <io.h>
#include <alloc.h>
#include <graphics.h>
#include "c:\ericalib\tools.h"
#include "c:\ericalib\grtools.h"
#include "c:\ericalib\menu.h"
#include "c:\maryland\sacboxes.h"
#include "c:\maryland\saccade.h"
#include "c:\maryland\imagebox.h"

static menuitemtype analysis_menu[] = {
    {1,0,"Information Summary of results file"},
    {1,0,"List results on screen"},
    {1,4,"Set File Specification"},
    {1,0,"Superimpose lookpoints over images"},
    {1,0,"Graph results"},
    {1,4,"Get New results file for analysis"},
    {1,24,"Show results based on a Box file"},
    {1,0,"Quit"},
    {1,0,"EOM"},
};

static int last_am_option = 0;

static menuitemtype sup_menu[] = {
    {1,0,"Wait for key between look points"},
```

```
 {1,0,"Continuous look point display"},
 {1,0,"Abort"},
 {1,0,"EOM"}
 };

static menuitemtype box_menu[] = {
 {1,0,"Load in a new box file"},
 {1,0,"Text summary of box results"},
 {1,0,"Graph summary of box results"},
 {1,0,"Quit"},
 {1,0,"EOM"},
 };

imagelisttype images;
int numrecs;
int box_tlp;
unsigned box_hit[MAX_BOXES+1];
double box_sumpd[MAX_BOXES+1], box_tpd;
double box_sumpd2[MAX_BOXES+1],box_tpd2;

extern int image_loc[];
static subjecttype subjectinfo;

boxdeftype img_boxes[MAX_BOXES];    /* Used for user defined box locations */

/* Decides which quadrant a lookpoint is in. Returns quadrant 1-4 or 0
 * if not in quadrant. Note: The quadrants are numbers from 0 - 3 in the
 * structure imagelisttype.
 */
/* static unsigned whichquad(int x, int y)
   { x = x * 640/80;
     y = y * 350/25;
     if ((x > image_loc[0] - 10) && (x < image_loc[2] - 10)) {
        if ((y > image_loc[1] - 10) && (y < image_loc[5] - 10))
           return(1);
        if ((y > image_loc[5] - 10) && (y < image_loc[5] + 159 + 10))
           return(3);
        }
     if ((x > image_loc[2] - 10) && (x < image_loc[2] + 171 + 10)) {
        if ((y > image_loc[1] - 10) && (y < image_loc[5] - 10))
           return(2);
        if ((y > image_loc[5] - 10) && (y < image_loc[5] + 159 + 10))
           return(4);
        }
     return(0); */             /* Not in any box */
/*  }*/

/* Decides which sector a lookpoint is in. Returns quadrant 0, 1 or 2.
 * Note: The halves are numbers from 0 - NUMPICS in the structure
 * imagelisttype. This is the testing ground program.
 */
static unsigned whichhalf(int x, int y)
{
   x = x * (int)(640/80);
   y = y * (int)(350/25);
/*ND mod printf("Xg = %3d     Yg = %3d    ", x, y);*/
   if ((y > 100) && (y < 341)){
      if ((x < 257) && (x > -1)){
         return(1);
         }                                     /* in left box    */
      if ((x > 374) && (x < 641)){
         return(2);
         }                                     /* in right box   */
      else
         return(0);
      }
   else
      return(0);                                /* not in any box */
}

/* Decides if a lookpoint is in a user defined box. Returns 1
 * if it is and 0 if it is not.
 */
static unsigned inhalf(int x, int y, boxdeftype box)
{
   x = x * (int)(640/80);
   y = y * (int)(350/25);
   if (x >= box.ul.x && x <= box.br.x &&
       y >= box.ul.y && y <= box.br.y)
      return(1);
   else
      return(0);                                /* not in the box */
}

/* AUTHOR: Kevin S. Spetz
 * DATE:
 * Routine which reads the results file *resfile and breaks the data down
 * into a summary. Calculates the mean pupil diameter for the whole data
 * file, and also breaks the look-points down as to being on one of the NUMPICS
 * quadrants. Calculates the respective mean pupil diameters for each
 * quadrant too.
 */
```

```c
void summarize_results(char *resfile, int numrecs, datatype *list)
{ int count,tlp;
    int xl[4] = {0,45,0,45};
    int yl[4] = {4,4,14,14};
    unsigned quad[5];
    double sumpd[5],tpd;
    double sumpd2[5],tpd2;

/*ND mod*/for (count = 0; count < NUMPICS+1; count++) {
        quad[count] = 0;
        sumpd[count] = sumpd2[count] = 0.0;
        }
    tlp = 0;
    tpd = tpd2 = 0.0;
    textbackground(BLUE);
    clrscr();
    for (count = 0; count < numrecs; count++) {
        tlp++;
        tpd += (double) list->hd;
        tpd2+= (double) (list->hd * list->hd);
/*ND mod quad[whichquad(list->x,list->y)]++;
        sumpd[whichquad(list->x,list->y)] += (double) list->hd;
        sumpd2[whichquad(list->x,list->y)] += (double) (list->hd * list->hd);
*/
        quad[whichhalf(list->x,list->y)]++;
        sumpd[whichhalf(list->x,list->y)] += (double) list->hd;
        sumpd2[whichhalf(list->x,list->y)] += (double) (list->hd * list->hd);
        list++;
    }
                                /* Summary of All information in results file */
    draw_a_box(20,1,64,3,LIGHTCYAN,RED,0);
    xycprintf(23,2,LIGHTCYAN,"Overall Summary: %s",resfile);
    draw_a_box(13,5,65,23,LIGHTCYAN,CYAN,1);
    xycprintf(15,6,YELLOW,"Subject Name:    ");
    xycprintf(31,6,WHITE,subjectinfo.name);
    xycprintf(15,7,YELLOW,"Subject Number: ");
    xycprintf(31,7,WHITE,subjectinfo.number);
    xycprintf(15,8,YELLOW,"Imagefiles:");
/*ND mod*/
    for (count = 0; count < NUMPICS; count++) {
        if (count < images.size) {
            xycprintf(17,9 + (count * 2),BLACK,"%s",images.image[count].name);
            xycprintf(19,9 + (count * 2) + 1,DARKGRAY,"%s",getimagedescr(images.image[count].name));
        }
    }
    xycprintf(15,17,LIGHTCYAN,"-----------------------------------");
    xycprintf(24,18,WHITE,"n       = %d",tlp);
    if (tlp)
        xycprintf(24,19,WHITE,"\346(pd)   = %d",(int)(tpd/tlp));
    else xycprintf(24,19,LIGHTCYAN,"\346(pd)   = ?");
    xycprintf(24,20,WHITE,"\344(pd)   = %1.0f",tpd);
    xycprintf(24,21,WHITE,"\344(pd\375) = %1.0f",tpd2);
    if (tlp > 1)
        xycprintf(24,22,WHITE,"s       = %1.2f",sqrt((1.0/(tlp - 1.0))*(tpd2 - (tpd * tpd/tlp))));
    else xycprintf(24,22,LIGHTCYAN,"s       = ?");

xycprintf(35,25,BLACK,"Press a key");
    getch();
    clrscr();

/* Broken down summary of information */
    draw_a_box(20,1,64,1,RED,RED,0);
    xycprintf(22,1,WHITE,"Individual summaries: %s",resfile);
    draw_a_box(6,3,38,10,LIGHTCYAN,CYAN,1);
    draw_a_box(43,3,74,10,LIGHTCYAN,CYAN,1);
    draw_a_box(6,13,38,20,LIGHTCYAN,CYAN,1);
    draw_a_box(43,13,74,20,LIGHTCYAN,CYAN,1);
/*ND mod*/for (count = 0; count < NUMPICS; count++) {
        if (count < images.size)
            xycprintf(xl[count],yl[count],BLACK,"Image: %s",images.image[count].name);
        else xycprintf(xl[count],yl[count],LIGHTGRAY,"Image: none");
        xycprintf(xl[count],yl[count] + 1,WHITE,"n       = %d",quad[count + 1]);
        if (quad[count + 1])
            xycprintf(xl[count],yl[count] + 2,WHITE,"\346(pd)   = %d",(int)(sumpd[count + 1]/quad[count + 1]));
        else xycprintf(xl[count],yl[count] + 2,LIGHTCYAN,"\346      = ?");
        xycprintf(xl[count],yl[count] + 3,WHITE,"\344(pd)   = %1.0f",sumpd[count + 1]);
        xycprintf(xl[count],yl[count] + 4,WHITE,"\344(pd\375) = %1.0f",sumpd2[count + 1]);
        if (quad[count + 1] > 1)
            xycprintf(xl[count],yl[count] + 5,WHITE,"s       = %1.2f",sqrt((1.0/(quad[count + 1] - 1.0))*
    (sumpd2[count + 1] - (sumpd[count + 1] * sumpd[count + 1]/quad[count + 1]))));
        else xycprintf(xl[count],yl[count] + 5,LIGHTCYAN,"s       = ?");
    }
    draw_a_box(1,23,80,25,LIGHTCYAN,CYAN,0);
    xycprintf(3,24,BLACK,"Outside Images: ");
    xycprintf(19,24,WHITE,"n = %d",quad[0]);
    if(quad[0])
        xycprintf(27,24,WHITE,"\346 = %d", (int)(sumpd[0]/quad[0]));
    else xycprintf(27,24,LIGHTCYAN,"\346 = ?");
    xycprintf(36,24,WHITE,"\344(pd) = %1.0f",sumpd[0]);
    xycprintf(50,24,WHITE,"\344(pd\375) = %1.0f",sumpd2[0]);
    if (quad[0] > 1)
        xycprintf(68,24,WHITE,"s = %1.2f",sqrt((1.0/(quad[0] - 1.0))*(sumpd2[0] - (sumpd[0] * sumpd[0]/
quad[0]))));
```

```
    else xycprintf(68,24,LIGHTCYAN,"s - ?");
    getch();
    textbackground(BLACK);
  }

/* AUTHOR: Kevin S. Spetz
 * DATE:
 * Routine to list the results held in *resfile to the screen.
 */
void listresults(int numrecs, datatype *list)
  { int count;
    div_t temp;
  /* int ddd;
    datatype data;*/
    windowtype *buf0, *buf1, *buf2;

buf0 = open_window(3,3,38,8,BLACK,LIGHTGRAY,1,"Image Files");
    textcolor(BLACK);
    for (count = 0; count < images.size; count++)
      xycprintf(2,count+1,BLACK,"Image file %s",images.image[count].name);
    buf1 = open_window(40,2,77,5,BLACK,MAGENTA,1,"Subject Info");
    xycprintf(2,1,YELLOW,"Subject Name:");
    xycprintf(18,1,WHITE,subjectinfo.name);
    xycprintf(2,2,YELLOW,"Subject Number:");
    xycprintf(18,2,WHITE,subjectinfo.number);
    buf2 = open_window(13,8,74,23,LIGHTCYAN,CYAN,1,"");
    textcolor(WHITE);
    for (count = 0; count < numrecs; count++) {
/*        cprintf("%#3d:  Look Point (%2d,%2d),  Pupil Diameter (%2d)",count+1,list->x,list->y,list->hd
);*/
        cprintf("%#3d: Gaze (%2d,%2d), Diameter(H) (%2d) Time (%7.2f)",count+1,list->x,list->y,list->hd
,list->time);
        if (list->mark)
            cprintf(":  Mark (%c)\r\n",(char) list->mark);
        else cprintf("\r\n");
        temp = div(count+1,12);
        if (temp.rem == 0) {
            xycprintf(1,14,LIGHTGREEN,"Press any key to continue: 'Q' to quit");
            if (toupper(getch()) == 'Q') {
                cprintf("\r\n");
/*ND mod*/      count++;
                break;
            }
            clrscr();
        }
        list++;
    }
    cprintf("\n");
    cprintf("Listed %d data points\n",count);
    getch();
    close_window(buf2);
    close_window(buf1);
    close_window(buf0);
  }

/* AUTHOR: Kevin S. Spetz
 * DATE:
 * Routine which puts up a blank set of axis with x and y range values and
 * labels.
 */
static void graph_template(int ly, int uy, int lx, int ux, char *st)
  { int maxx, maxy;
    char temp[4];
    struct viewporttype vp;
    getviewsettings(&vp);
    maxx = vp.right - vp.left;
    maxy = vp.bottom - vp.top;
    settextjustify(CENTER_TEXT,CENTER_TEXT);
    changetextstyle(SMALL_FONT,HORIZ_DIR,5);
    setcolor(EGA_YELLOW);
    outtextxy(maxx/2, maxy/10, st);
    setcolor(EGA_CYAN);
    line(maxx * 0.2, maxy * 0.2, maxx * 0.2, maxy * 0.8);
    line(maxx * 0.2, maxy * 0.8, maxx * 0.8, maxy * 0.8);
    setcolor(EGA_LIGHTCYAN);
    changetextstyle(SMALL_FONT,HORIZ_DIR,4);
    itoa(ly,temp,10);
    outtextxy(maxx * 0.15, maxy * 0.8,temp);
    itoa(uy,temp,10);
    outtextxy(maxx * 0.15, maxy * 0.2, temp);
    itoa((uy + ly)/2,temp,10);
    outtextxy(maxx * 0.15, maxy * 0.5, temp);
    itoa(lx,temp,10);
    outtextxy(maxx * 0.2, maxy * 0.85, temp);
    itoa(ux,temp,10);
    outtextxy(maxx * 0.8, maxy * 0.85, temp);
    itoa((ux + lx)/2, temp, 10);
    outtextxy(maxx * 0.5, maxy * 0.85, temp);
  }

/* Routine to calculate the place for a new x value, based on current window,
```

```
 * curx, and totalx.
 */
static int newx(int curx, int totalx)
{   int maxx;
    struct viewporttype vp;
    getviewsettings(&vp);
    maxx = vp.right - vp.left;
    return ((maxx * 0.2 + curx * (maxx * 0.8 - maxx * 0.2)/(totalx) + 1));
}

/* Routine to calculate the place for a new y value, based on current window,
 * cury, and totaly.
 */
static int newy(int cury, int totaly)
{   struct viewporttype vp;
    int maxy;
    getviewsettings(&vp);
    maxy = vp.bottom - vp.top;
    return ((maxy * 0.8 - cury * (maxy * 0.8 - maxy * 0.2)/(totaly) + 1));
}

/* AUTHOR: Kevin S. Spetz
 * DATE:
 * Routine to present the data in *resfile in a graphical format. The data
 * are broken down into x look-point, y look-point, and pupil diameter and
 * then graphed separately.
 */
void graph_results (int numrecs, datatype *list)
{   int count;
    /*datatype *prevptr;*/
    int maxx, maxy;
    int oldx[4], oldy[4];
    char temp[64];

newsetupgraphics(DETECT,0);
    maxx = getmaxx(); maxy = getmaxy();
    setcolor(EGA_LIGHTGRAY);
    line(maxx/2,0,maxx/2,maxy);
    line(0,maxy/2,maxx,maxy/2);
    rectangle(0,0,maxx,maxy);
    setcolor(EGA_CYAN);
    setviewport(0,0,maxx/2,maxy/2,1);
/*ND mod graph_template(1,80,1,numrecs,"X Lookpoint");*/
/*ND mod*/ graph_template(1,640,1,numrecs,"X Lookpoint");
    setviewport(maxx/2,0,maxx,maxy/2,1);
/*ND mod graph_template(1,25,1, numrecs,"Y Lookpoint");*/
/*ND mod*/graph_template(1,350,1, numrecs,"Y Lookpoint");
    setviewport(maxx/2 + 1,maxy/2 + 1,maxx,maxy,1);
    graph_template(1,120,1,numrecs, "Pupil Diameter");
    setcolor(EGA_RED);
    outtextxy(110,160,"-- Horz");
    setcolor(EGA_MAGENTA);
    outtextxy(210,160,"-- Vert");
    setviewport(10,maxy /2 + 15,maxx/2,maxy,1);
    changetextstyle(SMALL_FONT,HORIZ_DIR,5);
    settextjustify(LEFT_TEXT,CENTER_TEXT);
    setcolor(WHITE);
    outtextxy(3,0.5 * textheight("X"),"* Images used in test");
    setcolor(CYAN);
    for (count = 0; count < images.size; count++) {
        outtextxy(35, (count + 1) * textheight("X") * 1.4 + 13,images.image[count].name);
    }
    setcolor(EGA_LIGHTCYAN);
    itoa(numrecs,temp,10);
    outtextxy(8,11 * textheight("X"),strcat(temp," data points taken"));
    setviewport(0,0,maxx/2,maxy/2,1);
    setcolor(EGA_RED);
    oldx[0] = oldx[1] = oldx[2] = oldx[3] = newx(count,numrecs);
    oldy[0] = newy(list->x,80);
    oldy[1] = newy(list->y,25);
    oldy[2] = newy(list->hd,120);
    oldy[3] = newy(list->vd,120);
    for (count = 0; count < numrecs; count++) {
        setviewport(0,0,maxx/2,maxy/2,1);
        line(oldx[0],oldy[0],newx(count,numrecs),newy(list->x,80));
        if (list->mark) {
            setcolor(EGA_YELLOW);
            line(newx(count,numrecs), 139, newx(count,numrecs),143);
            setcolor(EGA_RED);
        }
        oldx[0] = newx(count,numrecs);
        oldy[0] = newy(list->x,80);

setviewport(maxx/2 + 1,0,maxx,maxy/2,1);
        line(oldx[1],oldy[1],newx(count,numrecs),newy(list->y,25));
        if (list->mark) {
            setcolor(EGA_YELLOW);
            line(newx(count,numrecs), 139, newx(count,numrecs),143);
            setcolor(EGA_RED);
        }
        oldx[1] = newx(count,numrecs);
        oldy[1] = newy(list->y,25);

setviewport(maxx/2 + 1,maxy/2,maxx,maxy,1);
```

```c
            line(oldx[2],oldy[2],newx(count,numrecs),newy(list->hd,120));
            setcolor(EGA_MAGENTA);
            line(oldx[3],oldy[3],newx(count,numrecs),newy(list->vd,120));
            setcolor(EGA_RED);
            if (list->mark) {
               setcolor(EGA_YELLOW);
               line(newx(count,numrecs), 139, newx(count,numrecs),143);
               setcolor(EGA_RED);
               }
            oldx[3] = oldx[2] = newx(count,numrecs);
            oldy[2] = newy(list->hd,120);
            oldy[3] = newy(list->vd,120);
            list++;
            }
        getch();
        closegraph();
    }

/* AUTHOR: Kevin S. Spetz
 * DATE:
 * Routine that re-displays the stimuli used when generating the results
 * file *resfile. While the stimuli is re-displayed the raw data is
 * superimposed on the stimuli.
 */
void supimp_results(int waitforkey, int numrecs, datatype *list)
    { char intstr[4];
      int count;
      void *s;

loadimage(&images,0);
      if (screen_mode() != TEXT) {
         setcolor(12);
         changetextstyle(SMALL_FONT,HORIZ_DIR,5);
         settextjustify(CENTER_TEXT,CENTER_TEXT);
         for (count = 0; count < numrecs; count++) {
             s = place_lp(list->x * 8, list->y * 14,12);
             setviewport(0,300,50,349,1);
             clearviewport();
             setcolor(12);
             circle(25,25,list->hd/2);
             itoa(list->hd,intstr,10);
             outtextxy(25,25,intstr);
             setviewport(0,0,639,349,1);
             if (waitforkey) {
                if (toupper(getch()) == 'Q') break;
                }
             else if (kbhit()) {
                     if (toupper(getch()) == 'Q') break;
                     }
                  else delay(100);
             remove_lp(list->x * 8, list->y * 14, s);
             list++;
             }
         closegraph();
         }
      else { cputchar(1,2,CYAN,BLACK,80,'-');    /* In Text mode */
             cputchar(1,24,CYAN,BLACK,80,'-');
             for (count = 0; count < numrecs; count++) {
                 xycprintf(1,25,CYAN,"Pupil Diameter = %3d",list->hd);
                 s = place_lp(list->x,list->y,YELLOW);
                 if (waitforkey) {
                    if (toupper(getch()) == 'Q') break;
                    }
                 else if (kbhit()) {
                         if (toupper(getch()) == 'Q') break;
                         }
                      else delay(100);
                 remove_lp(list->x,list->y,s);
                 list++;
                 }
             }
    } int load_boxfile(char *boxfile)
{   int i;
    FILE *infile;
    markertype marker;

infile = fopen(makefilename(boxfile,BOX),"r");
    if(infile == NULL) {
       /* perror("System error encountered ");*/
       return(0);
       }
    else {
       fscanf(infile,"%s\n",marker);
       for (i=1; i<=MAX_BOXES; i++) {
           fscanf(infile,"%d %d %d %d\n",&img_boxes[i-1].ul.x,
                                        &img_boxes[i-1].ul.y,
                                        &img_boxes[i-1].br.x,
                                        &img_boxes[i-1].br.y);
           }
       }
    fclose(infile);
    return(1);
```

```c
} void summarize_box_info(datatype *listptr)
{
    int count, i, inabox;
    datatype *list;

list = listptr;
    for (count = 0; count <= MAX_BOXES; count++) {
        box_hit[count] = 0;
        box_sumpd[count] = box_sumpd2[count] = 0.0;
    }
    box_tlp = 0;
    box_tpd = box_tpd2 = 0.0;
    for (count = 0; count < numrecs; count++) {
        box_tlp++;
        box_tpd += (double) list->hd;
        box_tpd2+= (double) (list->hd * list->hd);
        inabox = 0;
        for (i=1; i<= MAX_BOXES; i++){
            if (inhalf(list->x,list->y,img_boxes[i-1])) {
                inabox = 1;
                box_hit[i]++;
                box_sumpd[i] += (double) list->hd;
                box_sumpd2[i] += (double) (list->hd * list->hd);
            }
        }
        if (!inabox) {
            box_hit[0]++;
            box_sumpd[0] += (double) list->hd;
            box_sumpd2[0] += (double) (list->hd * list->hd);
        }
        list++;
    }
}

/* AUTHOR: Nirav R. Desai (modification of Kevin S. Spetz's getresultsfile)
 * DATE:
 * Routine which asks the user for a box definition filename to use for
 * summarizing test data.
 */
int getboxfile(char *boxfname)
{   char errmsg[128];

if (!getboxesfile(boxfname,"*.*")){
        return(0);
    }
    else {
        if (load_boxfile(boxfname)) {
            return(1);
        }
        else {
            sprintf(errmsg,"%s is not a valid image boxes file",boxfname);
            error(errmsg,"");
            return(0);
        }
    }
} void box_text_summary(char *boxfile)
{   int count;
    int xl[4] = {0,45,0,45};
    int yl[4] = {4,4,14,14};
    textbackground(BLUE);
    clrscr();
                        /* Summary of All information in results file */
    draw_a_box(20,1,64,3,LIGHTCYAN,RED,0);
    xycprintf(23,2,LIGHTCYAN,"Overall Summary: %s",boxfile);
    draw_a_box(13,5,65,23,LIGHTCYAN,CYAN,1);
    xycprintf(15,6,YELLOW,"Subject Name:    ");
    xycprintf(31,6,WHITE,subjectinfo.name);
    xycprintf(15,7,YELLOW,"Subject Number: ");
    xycprintf(31,7,WHITE,subjectinfo.number);
    xycprintf(15,8,YELLOW,"Imagefiles:");
/*ND mod*/
    for (count = 0; count < NUMPICS; count++) {
        if (count < images.size) {
            xycprintf(17,9 + (count * 2),BLACK,"%s",images.image[count].name);
            xycprintf(19,9 + (count * 2) + 1,DARKGRAY,"%s",getimagedescr(images.image[count].name));
        }
    }
    xycprintf(15,17,LIGHTCYAN,"·····································");
    xycprintf(24,18,WHITE,"n        = %d",box_tlp);
    if (box_tlp)
        xycprintf(24,19,WHITE,"\346(pd)   = %d",(int) (box_tpd/box_tlp));
    else xycprintf(24,19,LIGHTCYAN,"\346(pd)   = ?");
    xycprintf(24,20,WHITE,"\344(pd)   = %1.0f",box_tpd);
    xycprintf(24,21,WHITE,"\344(pd\375) = %1.0f",box_tpd2);
    if (box_tlp > 1)
        xycprintf(24,22,WHITE,"s        = %1.2f",sqrt((1.0/(box_tlp - 1.0))*(box_tpd2 - (box_tpd * box_tp
d/box_tlp))));
    else xycprintf(24,22,LIGHTCYAN,"s        = ?");
```

```c
                    /* Broken down summary of box information */
    for (count = 0; count < MAX_BOXES; count++) {
        if ((count%4)==0) {
            xycprintf(35,25,BLACK,"Press a key");
            getch();
            clrscr();
            draw_a_box(20,1,64,1,RED,RED,0);
            xycprintf(22,1,WHITE,"Individual summaries: %s",boxfile);
            draw_a_box(6,3,38,10,LIGHTCYAN,CYAN,1);
            draw_a_box(43,3,74,10,LIGHTCYAN,CYAN,1);
            draw_a_box(6,13,38,20,LIGHTCYAN,CYAN,1);
            draw_a_box(43,13,74,20,LIGHTCYAN,CYAN,1);
        }
        if (img_boxes[count].ul.x >=0 )
            xycprintf(xl[count%4],yl[count%4],BLACK,"Box: %d",count+1);
        else xycprintf(xl[count%4],yl[count%4],LIGHTGRAY,"Box: %d undefined",count+1);
        xycprintf(xl[count%4],yl[count%4] + 1,WHITE,"n       = %d",box_hit[count + 1]);
        if (box_hit[count + 1])
            xycprintf(xl[count%4],yl[count%4] + 2,WHITE,"\346(pd)    = %d",(int)(box_sumpd[count + 1]/box_hit[count +1]));
        else xycprintf(xl[count%4],yl[count%4] + 2,LIGHTCYAN,"\346     = ?");
        xycprintf(xl[count%4],yl[count%4] + 3,WHITE,"\344(pd)   = %1.0f",box_sumpd[count + 1]);
        xycprintf(xl[count%4],yl[count%4] + 4,WHITE,"\344(pd\375) = %1.0f",box_sumpd2[count + 1]);
        if (box_hit[count + 1] > 1)
            xycprintf(xl[count%4],yl[count%4] + 5,WHITE,"s       = %1.2f",sqrt((1.0/(box_hit[count + 1] - 1.0))*(box_sumpd2[count + 1] - (box_sumpd[count + 1] * box_sumpd[count + 1]/box_hit[count + 1]))));
        else xycprintf(xl[count%4],yl[count%4] + 5,LIGHTCYAN,"s      = ?");
    }
    draw_a_box(1,23,80,25,LIGHTCYAN,CYAN,0);
    xycprintf(3,24,BLACK,"Outside All Boxes: ");
    xycprintf(23,24,WHITE,"n = %d",box_hit[0]);
    if(box_hit[0])
        xycprintf(31,24,WHITE,"\346 = %d", (int)(box_sumpd[0]/box_hit[0]));
    else xycprintf(31,24,LIGHTCYAN,"\346 = ?");
    xycprintf(40,24,WHITE,"\344(pd) = %1.0f",box_sumpd[0]);
    xycprintf(54,24,WHITE,"\344(pd\375) = %1.0f",box_sumpd2[0]);
    if (box_hit[0] > 1)
        xycprintf(72,24,WHITE,"s = %1.2f",sqrt((1.0/(box_hit[0] - 1.0))*(box_sumpd2[0] - (box_sumpd[0] * box_sumpd[0]/box_hit[0]))));
    else xycprintf(72,24,LIGHTCYAN,"s = ?");
    xycprintf(30,25,RED,"Press a key to continue");
    getch();
    textbackground(BLACK);
} void box_graph_summary(void)
{
    unsigned int dummyx, dummyy;
    register int box;
    char *message;
    unsigned int *boxptr;
    char boxinfo[16];

loadimage(&images,0);
    setfillstyle(SOLID_FILL,BLACK);
    bar(0,0,639,35);
    settextstyle(SMALL_FONT,HORIZ_DIR,5);
    settextjustify(CENTER_TEXT,CENTER_TEXT);
    setcolor(EGA_WHITE);
    outtextxy(320,17,"Box# # Lookpoints   Mean(pd)   Sum(pd)   Sum(pd*pd)   Std.Dev");
    setcolor(WHITE);
    while ((box = choose_box_num("Click on the box whose summary you wish to see (0 to quit):",0))!=0)
    {
        if (img_boxes[box-1].ul.x == -1) {
            bar(0,70,639,95);
            sound(400);
            if ((message=malloc(61*sizeof(char)))!=NULL) {
                sprintf(message,"Box %d is not defined, click the mouse to continue\n",box);
                outtextxy(0,75,message);
                delay(200);
                nosound();
                get_mouse_pos(&dummyx, &dummyy);
                free(message);
            }
            bar(0,70,639,95);
        }
        else {
            boxptr = show_box(img_boxes[box-1].ul.x,img_boxes[box-1].ul.y,
                    img_boxes[box-1].br.x,img_boxes[box-1].br.y,
                    EGA_WHITE);
            bar(0,36,639,69);
            setcolor(EGA_LIGHTMAGENTA);
            settextstyle(SMALL_FONT,HORIZ_DIR,5);
            settextjustify(CENTER_TEXT,CENTER_TEXT);
            sprintf(boxinfo,"%d\n",box);
            outtextxy(90,45,boxinfo);
            sprintf(boxinfo,"%d\n",box_hit[box]);
            outtextxy(170,45,boxinfo);
            if (box_hit[box])
                sprintf(boxinfo,"%d\n", (int)(box_sumpd[box]/box_hit[box]));
            else sprintf(boxinfo,"?");
            outtextxy(260,45,boxinfo);
            sprintf(boxinfo,"%1.0f\n",box_sumpd[box]);
            outtextxy(350,45,boxinfo);
```

```c
            sprintf(boxinfo,"%1.0f\n",box_sumpd2[box]);
            outtextxy(440,45,boxinfo);
            if (box_hit[box] > 1)
               sprintf(boxinfo,"%1.2f\n",sqrt((1.0/(box_hit[box] - 1.0))*(box_sumpd2[box] - (box_sumpd[bo
x] * box_sumpd[box]/box_hit[box]))));
            else sprintf(boxinfo,"?\n");
            outtextxy(530,45,boxinfo);
            settextstyle(SMALL_FONT,HORIZ_DIR,4);
            settextjustify(LEFT_TEXT,CENTER_TEXT);
            remove_box(img_boxes[box-1].ul.x,img_boxes[box-1].ul.y,
               img_boxes[box-1].br.x,img_boxes[box-1].br.y,boxptr,1);
            free(boxptr);
         }
      }
      closegraph();
   }

/* AUTHOR: Nirav R. Desai (modified from Kevin S. Spetz's summarize_results)
 * DATE:
 * Routine which reads the datalist and breaks the data down into a summary.
 * Calculates the mean pupil diameter for the whole data file, and also
 * breaks the look-points down as to being on one of the MAX_BOXES boxes
 * Calculates the respective mean pupil diameters for each box too.
 */
void box_results(char *boxfile, datatype *list)
{  register char ch;
   char boxfname[50], temp[50], *tmp;
   static int last_bm_option = 0;

strcpy(boxfname,boxfile);
   if (strncmp(boxfname,"\0",1)) {
      summarize_box_info(list);
   }
   else {
      menuchoice_disable(box_menu,'T');
      menuchoice_disable(box_menu,'G');
   }
   show_main("Box Menu");
   if ((tmp=malloc(80*sizeof(char)))!=NULL) {
      sprintf(tmp,"Current Box File: %s",makefilename(boxfname,BOX));
      remove_status();
      status(tmp);
      free(tmp);
   }
   while ((ch = menuselect(25,11,box_menu,&last_bm_option)) != 'Q') {
      switch(ch) {
         case 'L' :
            strcpy(temp,boxfname);
            if (!getboxfile(boxfname))
               strcpy(boxfname,temp);
            if (strncmp(boxfname,"\0",1)) {
               summarize_box_info(list);
               menuchoice_enable(box_menu,'T');
               menuchoice_enable(box_menu,'G');
            }
            break;
         case 'T' :
            box_text_summary(boxfname);
            break;
         case 'G' :
            box_graph_summary();
            break;
      }
      switch(ch) {
         case 'Q': break;
         default :
            show_main("Box Menu");
            if ((tmp=malloc(80*sizeof(char)))!=NULL) {
               sprintf(tmp,"Current Box File: %s",makefilename(boxfname,BOX));
               remove_status();
               status(tmp);
               free(tmp);
            }
            break;
      }
   }
} datatype *load_resfile(char *resfile, datatype *datalist)
{  int han;
   char *temp;
   datatype dummy;
   datatype *dataptr;
   markertype marker;

numrecs = 0;
   if (datalist != NULL)
      free(datalist);
   if ((han = open(resfile,O_RDONLY)) != -1) {
      _read(han,&marker,sizeof(markertype));
      _read(han,&subjectinfo,sizeof(subjecttype));
      _read(han,&images,sizeof(imagelisttype));
      while (_read(han,&dummy,sizeof(datatype)) == sizeof(datatype))
```

```c
      numrecs++;
   close(han);
   }
  else { fprintf(stderr,"Error loading file\n");
        exit(-1);
        }
  if ((datalist = (datatype *) malloc(sizeof(datatype) * numrecs)) == NULL) {
     fprintf(stderr,"Error! Memory Allocation, load_resfile \n");
     exit(-1);
     }
  dataptr = datalist;
  if ((han = open(resfile,O_RDONLY)) != -1) {
     _read(han,&marker,sizeof(markertype));
     _read(han,&subjectinfo,sizeof(subjecttype));
     _read(han,&images,sizeof(imagelisttype));
     while (_read(han,dataptr++,sizeof(datatype)) == sizeof(datatype));
     close(han);
     }
  else { fprintf(stderr,"Error loading file \n");
        exit(-1);
        }
  if ((temp = malloc(60*sizeof(char)))!=NULL) {
     sprintf(temp,"Data file %s successfully loaded.",resfile);
     message(temp);
     free(temp);
     }
   return(datalist);
  } void analysis_options(void)
{ char ch;
  char resultname[50], temp[MAXPATH], boxfname[50];
  char res_filespec[8] = "*";
  windowtype *buf;
  datatype *datalist = NULL;
  int bfloaded = 0;

show_main("Analysis Menu");
  menuchoice_disable(analysis_menu,'S');
  menuchoice_disable(analysis_menu,'L');
  menuchoice_disable(analysis_menu,'I');
  menuchoice_disable(analysis_menu,'G');
  menuchoice_disable(analysis_menu,'B');
  while ((ch = menuselect(25,11,analysis_menu,&last_am_option)) != 'Q') {
     switch(ch) {
        case 'S' :
           switch(choose("Select results Superposition","Mode",sup_menu)) {
              case 'N' :
                 supimp_results(1,numrecs,datalist);
                 break;
              case 'C' :
                 supimp_results(0,numrecs,datalist);
                 break;
              }
           show_main("Analysis Menu");
           sprintf(temp,"Current File: %s",resultname);
           status(temp);
           break;
        case 'L' :
           listresults(numrecs, datalist);
           break;
        case 'I' :
           summarize_results(resultname, numrecs, datalist);
           show_main("Analysis Menu");
           sprintf(temp,"Current File: %s",resultname);
           remove_status();
           status(temp);
           break;
        case 'G' :
           graph_results(numrecs, datalist);
           show_main("Analysis Menu");
           sprintf(temp,"Current File: %s",resultname);
           remove_status();
           status(temp);
           break;
        case 'N' :
           strcpy(temp,resultname);
           if (!getresultsfile(resultname,res_filespec)) {
              strcpy(resultname,temp);
              }
           else {
              sprintf(temp,"Current File: %s",resultname);
              remove_status();
              status(temp);
              datalist = load_resfile(resultname, datalist);
              if (validfile(makefilename(resultname,RESULTS),RESMARK)) {
                 menuchoice_enable(analysis_menu,'S');
                 menuchoice_enable(analysis_menu,'L');
                 menuchoice_enable(analysis_menu,'I');
                 menuchoice_enable(analysis_menu,'G');
                 menuchoice_enable(analysis_menu,'B');
                 xycprintf(60,2,WHITE,"Core = %u",coreleft());
                 status(temp);
                 }
              strcpy(boxfname,images.boxdefs);
              bfloaded = load_boxfile(boxfname);
```

```
              }
              break;
           case 'B' :
              if (!bfloaded) {
                 if (load_boxfile(boxfname))
                    box_results(makefilename(boxfname,BOX),datalist);
                 else box_results("\0",datalist);
              }
              else box_results(makefilename(boxfname,BOX),datalist);
              bfloaded = 0;
              show_main("Analysis Menu");
              sprintf(temp,"Current File: %s",resultname);
              remove_status();
              status(temp);
              break;
           case 'F' :
              buf = open_window(20,10,60,15,WHITE,CYAN,1,"");
              textcolor(WHITE);
              xycprintf(4,4,BLACK,"Use wildcards * and ?");
              xycprintf(2,2,LIGHTCYAN,"Enter File Specification: ");
              if (!editstring(res_filespec,"",8))
                 strcpy(res_filespec,"*");
              close_window(buf);
              break;
        }
    }
    if (datalist != NULL) free(datalist);
}\032
``` sacio.c

```c
include <stdio.h>
#include <stdlib.h>
#include <alloc.h>
#include <dos.h>
#include <ctype.h>
#include <io.h>
#include <string.h>
#include <conio.h>
#include <dir.h>
#include <stat.h>
#include <fcntl.h>
#include "c:\maryland\saccade.h"
#include "c:\ericalib\tools.h"
#include "c:\ericalib\menu.h"

static menuitemtype yesno_menu[] = {
   {1,0,"Yes"},
   {1,0,"No"},
   {1,0,"EOM"}
   };

static menuitemtype boxonoff_menu[] = {
   {1,0,"Active"},
   {1,0,"Inactive"},
   {1,0,"EOM"}
   };

static menuitemtype text_box_menu[] = {
   {1,0,"1: Box 1          (_ _ \334)"},
   {1,0,"2: Box 2          (_ \334 _)"},
   {1,0,"3: Box 1 & 2      (_ \334 \334)"},
   {1,0,"4: Box 3          (\334 _ _)"},
   {1,0,"5: Box 1 & 3      (\334 _ \334)"},
   {1,0,"6: Box 2 & 3      (\334 \334 _)"},
   {1,0,"7: Box 1, 2 & 3  (\334 \334 \334)"},
   {1,0,"Quit (none)"},
   {1,0,"EOM"}
   };

/* AUTHOR: Kevin S. Spetz
 * DATE:
 * Routine that adds to the path of a filename the correct directory and
 * extension information; depends upon the file type.
 */
char *makefilename(char *mfn, int typefile)
   { char drive[MAXDRIVE], dir[MAXDIR],name[MAXFILE],ext[MAXEXT];
     fnsplit(mfn,drive,dir,name,ext);
     if (strlen(dir) == 0) {
        switch(typefile) {
           case BATCH   : strcpy(dir,"\\SACCADE\\BATCH\\");
                          break;
           case RESULTS : strcpy(dir,"\\SACCADE\\RESULTS\\");
                          break;
           case PICTURE : strcpy(dir,"\\SACCADE\\PICTURES\\");
                          break;
           case S_TEXT  : strcpy(dir,"\\SACCADE\\TEXT\\");
                          break;
           case BOX     : strcpy(dir,"\\SACCADE\\BOX\\");
                          break;
        }
     }
```

```
            if (strlen(ext) == 0) {
               switch(typefile) {
                   case BATCH    : strcpy(ext,".BTC");
                                   break;
                   case RESULTS  : strcpy(ext,".RES");
                                   break;
                   case PICTURE  : strcpy(ext,".PIC");
                                   break;
                   case S_TEXT   : strcpy(ext,".TXT");
                                   break;
                   case BOX      : strcpy(dir,".BOX");
                                   break;
               }
            }
      fnmerge(mfn,drive,dir,name,ext);
      strupr(mfn);
      return(mfn);
   }

/* AUTHOR: Kevin S. Spetz
 * DATE:
 * Function attempts to open a file with the attributes *attr. Should be
 * called something else since it will also open binary files, etc. Returns
 * success or failure.
 */
unsigned char create_textoutfile(FILE *h,char *st,char *attr)

{ h = fopen(st, attr);
     if (h == NULL)
         return(0);
     else return(1);
   }

/* AUTHOR: Kevin S. Spetz
 * DATE:
 * Routine which prompts the user for a new filename and then, according
 * to the type of file specified by typefile, checks to see if a file
 * of that name exists. If one does it verifies the user's choice. If the
 * user elects to, a new file name can be entered.
 */
unsigned getnewfilename(char *f, char *msg, int typefile)
    { unsigned x,y,done = 0;
      int han;
      x = wherex();
      y = wherey();
      while (!done) {
         xycprintf(x,y,LIGHTCYAN,"%s",msg);
         clreol();
         if (strlen(getstring(f)) > 0 ) {
             if ((han = creatnew(makefilename(f,typefile),0)) != -1)
                 done = 1;
             else {  switch(verify("File Already Exists","Continue with Filename",yesno_menu)) {
                        case 'Y' : han = creat(f,S_IREAD|S_IWRITE); done = 1; break;
                     }
                  close(han);
                  }
             else return(0);
         }
      remove(f);
      return(1);
    }

/* AUTHOR: Nirav R. Desai (modifying Kevin Spetz's getnewfilename)
 * DATE:
 * Routine which prompts the user for a box filename and then, according
 * to the type of file specified by typefile, checks to see if a file
 * of that name exists. If one does, it verifies the user's choice.
 * Otherwise it returns 0.
 */
unsigned getboxfilename(char *f, char *msg)
{ unsigned x,y,done = 0;
  FILE *fn;
  x = wherex();
  y = wherey();
  while (!done) {
     xycprintf(x,y,LIGHTCYAN,"%s",msg);
     clreol();
     if ((editstring(f,"",15)) && (strlen(f)>0) ) {
        if ((fn= fopen(makefilename(f,BOX),"r")) !=NULL) {
           fclose(fn);
           done = 1;
        }
        else {
           switch(verify("File Does Not Exist","Reenter Filename?",yesno_menu)) {
              case 'N' : return(0);
           }
        }
     }
     else return(0);
  }
  return(1);
```

```c
/* AUTHOR: Kevin S. Spetz
 * DATE:
 * According to the character string *vl, the function checks the file *st
 * to make sure that it begins with the string *vl. If it does it is assumed
 * to be of the correct type. Current markers are: PIC for pictures, TXT for
 * text files, BTC for batch files, and RS1 for results files.
 */
unsigned validfile(char *st, char *vl)
{   int han;
    markertype marker;
    FILE *infile;

if (strcmp(vl,BOXMARK)==0) {
        infile = fopen(makefilename(st,BOX),"r");
        if (infile ==NULL) {
           fclose(infile);
           return(0);
        }
        else {
           fscanf(infile,"%s\n",marker);
           fclose(infile);
           if (strcmp(marker,vl)==0)
              return(1);
           else return(0);
        }
    }
    else {
       if ((han = open(st,O_RDONLY)) != -1) {
          _read(han,&marker,sizeof(markertype));
          close(han);
          if (strcmp(marker,vl) == 0)
             return(1);
          else return(0);
       }
       else return(0);
    }
}

/* AUTHOR: Kevin S. Spetz
 * DATE:
 * Routine which asks the user for a filename to store results in. Verifies
 * before accepting an existing filename.
 */
unsigned getresultsfile(char *resultsname ,char *filespec)
    { int done;
      windowtype *buf;
      int rv;
      int tag;
      char fn[128], errmsg[128];

buf = open_window(5,2,50,4,LIGHTCYAN,CYAN,1,"");
      textcolor(WHITE);
      done = 0;
      strcpy(fn,filespec);
      while (!done) {
         xycprintf(2,1,WHITE,"Select a results file to view: ");
         if (selectfile(makefilename(fn,RESULTS),resultsname,&tag,24,7,3,15)) {
             if (validfile(makefilename(resultsname,RESULTS),RESMARK)) {
                done = 1;
                rv = 1;
             }
             else { sprintf(errmsg,"%s is not a valid results file",resultsname);
                    error(errmsg,"");
                  }
         }
         else { done = 1;
                rv = 0;
              }
      }
      close_window(buf);
      return(rv);
   }

/* AUTHOR: Mirav R. Desai (modified Kevin S. Spetz's getresultsfile)
 * DATE:
 * Routine which asks the user for a filename to store results in. Verifies
 * before accepting an existing filename.
 */
unsigned getboxesfile(char *boxesname ,char *filespec)
    { int done;
      windowtype *buf;
      int rv;
      int tag = 0;
      char fn[128], errmsg[110];

buf = open_window(5,2,50,4,LIGHTCYAN,CYAN,1,"");
      textcolor(WHITE);
      done = 0;
      strcpy(fn,filespec);
      while (!done) {
         xycprintf(2,1,WHITE,"If desired, select a box file to use: ");
         if (selectfile(makefilename(fn,BOX),boxesname,&tag,24,7,3,15)) {
             if (validfile(makefilename(boxesname,BOX),BOXMARK)) {
```

```
                    done = 1;
                    rv = 1;
                    }
            else { sprintf(errmsg,"%s is not a valid box file",boxesname);
                    error(errmsg,"");
                    }
                }
        else { done = 1;
                rv = 0;
                }
            }
    close_window(buf);
    return(rv);
    } static menuitemtype test_type_menu[] = {
    {1,0,"Picture"},
    {1,0,"Text"},
    {1,0,"Quit"},
    {1,0,"EOM"}
    };

/* AUTHOR: Kevin S. Spetz
 * DATE:
 * Routine which prompts the user for a list of images to display on the
 * screen.
 */
/* modified 27 MAR 90, Greg Schubert */
unsigned getimagelist(imagelisttype *i,int test)
    { int done,count,j, tag;
    char fname[128], errmsg[128], tmp[16];
    windowtype *buf,*buf2;
    /*ND mod*/ char boxfname[128]; char box_filespec[8] = "*.*";

count = done = 0;

/*ND mod*/ for (j = 0; j < NUMPICS; j++)
        strcpy(i->image[j].name,'\0');
    textcolor(WHITE);

switch(choose("Select Test Screen","Type",test_type_menu)) {
        case 'T' :
            buf = open_window(4,4,41,8,BLACK,LIGHTGRAY, 1,"Text Screen:");
            while (!done) {
                xycprintf(4,2,BLACK,"Text filename : ");
                if (selectfile("c:\\saccade\\text\\*.txt",fname,&tag,45,4,2,17)) {
                    if (validfile(makefilename(fname,S_TEXT),TXTMARK)) {
                        strcpy(i->image[count].name,fname);
                        xycprintf(21, 2, WHITE,"%s", extract_fn(tmp,fname));
                        i->size = count = 1;
                        switch(choose("Which Text Boxes, if any, ","should be active?",text_box_menu)) {
                            case '1' : i->image[0].active = 1; break;
                            case '2' : i->image[0].active = 2; break;
                            case '3' : i->image[0].active = 3; break;
                            case '4' : i->image[0].active = 4; break;
                            case '5' : i->image[0].active = 5; break;
                            case '6' : i->image[0].active = 6; break;
                            case '7' : i->image[0].active = 7; break;
                            case 'Q' : i->image[0].active = 0; break;
                            }
                        done = 1;
                        }
                    else { sprintf(errmsg,"%s is not a",fname);
                        error(errmsg,"valid text file");
                        }
                    }
                }
            break;
        case 'P' :
            buf = open_window(4,4,43,11,BLACK,LIGHTGRAY,1,"Images:");
            while (!done) {
                xycprintf(4,2 + count,BLACK,"Image filename #%d = ",count + 1);
                clreol();
                if (selectfile("c:\\saccade\\pictures\\*.pic",fname,&tag,45,4,2,17)) {
                    if (validfile(makefilename(fname,PICTURE),PICMARK)) {
                        strcpy(i->image[count].name,fname);
                        xycprintf(24, 2 + count, WHITE, "%s", extract_fn(tmp,fname));
                        switch(choose("Is this image active","or inactive?",boxonoff_menu)) {
                            case 'A' :
                                i->image[count].active = 1;
                                xycprintf(38,2 + count,YELLOW,"A");
                                break;
                            case 'I' :
                                i->image[count].active = 0;
                                xycprintf(38,2 + count,YELLOW,"I");
                                break;
                            }
/* mod */               if (++count > (NUMPICS-1) ) {
                            i->size = count;
                            done = 1;
                            }
                        }
```

```
       else { sprintf(errmsg,"%s is not a",fname);
              error(errmsg,"");
            }
          }
        else done = 1;
        }
      i->size = count;
      done = 0;
      break;
    case 'Q' :
      count = 0;
      done = 1;
      return(count);
    }
  if ((test) && (count > 0)) {
    buf2 = open_window(10,14,70,18,LIGHTCYAN,CYAN,1,"Input:");
    gotoxy(4,2);
    textcolor(WHITE);
    if (!getnewfilename(fname,"Enter the filename to use for the Results: ",RESULTS))
       count = 0;
    strcpy(i->results,fname);
    close_window(buf2);
/*ND mod for assigning a set of image boxes to the imagelist*/
    buf2 = open_window(10,14,75,18,LIGHTCYAN,CYAN,1,"Input:");
    gotoxy(4,2);
    textcolor(WHITE);
/*      if (!getboxfilename(boxfname,"Enter the filename to use for Box definitions: "))
          count = 0;
*/    if (!getboxesfile(boxfname,box_filespec))
        strcpy(boxfname,"");;
      strcpy(i->boxdefs,boxfname);
      close_window(buf2);
    }
  close_window(buf);
  return(count);
 }

/* AUTHOR: Kevin S. Spetz
 * DATE:
 * Function that accepts the name of a picture file, and then reads from
 * that file a description of the picture. If the file sent is not a
 * picture file, or does not exist, appropriate messages are returned.
 */
char *getimagedescr(char *iname)
 { int han;
   picture *descr;
   char temp[128];

if ((descr = (picture *) malloc(sizeof(picture))) == NULL) {
     fprintf(stderr,"Error! Memory Allocation -- getimagedescr");
     exit(0);
   }
   if (validfile(iname,TXTMARK)) {
     free(descr);
     return("Text file");
   }
   if (validfile(iname,PICMARK)) {
     if ((han = open(iname,O_RDONLY)) != -1) {
       _read(han,descr,sizeof(picture));
       strcpy(temp,descr->name);
       free(descr);
       close(han);
       if (strlen(temp) > 40) {
         temp[43] = 0;              /* Set terminating flag in name */
         return((char *) strcat(temp,"+\0"));
       }
       else {
              return((char *) temp);
            }
       }
     }
   free(descr);
   sprintf(temp,"No File found. ",iname);
   return(temp);
 }
```

What is claimed is:

1. An apparatus for testing the eye response of a subject to test stimuli comprising:
 a presentation device for presenting an image to a subject as a test stimuli;
 an eye-look detector for detecting a series of lookpoints of the parts of said image being viewed by said subject; and
 a computer including a storage device for recording said lookpoints and a program having a means for determining said lookpoints, a means for correlating said lookpoints to locations on said image, and a means for superimposing said lookpoints on said image for review.

2. The apparatus of claim 1 wherein said eyelook detector is located remotely to the body of said subject.

3. The apparatus of claim 2 wherein said eyelook detector includes an infrared sensitive video camera and LED source that backlights the subject's pupil by the bright eye effect and creates a glint on subject's cornea and said program includes means for determining the center of said pupil and the distance and direction between the pupil's center and the glint.

4. The apparatus of claim 3 wherein said presentation device is a computer screen display.

5. The apparatus of claim 3 wherein said program includes means for establishing an area of interest in said visual image and means for determining said lookpoints that fall within said area of interest.

6. The apparatus of claim 3 wherein multiple images are presented on said presentation device and said program includes means for permitting a comparison between the subject's responses to the different images.

7. The apparatus of claim 3 wherein said video camera is utilized to capture and enter images into said apparatus.

8. The apparatus of claim 1 wherein said program includes means that determine a subject's pupil diameter simultaneously with the determination of a lookpoint.

9. The apparatus of claim 8 wherein said program includes a means that develops a graph of said lookpoints and pupil diameters measured during a test.

10. The apparatus of claim 8 wherein said program includes means that display an icon representing a lookpoint superimposed on said image and simultaneously displays the pupil diameter of said lookpoint.

11. The apparatus of claim 8 wherein said program includes means that develops a summary of the number of points, the pupil diameter and the standard deviation of the size of the pupil and presents said information in display format.

12. A method for testing the eye response of a subject to test stimuli comprising the following steps:
   displaying to the subject an image as a test stimuli;
   determining by an eyelook detector a series of lookpoints of where said subject is looking on said image;
   recording said series of lookpoints in a computer storage device; and
   superimposing said series of lookpoints onto said image after the test.

13. The method of claim 12 wherein the step of determination of said series of lookpoints include shining an infrared light into the subject's pupil from an LED mounted coaxially with an infrared sensitive video camera creating a glint on subject's cornea and calculating the lookpoints from the distance and direction between the center of the pupil and the glint.

14. The method of claim 13 wherein the step of displaying of the image is carried out by displaying the image on a computer screen.

15. The method of claim 13 which includes the steps of placing a box around an area of interest on said images and determining the lookpoints that fall with said box.

16. The method of claim 12 which includes the steps of displaying multiple images simultaneously and comparing the subject's response to the various images.

17. The method of claim 13 which includes the step of creating the images by capturing and entering the image using said infrared sensitive video camera.

18. The method of claim 12 which includes the step of determining the subject's pupil diameter simultaneously with determining the lookpoint.

19. The method of claim 18 which includes the step of presenting a graph of said lookpoints and pupil diameters measured during the test.

20. The method of claim 18 which includes the step of summarizing on a display the number of lookpoints, the pupil diameter and the standard deviation of the size of the pupil.

* * * * *